US 6,554,763 B1

(12) United States Patent
Amano et al.

(10) Patent No.: US 6,554,763 B1
(45) Date of Patent: Apr. 29, 2003

(54) RELAXATION GUIDANCE DEVICE AND BIOFEEDBACK GUIDANCE DEVICE

(75) Inventors: Kazuhiko Amano, Suwa (JP); Kazuo Uebaba, Yokohama (JP); Hitoshi Ishiyama, Toride (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/542,789

(22) Filed: Apr. 4, 2000

Related U.S. Application Data

(62) Division of application No. 09/029,706, filed as application No. PCT/JP97/02278 on Jul. 2, 1997, now abandoned.

(30) Foreign Application Priority Data

| Jul. 9, 1996 | (JP) | 8-179640 |
| Jul. 10, 1996 | (JP) | 8-181027 |
| Jun. 16, 1997 | (JP) | 9-159052 |

(51) Int. Cl.[7] .......................... A61B 5/00; A67M 21/00
(52) U.S. Cl. ........................................ 600/26
(58) Field of Search .................. 600/300, 26–28, 600/547, 529, 481; 128/897, 898

(56) References Cited

U.S. PATENT DOCUMENTS

| 3,855,998 A | | 12/1974 | Hidalgo-Briceno | |
| 4,008,714 A | * | 2/1977 | Silva et al. | 434/433 |
| 4,184,485 A | * | 1/1980 | Agoston | 128/905 |
| 4,573,472 A | * | 3/1986 | Ito | 434/262 |
| 5,076,281 A | | 12/1991 | Gavish | |
| 5,101,831 A | | 4/1992 | Koyama et al. | |
| 5,167,610 A | | 12/1992 | Kitado et al. | |
| 5,267,942 A | | 12/1993 | Saperston | |
| 5,304,112 A | * | 4/1994 | Mrklas et al. | 434/236 |
| 5,406,957 A | * | 4/1995 | Tansey | 600/544 |
| 5,441,476 A | | 8/1995 | Kitado et al. | |
| 5,613,498 A | | 3/1997 | Yasushi et al. | |
| 5,667,470 A | | 9/1997 | Janata | |
| 5,694,939 A | * | 12/1997 | Cowings | 128/905 |

FOREIGN PATENT DOCUMENTS

| EP | 0 496 196 A1 | 7/1992 |
| JP | 59-146639 | 8/1984 |
| JP | 59-232380 | 12/1984 |
| JP | 63-99877 | 5/1988 |
| JP | 4-200440 | 7/1992 |
| JP | 4-307071 | 10/1992 |
| JP | 4-348761 | 12/1992 |
| JP | 5-103837 | 4/1993 |
| JP | 5-293173 | 11/1993 |
| WO | WO 89/04191 A | 5/1989 |

* cited by examiner

Primary Examiner—Samuel G. Gilbert

(57) ABSTRACT

In order to enable a user to easily and quickly ascertain his body's state of relaxation, the device is provided with: a physiological information extractor 101 for extracting an indicator expressing physiological state from user Y; a storage member 102 for storing the extracted indicator; a judging member 103 for analyzing the change over time in the stored indicator, and determining whether or not the user's condition has improved toward a state of greater relaxation based on the indicator; and a notifying member 104 for providing notice that the body has moved toward a state of greater relaxation, if the results of the aforementioned determination are affirmative.

4 Claims, 34 Drawing Sheets

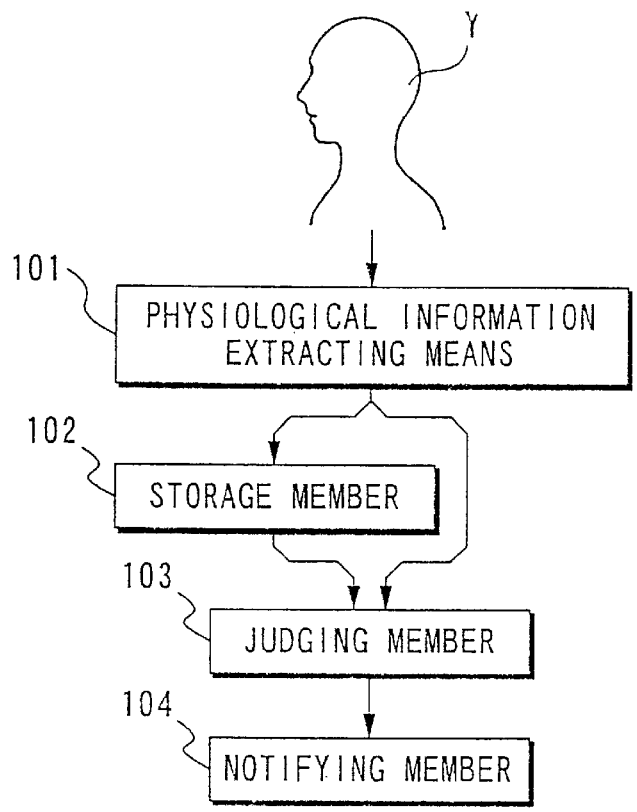
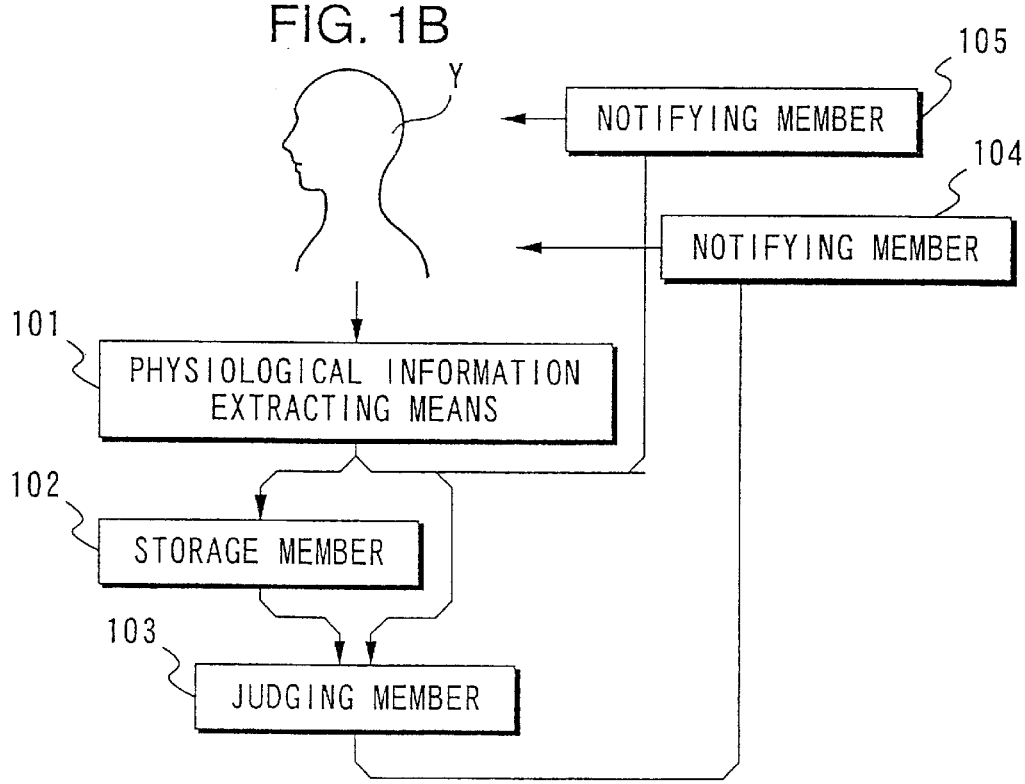

FIG. 5A
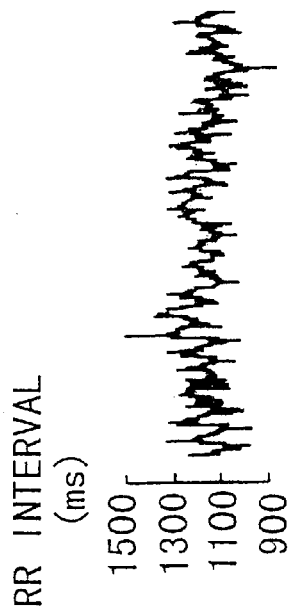
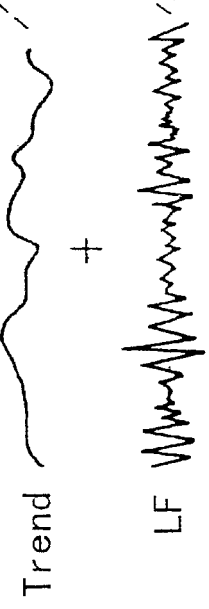
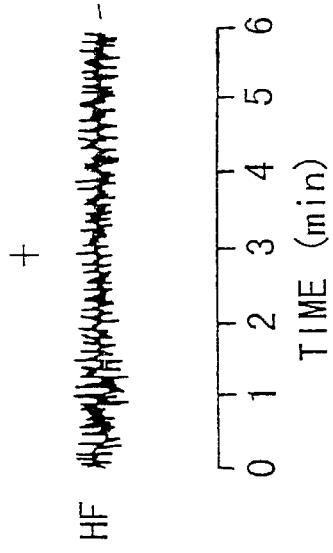
FIG. 5B
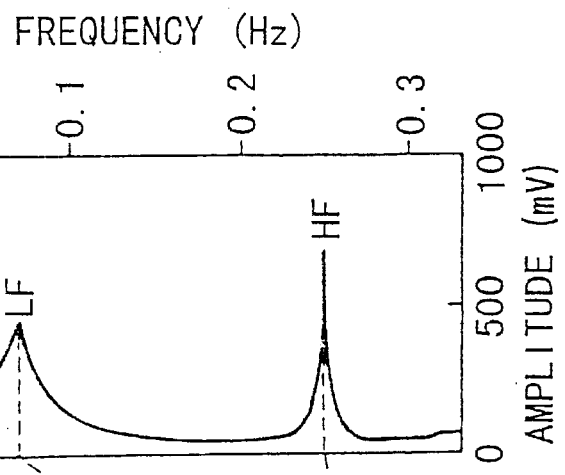

| MULTIPLIER G | GRADE | FACE CHART |
|---|---|---|
| G<1.0 | 0 | 😠 |
| 1.0≦G<1.2 | 1 | 😟 |
| 1.2≦G<1.4 | 2 | 😐 |
| 1.4≦G<1.6 | 3 | 🙂 |
| 1.6≦G | 4 | 😊 |

| EFFECTIVE BIT LENGTH | SHIFT INDICATION QUANTITY | GAIN CONTROL QUANTITY |
|---|---|---|
| 1bit | 6bit | 64× |
| 2bit | 5bit | 32× |
| 3bit | 4bit | 16× |
| 4bit | 3bit | 8× |
| 5bit | 2bit | 4× |
| 6bit | 1bit | 2× |
| 7bit | 0bit | 1× |

$V_1$: AORTIC PRESSURE
$V_p$: RADIUS ARTERY PRESSURE e: LEFT CARDIAC VENTRICULAR PRESSURE
$V_1$: AORTIC PRESSURE
$V_p$: RADIUS ARTERY PRESSURE

| PEAK ADDRESS ADR3 | 0 | 1 | 2 | 3 | 4 |
|---|---|---|---|---|---|
| WAVEFORM VALUE ADDRESS ADR1 | | | | | |
| PEAK TYPE B/T | | | | | |
| WAVEFORM VALUE W | | | | | |
| STROKE STRK | | | | | |
| SLOPE INFORMATION SLP | | | | | |

PEAK INFORMATION {

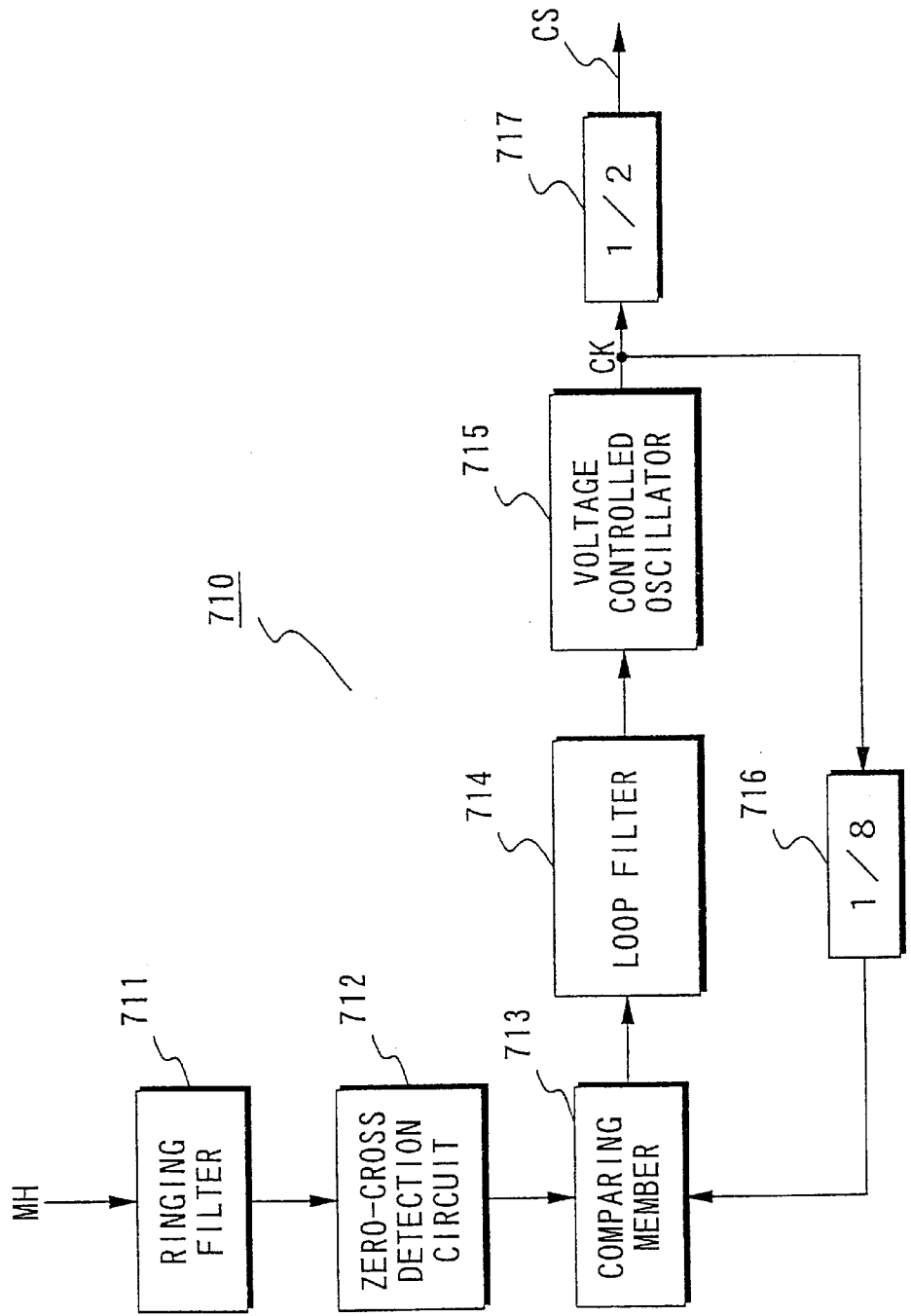

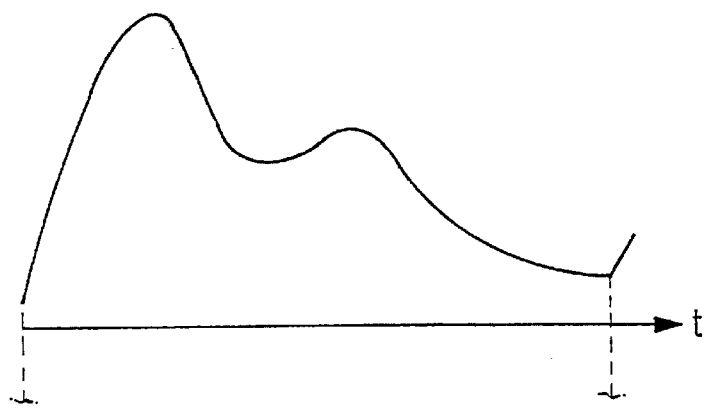
FIG. 40A MH
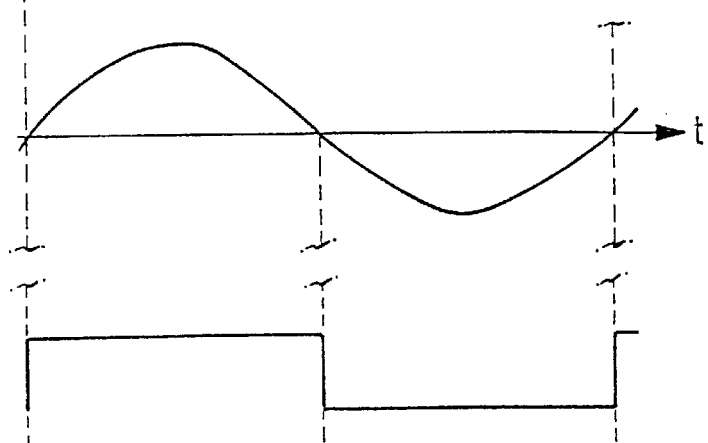
FIG. 40B 711 out
FIG. 40C 712 out
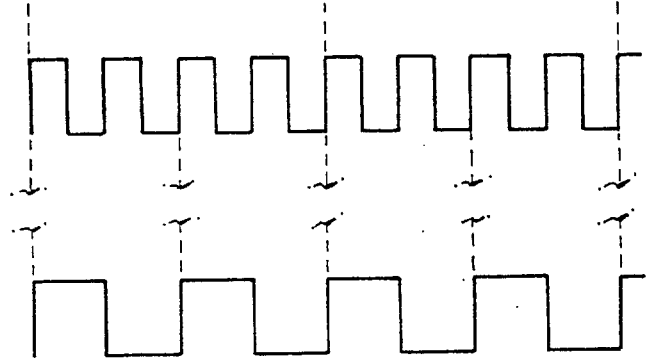
FIG. 40D 715 out CK
FIG. 40E CS

RELAXATION GUIDANCE DEVICE AND BIOFEEDBACK GUIDANCE DEVICE

CROSS REFERENCE TO RELATED APPLICATIONS

This is a Divisional of prior application Ser. No. 09/029,706, filed on Mar. 5, 1998 now abandoned which is a 35 U.S.C. 371 National Phase application of No. PCT/JP97/02278, filed on Jul. 2, 1997, each of which is incorporated herein in its entirety by reference.

TECHNICAL FIELD

The present invention relates to a relaxation guidance device which provides suitable guidance to a user performing relaxation training, and to a biofeedback guidance device which provides suitable guidance to the user when this training is being performed using biofeedback.

BACKGROUND ART

It has been the practice in the past to prescribe tranquilizers, drugs for modulating the autonomic nervous system, vitamins (B1, B12) or the like to patients when providing a pharmacological treatment for autonomic imbalances. In recent years, however, so-called autogenic training methods have come into practice in the treatment of a variety of diseases, including autonomic imbalances (see Practical Autogenic Training, written by Yuji Sasaki, Sogen Publications, or Lecture on Psychotherapy, 3 Practical Autogenic Training, edited by Yuji Sasaki, Nippon-Bunka-Kagaku-Sya Publications).

Developed in Germany prior to 1930, autogenic training methods are closely related to relaxation (psychosomatic relaxation) and hypnosis. In addition to being employed in the treatment of the various illnesses described above, these techniques have been broadly employed to improve concentration in school, as part of employee training in industry, and the like. In terms of clinical efficacy, autogenic training methods have also proved beneficial in the treatment of psychosomatic and anxiety neurosis that effect various organs, these including cardiac neurosis, autonomic imbalances, irritable colon syndrome, and hyperventilation, among others.

Autogenic training consists of six aspects: perception of heaviness in the hands and feet, temperature sensation in the hands and feet, cardiac regulation, respiration, abdominal temperature sensation, and the sensation of coolness over the forehead. By performing this training in a progressive manner, the subject is able to shift into a state of relaxation and low arousal. In the case of training with respect to temperature sensation in the feet and hands, for example, the subject silently repeats to himself "my hands and feet are warm".

This training is not only efficacious in the treatment of the various diseases described above, but also may provide effects such as recovery from accumulated fatigue, reduced hostile behavior through improved self-control, improved efficiency during study or work, relief from physical or psychological pain, an improved sense of self-worth due to greater introspection as a result of the training, and greater psychological concentration. In addition, these techniques can also be applied in so-called "self-suggestion" and other stress-management techniques, to prevent autonomic nervous activity from rising too much. These techniques can be carried out by the user on an occasional basis, for a short period of time such as a minute or two, and may be performed in any location at any time. Moreover, temperature sensation training has an anti-stress effect, so that symptoms due to stress can be reduced.

Other treatment methods including biofeedback, which employs physiological phenomena, have also been used conventionally (see Biofeedback Principles and Practice for Clinicians, edited by John V. Basmajian). In this type of treatment method, the subject (user) is made aware of various physical information such as muscular tension, skin temperature, pulse and the like which are not ordinarily noticed on a conscious level, so that the subject can learn to control these reactions in the body. For example, in a treatment employing muscular tension, muscular activity is detected using an electromyogram, and converted into an audio signal which is played for the user.

Biofeedback provides the following effects which are not obtained from the autogenic training described above. Namely, the subject or a third person who is directing the training is able to ascertain the current condition of the subject's body, i.e., is able to see the increase/decrease in the activity of the subject's electromyogram, in real time. Further, because physiological indicators are measured, it is easy to evaluate the efficacy of training. Further, by notifying the user when an effect beyond that anticipated is obtained, this is expected to serve as encouragement to the user. Moreover, because the target is easily understood, the user is able to experience this training without excessive effort (referred to as passive concentration).

A method employing biofeedback is disclosed in Published Unexamined Japanese Patent Application No. 4-200440, for example. In the technique disclosed in this publication, a target value is set for physiological information, the user's physiological data is measured and compared to this target value, notification is provided of the results of this comparison, and the transition in the results of this comparison is displayed. In the technique disclosed in this publication, the maximum value of the physiological information currently measured can be set as the target value for the next time measurements are made.

In addition, another device which employs biofeedback is disclosed in Published Unexamined Japanese Patent Application No. 59-232380. This device controls training for a plurality of users, and makes it possible to ascertain the progress of the entire group. Namely, the pulse waves of first and second specific frequency components are extracted from a plurality of users, the users are notified in common with respect to the first specific frequency component according to the direction of a trainer (director), and then each user is notified independently with respect to the second specific frequency component.

However, the autogenic training methods described above are problematic in that they do not permit the user to readily understand the body's current status. As a result, where carrying out hands and feet temperature sensation training, for example, it is not possible to determine whether the training is having an actual effect, such that the fingers have actually become warmer. In other words, it is not possible in the least for the user to understand on a quantifiable basis his body's current condition.

Accordingly, even if training is more efficacious than the user anticipated, the user is not informed to this effect, so that such benefits as an increased desire to continue training or a reduced inclination to quit cannot be anticipated in the above-described autogenic training methods. In addition, it is difficult to communicate the concept of passive concentration to a user who is always highly tense. Thus, in the case where training must be carried out over a long period of time, in a step-wise manner, it is possible that the user may not learn muscular relaxation well in the initial stages.

Further, biofeedback also has disadvantages. Namely, the patient or user may too readily become dependent on the device, or it may be difficult for the user to grasp the specific actions which must be carried out in order to achieve a state of relaxation. In the case of a patient who is extremely anxious, muscular relaxation may not produce any effects on the autonomic activity which is the anxiety reaction.

In the technique disclosed in Published Unexamined Japanese Patent Application No. 4-200440, the subject is informed of the results of a comparison between the current physiological information and set target values, as well as the transition in the results of this comparison. However, the results of the comparison depend on the target value settings. Namely, target values differ entirely depending on the person. However, since multiple targets are not provided when setting these values, the significance of the compared results appears dubious. For example, if the target value is set low, then the user may be notified that training is having an effect. Conversely, if the target value is set high, then the user may be informed that training is not producing any effects. Thus, even if the maximum value for the physiological information currently being measured is selected and set as the target value for the upcoming measurement, as is disclosed in this reference, it is only possible to determine whether or not the effects of training at the time of the next measurement have improved versus the current measurement. Thus, it is not possible for the user to know his current physiological state, or how it is changing.

Thus, the technique disclosed in this reference has the same problems as described above in the case of conventional autogenic training.

On the other hand, Published Unexamined Japanese Patent Application No. 59-232380 merely provides notice to the user of his current physiological condition. Evaluation of that condition is entrusted to a director, however, so that the user has no way of knowing.

Accordingly, the technique disclosed in this reference has the same problems as encountered in the case of conventional autogenic training described above.

As may be understood from the preceding discussion, even if the user has made various endeavors to relax, it has not been possible by means of the conventional art for the user to confirm whether or not he has actually entered a state of relaxation, or to ascertain his current physiological status. Moreover, these same types of problems are encountered in the case where biofeedback is employed.

DISCLOSURE OF THE INVENTION

The present invention was conceived in consideration of the aforementioned problems, and has as its first objective the provision of a relaxation guidance device capable of quickly and easily confirming a state of relaxation, as well as providing suitable guidance during relaxation training.

Additionally, the present invention has as its second objective the provision of a biofeedback guidance device capable of quickly and easily confirming the effects obtained when carrying out biofeedback training, as well as providing suitable guidance during that training.

In order to achieve the above-stated first objective, the present invention is firstly characterized in the provision of a first judging means for judging the state of relaxation in the subject's body based on indicators expressing physiological state which are extracted at two or more different points in time from the subject's body; and a first notifying means for providing guidance to the subject with respect to the state of relaxation determined by the first judging means.

In order to achieve the above-stated second objective, the present invention is secondly characterized in the provision of an extracting means for extracting indicators expressing physiological state from the body; a third notifying means for providing notification based on the indicators extracted from the extracting means; a second judging means for determining the physiological state based on the indicators extracted by the extracting means at two or more different points in time; and a fourth notifying means for providing guidance to the subject with respect to the physiological state determined by the second judging means; the body controlling the state expressed by the indicators notified from the third notifying means.

As a result of the first characteristic described above, it is possible for the subject to obtain guidance suitable for shifting into a relaxed state.

As a result of the second characteristic described above, it is possible for the subject to obtain guidance suitable for carrying out autogenic training using biofeedback.

BRIEF DESCRIPTION OF DRAWINGS

FIG. 1A is a block diagram showing the functional structure of the relaxation guidance device according to the first embodiment of the present invention; FIG. 1B is a block diagram showing the functional structure of the relaxation guidance device according to the first embodiment of the present invention.

FIG. 5A shows the relationship between change in the RR interval and the frequency component which composes the change; FIG. 5B shows the results of spectral analysis of change in the RR interval.

FIG. 39 is a block diagram showing the structure of the waveform shaping member in the wavelet converter.

FIGS. 40A through 40E are timing charts showing the operation of the wavelet converter.

BEST MODE FOR CARRYING OUT THE INVENTION

Figure 2:
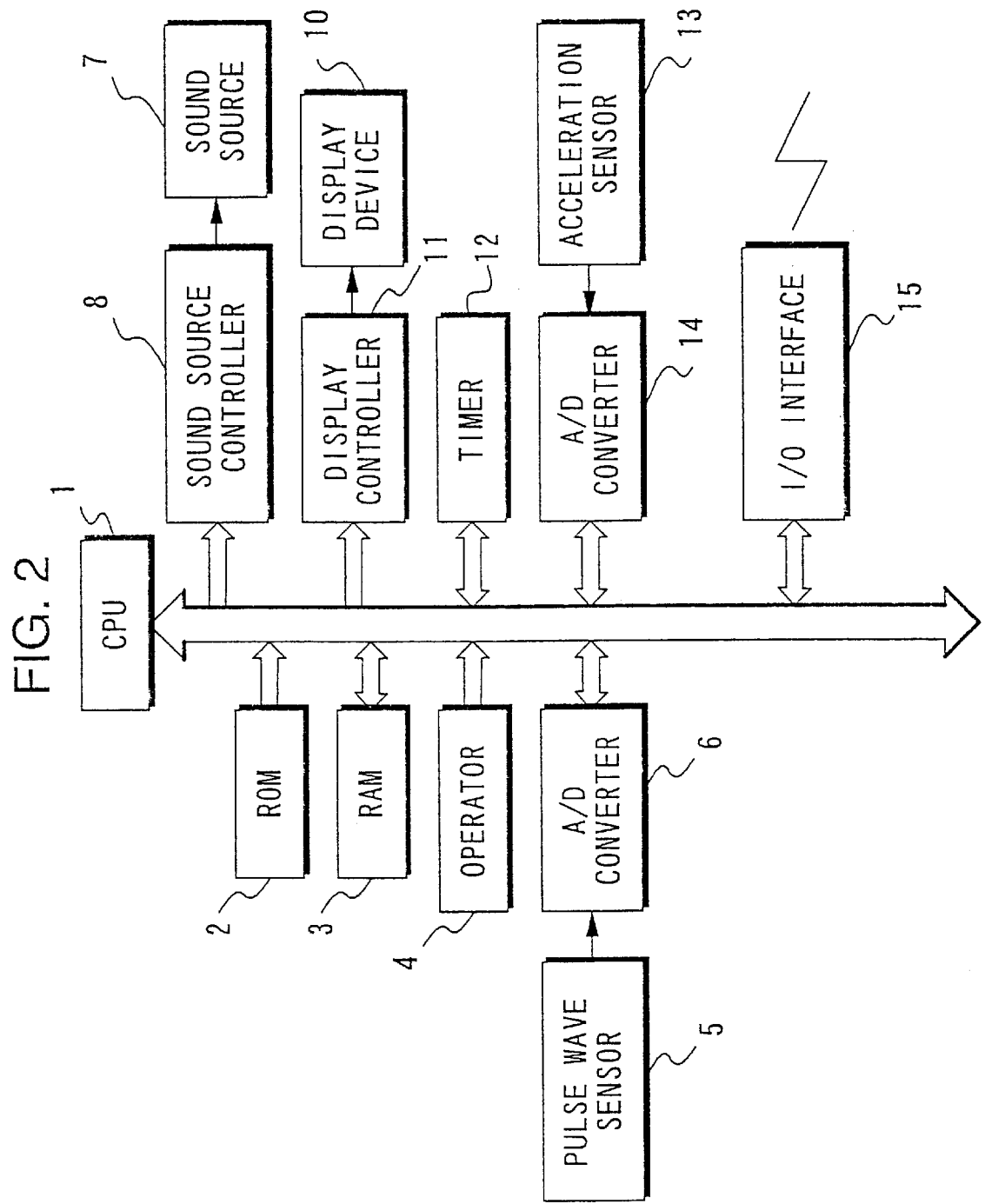
FIG. 2 is a block diagram showing the electrical structure of the relaxation guidance device according to the first embodiment of the present invention.

Preferred embodiments of the present invention will now be explained with reference to the accompanying figures.

<1: First Embodiment>

The relaxation guidance device according to the first embodiment of the present invention will now be explained. FIG. 1A is a schematic diagram showing the functional structure of this device.

In the figure, physiological information extractor 101 extracts an indicator from user Y which expresses his physiological state; storage member 102 time sequentially stores the extracted indicators; judging member 103 compares the current indicator extracted by physiological information extractor 102 with the indicator extracted prior thereto which is stored in storage member 102, and determines whether or not the current indicator represents an improvement in relaxation over the preceding indicator; and notifying member 104 notifies the user of the results of this determination and the degree of relaxation.

<1-1: Extraction of Indicator Expressing Physiological State>

Prior to explaining the preferred embodiments in detail, an explanation will first be made of indicators which express physiological state. For the purpose of convenience, this embodiment will employ the fluctuations (change) in the pulse waveform such as LF, HF, LF/HF and RR50 as these indicators. Of course, the present invention is not limited thereto. Please note that other indicators in addition to the aforementioned will be explained below.

Figure 3:
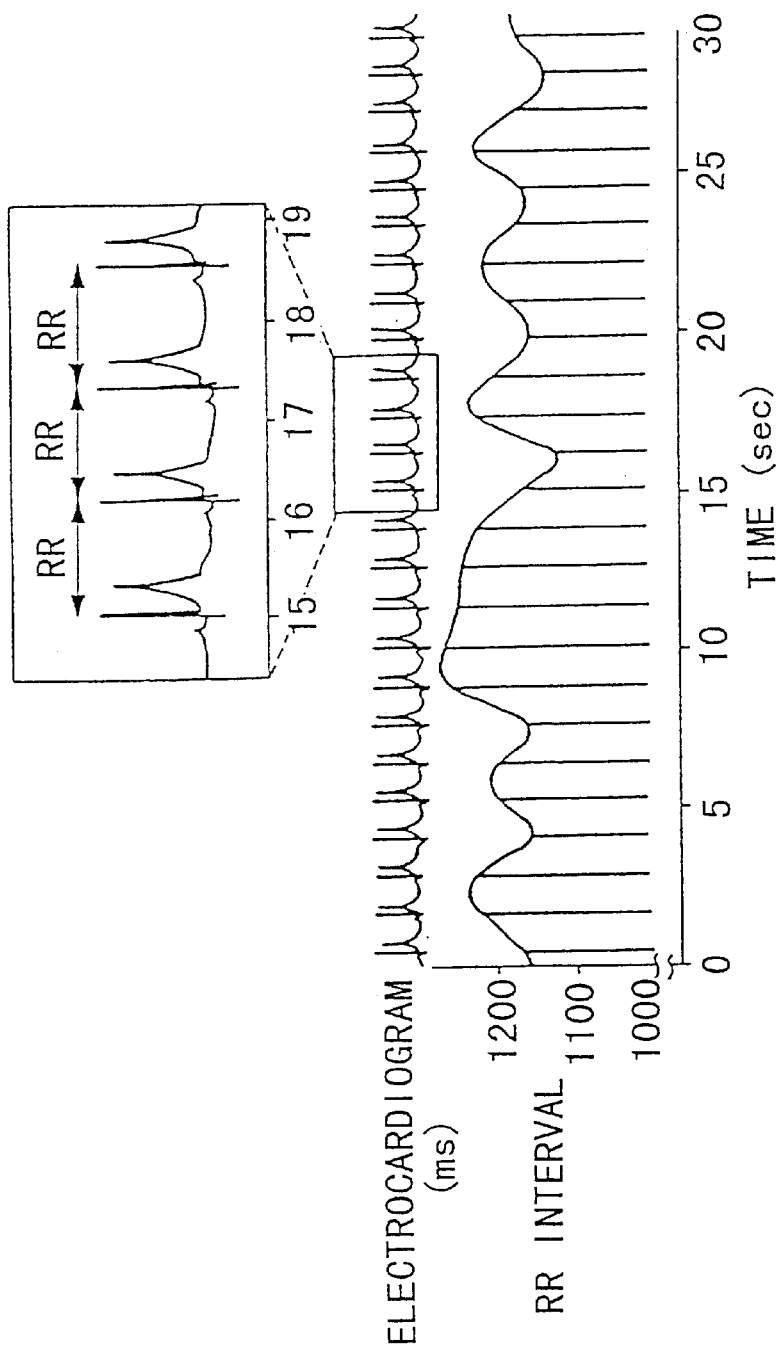
FIG. 3 shows the relationship between the RR interval and the electrocardiogram.

In an electrocardiogram, the interval between the R wave of one heart beat and the R wave of the next heart beat is referred to as the RR interval. This RR interval is a numerical value which serves as an indicator of the functioning of the autonomic nervous system in the human body. That is to say, the RR interval is an indicator which expresses the body's physiological state. FIG. 3 shows heartbeat and the RR interval obtained from the waveform of this heartbeat in an electrocardiogram. As may be understood from this figure, an analysis of the measured results in an electrocardiogram reveals that the RR interval varies over time.

Figure 4:
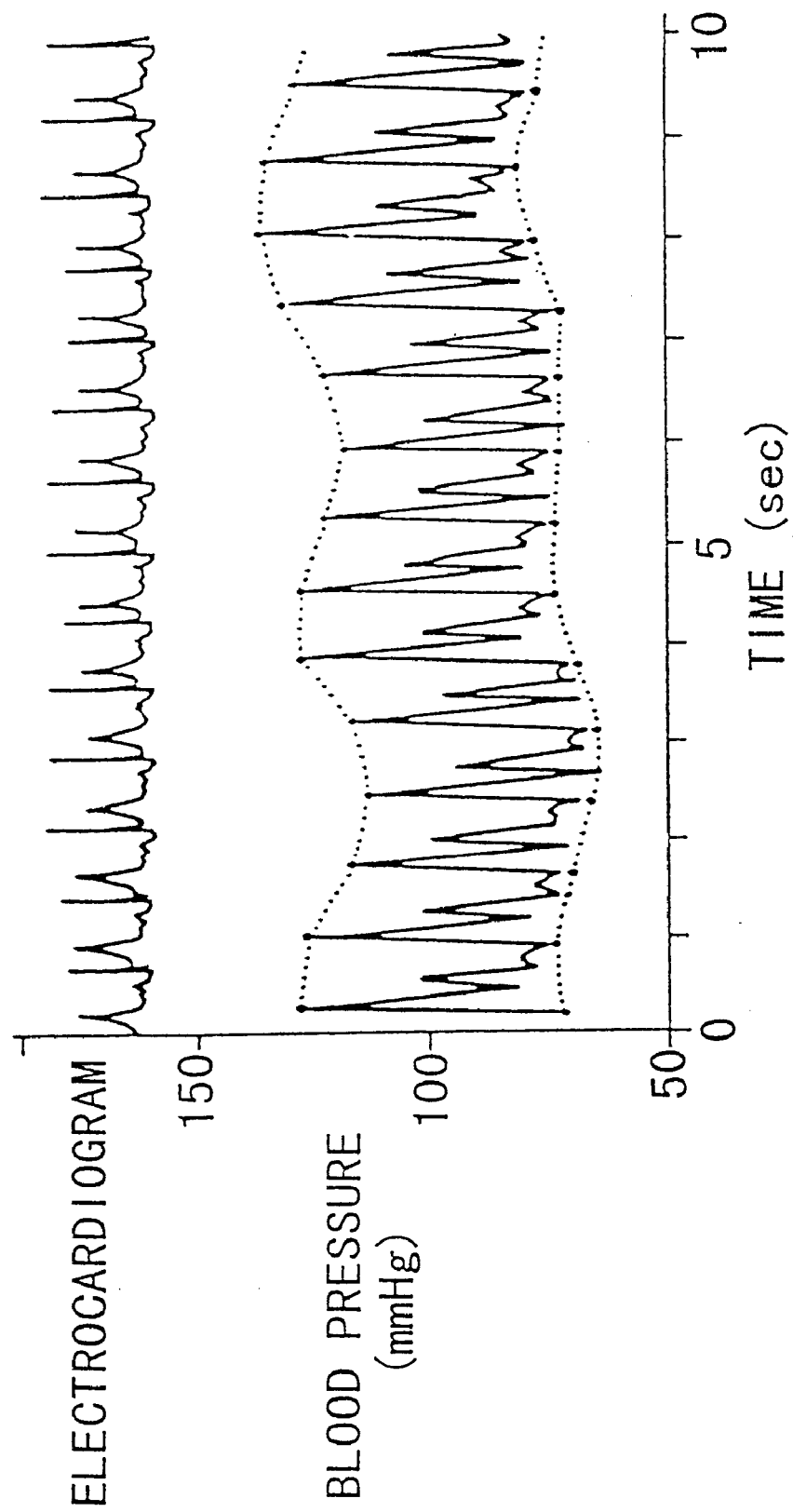
FIG. 4 shows the relationship between an electrocardiogram and the pulse waveform.

On the other hand, variation in blood pressure measured at a peripheral point such as the radius artery or the like, is defined as the variation in blood pressure at each beat from contraction to relaxation of the heart, and corresponds to variation in the RR interval in an electrocardiogram. FIG. 4 shows the relationship between the electrocardiogram and blood pressure. As may be understood from this figure, the blood pressure during each contraction and relaxation in a heart beat can be measured as the maximum value of arterial pressure, and the minimum value immediately preceding this maximum value in each RR interval.

By carrying out spectral analysis of variations in heart beat or blood pressure, it may be understood that the variations are composed of waves having a plurality of frequencies. These may be classified into the following three types of variation components.

1. HF (high frequency) component which is the variation coinciding with respiration
2. LF (low frequency) component which varies with a periodicity of around 10 seconds
3. Trend which varies with a frequency which is lower than the measurement limits.

In order to obtain these components, the RR interval between neighboring pulse waves is obtained for each measured pulse wave, and the discrete value of the obtained RR interval is interpolated using a suitable method. An FFT (fast Fourier transform) operation is carried out on the curved lined after interpolation, followed by spectral analysis. As a result, it is possible to pick out the variation component as a peak on the frequency axis. FIG. 5A shows the waveform of variation in a measured pulse wave interval and the waveform of each of the components of variation in the case where the waveform of variation is segregated into the three frequency components noted above. FIG. 5B shows the results of spectral analysis on the waveform of variation in the pulse wave interval shown in FIG. 5A.

As may be understood from this figure, peaks are apparent at two frequencies near 0.07 Hz and 0.25 Hz. The former frequency value is the LF component, while the latter is the HF component. The trend component cannot be read in the figure because it is below the limit for measurement.

The LF component is related to the activity of the sympathetic nervous system. The larger the amplitude of this component, the greater the increase in tension. On the other hand, the HF component is related to the activity of the parasympathetic nervous system. The larger the amplitude of this component, the more relaxed the state.

The amplitude values for the LF and HF components will vary according to the individual. Accordingly, with this in mind, the proportion LF/HF, which is the ratio of the amplitudes of the LF and HF components, is useful to estimate the subject's state. A large LF/HF value indicates increasing tension, while a small LF/HF indicates increasing relaxation.

RR50 is defined by the number of times which the absolute value of the pulse wave interval corresponding to the RR interval for two consecutive heart beats varies by 50 milliseconds or more, when measurements of pulse wave are carried out over a prespecified period of time (one minute, for example). The larger the value of RR50, the more relaxed the subject is, while the smaller the value of RR50, the more tense the subject is. The RR50 level is less than 10 times per minute in the course of daily activities, and is 30 times per minute during sleep. There is a relationship between RR50 and the state of relaxation of the user. The threshold value for whether or not the subject is relaxed is an RR50 value of about 15 times per minute, with the subject is viewed to be in a relaxed state if the RR50 value is above this level.

Strictly speaking, the "R" of the RR50 signifies the R wave of the heart beat. The peak in the pulse wave corresponds to this R wave. Accordingly, the RR50 may also be referred to as the PP50. For the explanation which follows, however, the more general term RR50 will be employed.

<1-2: Specific Structure of the First Embodiment>

An explanation of the structure for realizing the functional design shown in FIG. 1A will now be made. FIG. 2 is a block diagram showing this structure.

In this figure, CPU (central processing unit) 1 is a circuit which serves to control each part of the device, and corresponds to physiological information extractor 101 and judging member 103 shown in FIG. 1A. The function of CPU 1 will be explained in detail below under the section covering operation.

The control programs carried out by CPU 1 and various control data and the like are stored in ROM (read-only memory) 2. In addition, ROM 2 also stores a number of voice message models for use when guiding the user by voice.

As will be explained below, random access memory RAM 3 stores the pulse wave signal waveform, indicators expressing the degree of relaxation, the time at which the indicators are measured, and the like, and is employed as a counter which counts the number of times that a detection is made that the indicator is increasing with time, at the time of measurement of the indicator. In addition, RAM 3 is employed as an operational area when CPU 1 is carrying out calculations. RAM 3 corresponds to storage member 102 shown in FIG. 1A.

Operator 4 carries out display in accordance with the manipulation of buttons by the user. Operator 4 detects the operation of a button, and relays the type of button manipulated along with an interrupt signal to the bus. The specific functions of the buttons will be discussed below.

Figure 6:
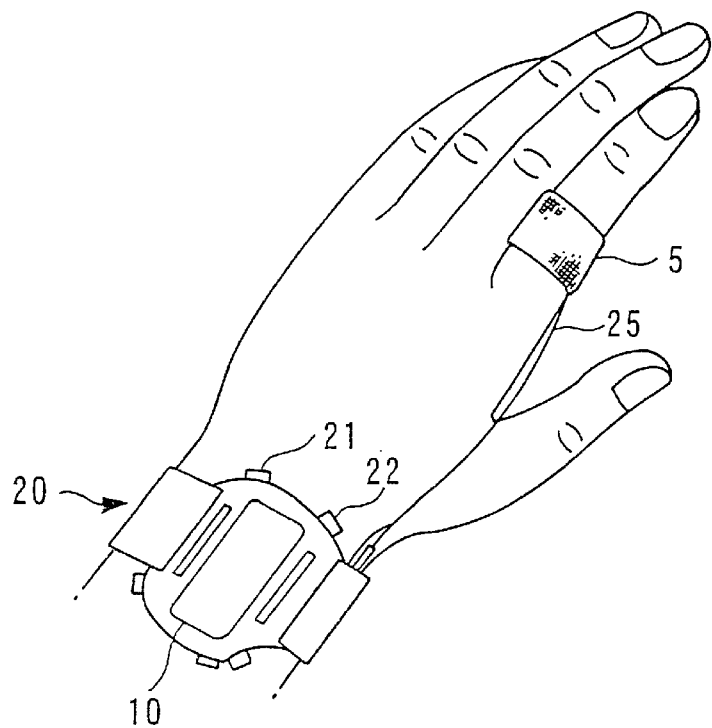
FIG. 6 shows an arrangement wherein the aforementioned device is combined with a wristwatch, and a pulse wave sensor is attached to the base of the user's finger.

Pulse wave sensor 5 is an optical sensor which is attached to the user's finger, for example. This pulse wave sensor 5 is composed of a light emitting diode and a light sensor employing a photo transistor or the like, for example, such as shown in FIG. 6. In this design, light emitted from the light emitting diode is received by the light sensor after being reflected via the blood vessels in the fingertip, for example, and undergoes photoelectric conversion, to obtain a pulse wave detection signal as a result. When taking into consideration the signal noise ratio, it is acceptable to employ a diode which emits blue light.

A/D (analog/digital) converter 6 samples and converts the pulse wave signal detected by pulse wave sensor 5 into a digital signal, and outputs this result to the bus.

Sound source 7 is formed of a speaker or the like, and provides various notices to the user which rely on the physical senses. A variety of arrangements such as described below may be considered with respect to the form of notification. Accordingly, sound source 7 merely represents one example of a notifying means.

Sound source controller 8 is a drive circuit for generating a specific alarm or voice message which CPU 1 reads out from ROM 2. Display 10 is for displaying various messages or graphs together with display information formed by CPU 1. Accordingly, sound source 7 and display device 10 correspond to notifying member 104 shown in FIG. 1A. Display control circuit 11 takes up display information from CPU 1, converts it to a format suitable for display device 10, and controls the display of display device 10.

Timer 12 is provided with ordinary time-keeping functions. The output thereof is employed as the measured clock time when measuring data. In addition, however, timer 12 also sends an interrupt signal via the bus to CPU 1 at clock times which have been preset by CPU 1, or after the elapse of a time period which has been preset by CPU 1. In this case, information is also provided as to whether the interrupt signal is due to the former or latter type of presetting in CPU 1.

Acceleration sensor 13 is a body movement detection sensor which senses movement of the user's body, and is employed in order to confirm whether or not the user's body is moving.

A/D converter 14 converts the analog signal output by acceleration sensor 13 to a digital signal, and then outputs this signal to the bus.

I/O interface 15 is a communication means for sending and receiving various types of information with an external piece of equipment such as a personal computer. As will be explained below, it is attached to an LED or photo transistor. The information sent includes the results of various measurements conducted by the device, target values for autogenic training which are sent from the external equipment to the device of the present invention, and the like. A more detailed explanation of this information as well as a specific example of the arrangement for connection to the personal computer will follow below.

<1-3: Outer Structure of the First Embodiment>

Next, the outer structure of the relaxation guidance device according to this arrangement will be explained. Since it is necessary to continuously measure the user's physiological information, it is preferable that this device have a structure which can be comfortably worn by the user on a daily basis, such as a portable device or accessory. While a variety of designs are possible, the example offered here is of a device which incorporates some of the functions of a wristwatch, as shown in FIGS. 6 through 9. Other arrangements will be discussed below. Note that those parts shown in the aforementioned figures which are common to FIG. 2 have been denoted with the same numeric symbol.

FIG. 6 shows a first arrangement in which this device is incorporated into a wristwatch. In this figure buttons 21,22 are provided to the respective sides of the body of wristwatch 20, and form a portion of operator 4 shown in FIG. 2.

Button 21 is depressed by the user to alternately begin or end measurement of the state of relaxation. Button 22 is for switching between the various modes of the device, one example being the communication mode for sending and receiving the results of various measurements to and from the external device via I/O interface 15.

Cable 25 electrically connects the pulse wave sensor 5 provided inside wristwatch 20 with A/D converter 6.

Figure 7:
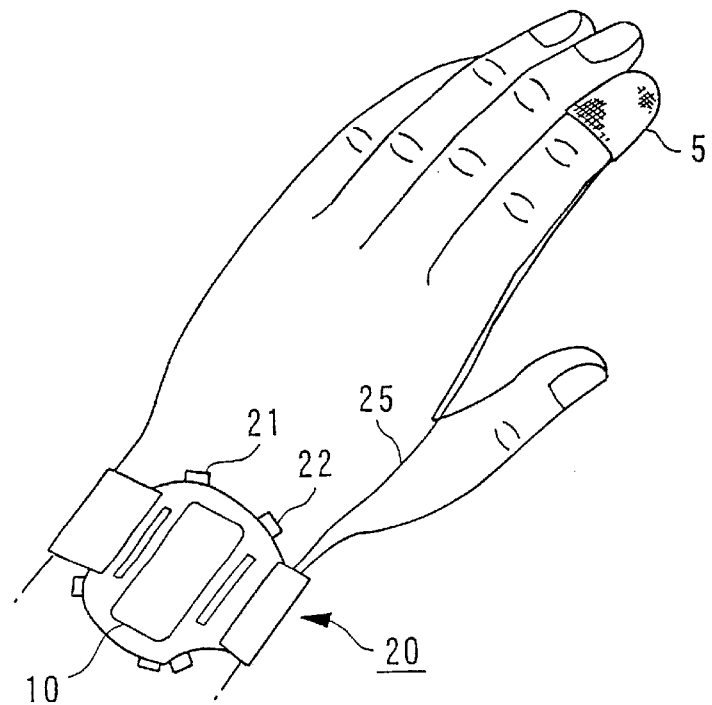
FIG. 7 shows an arrangement wherein the aforementioned device is combined with a wristwatch, and the pulse wave sensor is attached to the fingertip.

FIG. 7 shows a second arrangement in which this device is incorporated into a wristwatch. As shown in the figure, in this arrangement, a pulse wave sensor 5 is attached to the fingertip and measures the fingertip plethysmogram. In addition to the optical means described above, a pressure pulse wave sensor may also be considered as a means for detecting the fingertip plethysmogram.

Figure 8:
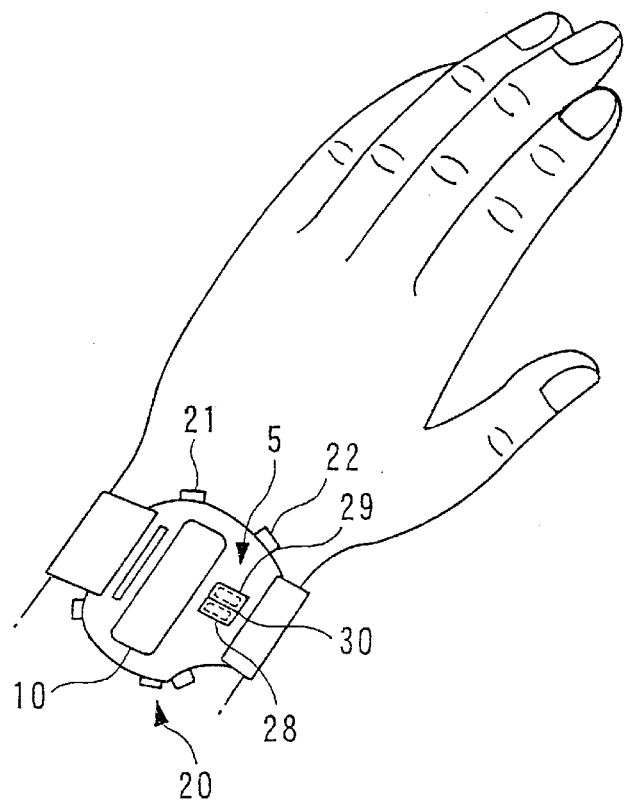
FIG. 8 shows an arrangement wherein the aforementioned device is combined with a wristwatch, and a pulse wave sensor is in contact with the subject's radius artery.

FIG. 8 shows a third arrangement incorporating this device into a wristwatch. As shown in the figure, in this arrangement, pulse wave sensor 5 is formed to the surface of wristwatch 20. In this arrangement, pulse wave sensor 5 consisting of a photo emitting diode 28 and a photo transistor 29 are provided in the 6 o'clock direction of display device 10. Light emitting diode 28 and photo transistor 29 are embedded in the device so that only the head portions thereof are visible from the outside.

In this third arrangement, a partition 30 is provided between light emitting diode 28 and photo transistor 29 so that light released by photo emitting diode 28 is not directly received at photo transistor 29. Note that the principles behind measuring the pulse in this arrangement are the same as in the first and second arrangements. However, when conducting measurements in this arrangement, it is necessary to exercise care with respect to covering both light emitting diode 28 and photo transistor 29 with the tip of a finger on the hand which is not wearing the wristwatch.

Figure 9:
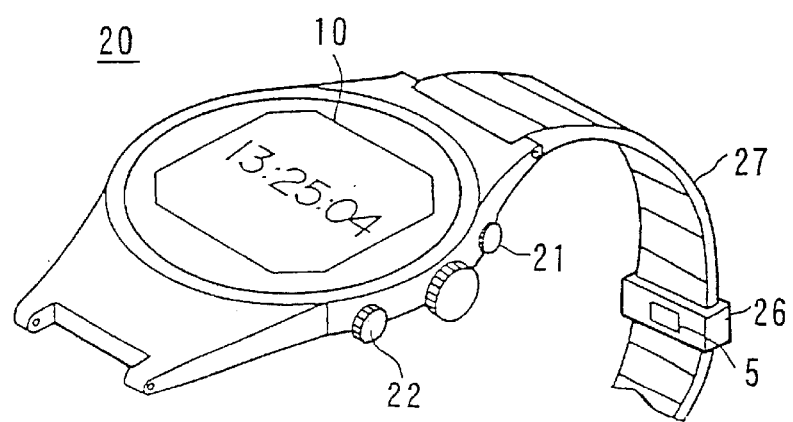
FIG. 9 shows an arrangement wherein the aforementioned device is combined with a wristwatch, and a pulse wave sensor is provided to the surface of a wristwatch.

FIG. 9 shows a fourth arrangement in which this device is incorporated in a wristwatch. As shown in this figure, the pulse wave is detected at the radius artery in this arrangement. Pulse wave sensor 5 is formed of a pressure-type sensor, such as a distortion gauge. Pulse wave sensor 5 is attached to the surface of fastener 26, which is attached in a sliding manner to watch band 27. When wristwatch 20 is worn on the wrist, pulse wave sensor 5 is pressed against the radius artery with a suitable pressure. A pulse wave signal expressing the waveform of the radius artery is obtained from the terminals (not shown) provided to both ends of pulse wave sensor 5. This pulse wave signal is sent to A/D converter 6 housed inside the main body of wristwatch 20 via a signal line (not shown) embedded in watch band 27.

Accordingly, as described above, a variety of arrangements may be considered in which this device is incorporated into a wristwatch. Embodiments other than those involving a wristwatch will now be explained.

<1-4: Structure of External Device>

Next, the external device for sending and receiving information with the relaxation guidance device according to this embodiment will be explained with reference to FIG. 10. As shown in FIG. 10B, the external device is composed of a device main body 50, display 51, key board 52, printer 53, and the like. With the exception of the following points, it is equivalent to an ordinary personal computer.

Namely, device main body 50 internally houses a transmission controller and a receiving controller, which are not shown in the figures, for sending and receiving data by means of optical signals. The transmission controller is provided with LED 54 for sending optical signals, and the receiving controller is provided with a photo transistor 55 for receiving optical signals. LED 54 and photo transistor 55 both employ a device using near infrared (having a central wavelength of 940 nm, for example). LED 54 and photo transistor 55 carry out optical communications via a transmission window 57 for optical communications which is provided to the front of device main body 50, via a visible light cutting filter 56 for blocking visible light.

Figure 10A:
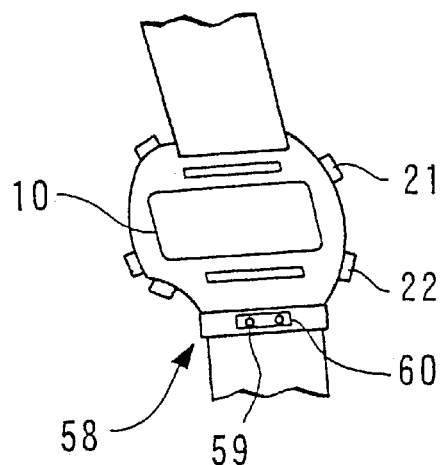
FIG. 10A shows a wristwatch in which the aforementioned device has been incorporated.
Figure 10B:
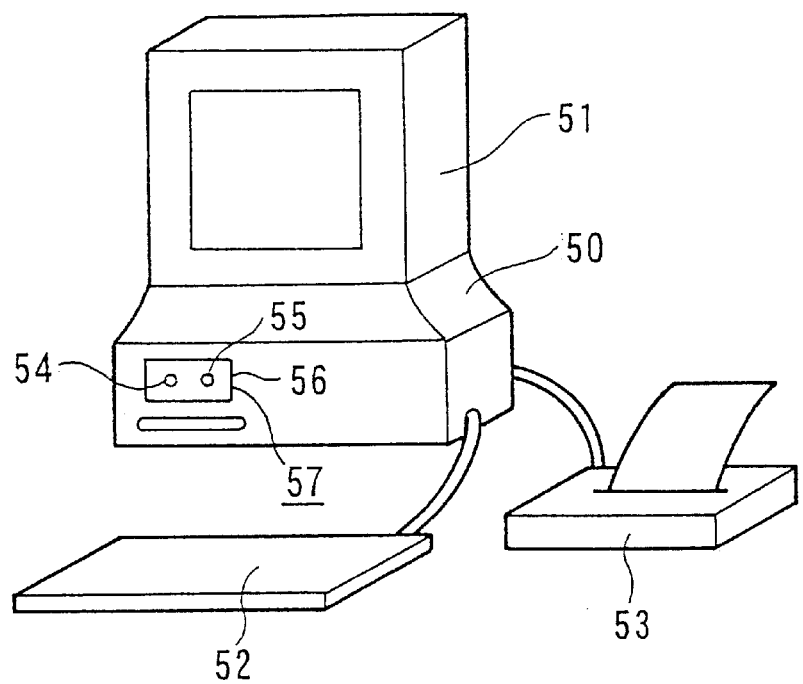
FIG. 10B shows the external device for carrying out optical communications with the aforementioned device.

As shown in FIG. 10A a communications connector 58 for communicating with an external device is attached in a freely releasable manner in the 6 o'clock direction of wristwatch 20, which is equivalent to the relaxation guidance device in this embodiment. In this case, when communication with the external device is not being carried out, communications connector 58 is removed, and a connector cover (not shown) of a roughly equivalent shape is attached. As in the case of the personal computer, LED 59, photo transistor 60 and an interface circuit (not shown) for optical communications are incorporated into communications connector 58, these making up I/O interface 15 shown in FIG. 2.

When carrying out optical communications as described above, if it is not possible to identify which device generated the information, then it is possible that information which is to be received by one device may be mistakenly transmitted to another device. Therefore, when the interface circuit (not shown) for optical communications and the optical interface provided inside the personal computer send or receive information, recognition information is employed to indicate which device sent the information. Accordingly, transmitter 70 shown in FIG. 11 is provided within the personal computer and the interface circuit (not shown) for optical communications.

Figure 11:
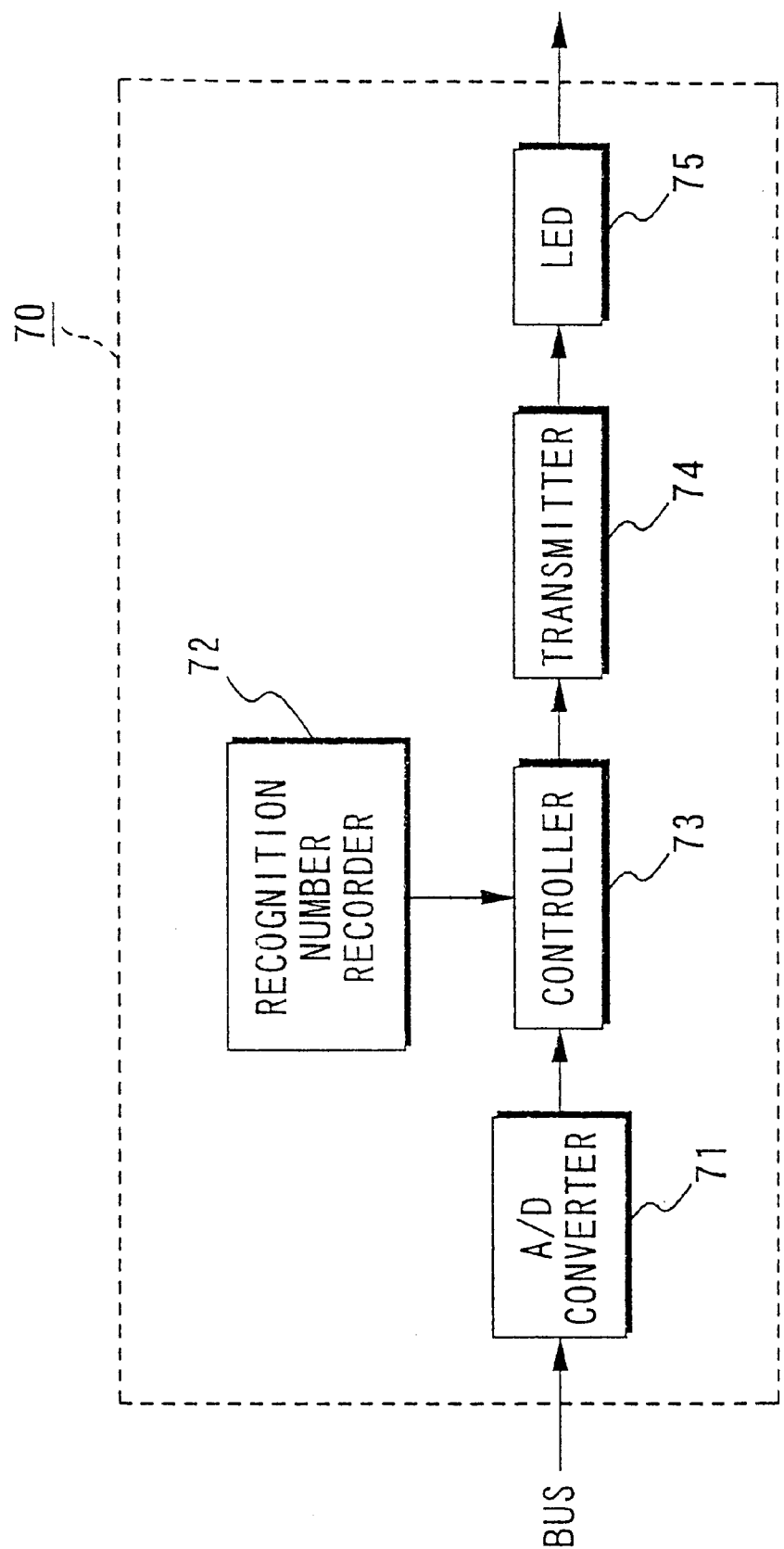
FIG. 11 is a block diagram showing the structure of the transmitters in the aforementioned device and the external device.

In FIG. 11, a variety of communication information sent from the microprocessor in CPU 1 or the personal computer is loaded in the bus shown in the figure. A/D converter 71 samples and converts the information sent from the bus into digital signals at fixed time intervals. Recognition number recorder 72 records the recognition number for recognizing which device sent the optical signal. When the information is sent outside the device, this recognition number is included in the optical signal together with the aforementioned information. Since the recognition numbers recorded in the recognition number recorders 72 of each device differ depending on the settings at the time of shipment of the devices, a unique number is assigned to all of the devices, such as the wristwatch main body, personal computer and the like.

Controller 73 is a circuit for controlling all parts inside transmitter 70. Transmitter 74 houses a drive circuit for driving LED 75 which relays the optical signal. By driving LED 75, transmission data formed by controller 73 is sent to the outside after conversion to an optical signal.

In reality, it is acceptable to use a wire to connect the device of the present invention and the external device, or to carry out wireless communications using radio or optical communications as described above.

<1-5: Operation of the First Embodiment>

Next, the operation of a relaxation guidance device having the above-described structure will now be explained.

Pulse wave sensor 5 begins to uptake the pulse wave when the device's power source is switched on. The pulse wave signal obtained is converted to a digital signal by A/D converter 6, and output to the bus.

Thereafter, when the user depresses button 21 which is provided on wristwatch 20, the device begins measurements for determining the user's state of relaxation. Meanwhile, the user carries out "relaxation training" as autogenic training in order to obtain a state of relaxation.

The simplest method of relaxation training which may be employed here is for the user to remain quiet in his current position with his eyes closed. Other methods such as those described below may also be considered, however.

First, the user should move to a location where he can be alone if possible. The user should then assume a position which is comfortable and which will incur as little movement as possible, and remain with his eyes closed gently. With his eyes closed, the user may take note of and remove a wristwatch or any accessories in contact with the body which are distracting. In order to even further enhance the efficacy of the relaxation training, it is preferable that the user be seated in a chair or lying on a bed.

Second, if the first method described above does not produce any effects, then the user may quietly chant a predetermined key word, while keeping his eyes shut. This key word should be one which has positive connotations, and promotes images such as "happiness", "peace", "love", or "kindness". Other acceptable examples of key words include the name of a favored object, number, or person, or a line from a favorite poem or sutra. The length of the key word preferably matches the length of expiration and is formed of 3 to 4 sounds.

Third, the user may also consider listening to α-wave music, classic, Baroque, or music demonstrating a 1/f fluctuation. In this case, it is also acceptable to employ a body sonic as well.

Fourth, the user may also try envisioning a color which is suitable for relaxation. In this case, cool colors are preferred to warm colors, with sky-blue, blue-green, green, and yellow-green being desirable.

Fifth, the user may use scents which facilitate relaxation. Scents such as sandalwood, rose, chamomile, rosemary and the like are preferred. In this case, it is acceptable to provide a device for emitting fragrant essential oils, so the user is directly misted with these oils.

Sixth, the user may view a picture or pattern which has a 1/f fluctuation component.

On the other hand, operator 4 detects when the user depresses button 21 of wristwatch 20, and reports an interrupt to CPU 1. As a result, CPU 1 recognizes the start of measurements, sets timer 12 to generate an interrupt at fixed time intervals and to generate a separate interrupt upon the elapse of a fixed period of time. The former time duration is the time interval for measuring indicators which express physiological state. In contrast, the latter time duration is the time interval until measurements are ended, and is the time duration until the user is notified that he has not reached a sufficiently relaxed state even after considerable efforts. In this embodiment, this time duration is between 3 to 5 minutes.

Next, when an interrupt is reported from timer 12 during the fixed time interval, CPU 1 stores the pulse wave signal in RAM 3 for a given time duration, and then calculates each indicator of physiological state based on the stored pulse wave signal. Namely, in order to extract the maximum points from the waveform of the pulse wave, CPU 1 first takes the time derivative of the pulse waveform, and determines all clock times at which there is a point of inflection in the waveform by determining the clock times at which the time derivative is zero. Next, CPU 1 decides whether each inflection point is a maximum or minimum from the slope (i.e., value of the time derivative) of the waveform around the inflection point. For example, with respect to a given inflection point, CPU 1 calculates the moving average of the slope of the waveform for a specific time part preceding the inflection point. If this moving average is positive, then the inflection point is a maximum, while if it is negative, the inflection point is a minimum.

Next, CPU 1 determines the minimum points immediately preceding each of the extracted maximum points. The pulse wave amplitudes at the maximum and minimum points are read out from RAM 3, and the difference between them is determined. If this difference exceeds a prespecified value, then the clock time of that maximum point is designated as a peak in the pulse wave. After carrying out this peak detection processing on all the pulse waveforms taken up, the time interval between two adjacent pulse wave peaks (corresponding to the RR interval between heartbeats) is calculated based on the clock time at which these peaks occur.

CPU 1 sequentially determines time difference in neighboring pulse wave intervals from the obtained pulse wave intervals. Next, a check is made of each of these time differences to confirm whether or not the time difference exceeds 50 milliseconds, and the fixed number of time differences exceeding 50 milliseconds is counted and set as RR50.

In the case where employing LF and HF components as indicators expressing physiological state, then, because the value of the obtained pulse wave interval is discrete along the time axis, a curved line such as shown in FIG. 5A is obtained by interpolation between neighboring RR intervals. Next, a spectrum such as shown in FIG. 5B is obtained by carrying out FFT processing on the interpolated curved line. Then, in the same manner as performed on the pulse waveform, peak discrimination is employed to determine the maximum values and the frequencies in the spectrum corresponding to the aforementioned maximum values. The maximum value obtained in the low frequency region is defined as the LF component, while the maximum value obtained in the high frequency region is defined as the HF component. Further, the amplitudes of these components are obtained and the amplitude ratio LF/HF is calculated.

Each of the indicators are calculated in this way. However all of these indicators are not essential for determining the state of relaxation in the body. The following explanation will employ the RR50 as the indicator.

CPU 1 store the calculated RR50 value in RAM 3 in association with the current measured clock time read out from timer 12. If the stored RR50 is not the first RR50 obtained after the user depressed button 21, then CPU 1 compares whether or not the current RR50 is increasing versus the RR50 calculated at the immediately preceding measurement (i.e., CPU 1 determines whether or not the user is moving into a state of greater relaxation). If the current RR50 is found to have increased, then CPU 1 informs the user to that effect. Since the user has his eyes closed at this point to facilitate relaxation, it is necessary to provide some means not dependent on sight to alert the user in this case. Accordingly, via a sound source 7, CPU 1 may play a melody which does not interfere with the user's relaxation training.

In addition, CPU 1 determines whether or not the user is in a sufficiently relaxed state. The reason for this determination is that there is believed to be a fixed limit for the state of relaxation. Namely, once the user is sufficiently relaxed, there is no further improvement in relaxation beyond this point, and the change in the RR50 value becomes saturated. To state conversely, if this saturation state is reached, then the user may be said to have reached a sufficiently relaxed state.

Figure 12:
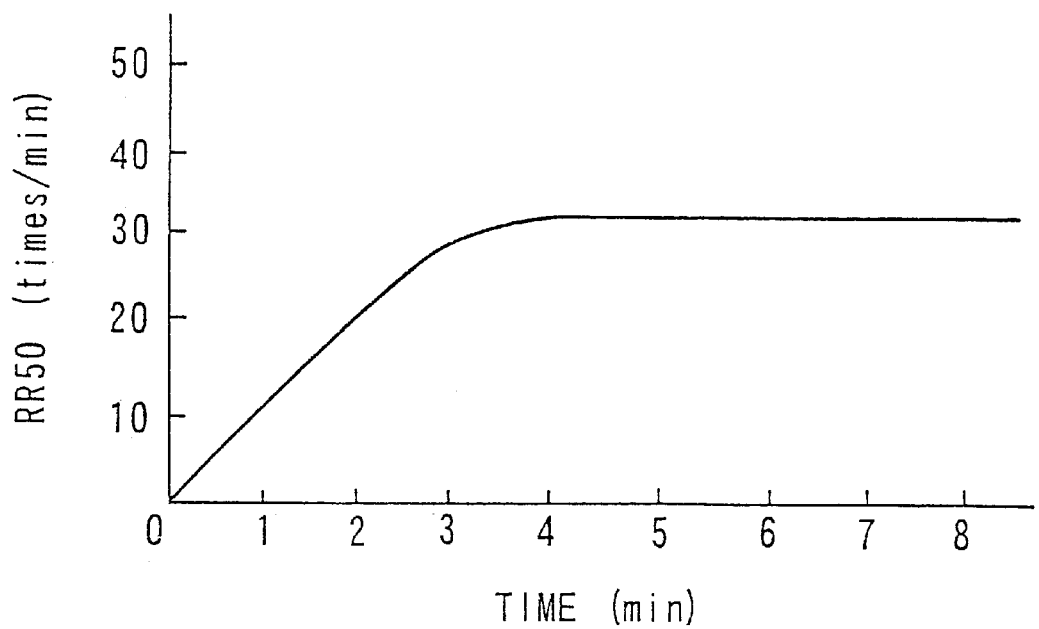
FIG. 12 is a graph showing the change in the RR50 value as the state of relaxation progresses as a result of training.

In FIG. 12, the RR50 value increases as the user continues training, and shows a state of saturation. The graph in this figure is based on experimental results obtained for 60 test subjects. In the figure, the horizontal axis represents elapsed time from the start of training, while the vertical axis is the RR50 value at one minute time intervals. From the figure, the RR50 value reaches 15 times/minute 1 minute and 30 seconds after training begins, with the user viewed to be in a relaxed state in this range. The RR50 is saturated about 4 minutes after training begins.

In order to detect this state of saturation, CPU 1 compares the current RR50 value at each time of measurement with the RR50 measured during the preceding measurement and determines whether or not the current RR50 value has increased. If the current RR50 value has increased, then CPU 1 increases a counter proved to RAM 3 by +1, and checks whether or not the new counter value exceeds a specific value. This procedure is carried out in order to avoid an incorrect determination that the user is in a relaxed state merely because the RR50 value has ceased to change, even if the user's state of relaxation has not improved hardly at all from the time measurement began. In this case, if the counter value is below a specific value, then CPU 1 does not carry out a check of the saturation state of the RR50, and waits for the report of an interrupt at a specific time interval from timer 12.

In contrast, if the counter value has exceeded a specific value, then CPU 1 reads out the RR50 values calculated during a specific time in the past from RAM 3, and checks whether or not the change in the RR50 value is within a specific range.

Note that the specific value referred to here is the threshold value for determining the state of relaxation, and is set according to the indicator employed. For example, if RR50 is employed as the indicator, then the threshold value is 15 times/minute. Further, the specific range cited here is the standard for determining whether or not the indicator is in a state of saturation. Similarly, the specific range is set according to the indicator. When taking into consideration measurement error, the RR50 is viewed to be in a state of saturation when the change in the current calculated value versus a past calculated value is in the range of −10% to +10%.

In the determination of this type of change, a value outside the specified range indicates that the user is not sufficiently relaxed. Thus, as in the case when the counter value has not exceeded a specific value, CPU 1 again waits for an interrupt from timer 12. In this way, when the state of relaxation is insufficient, the above operations are repeatedly carried out.

In contrast, if the RR50 value is within the specific range, then the user is notified that he is in a sufficiently relaxed state. Since the user's eyes are closed in this case, the user may be notified of this fact by means of a melody which differs from that employed in the case where informing the user of his transition to a relaxed state. Meanwhile, CPU 1 releases the settings in timer 12, and concludes measurements.

Thereafter, when the user depresses button 21, CPU 1 quantifies the improvement in the degree of relaxation based on the measurements just executed, and notifies the user of the degree of relaxation.

The following methods may be considered for calculating the degree of relaxation. Namely, a method may be employed based on the rate of change in the current value of the indicator versus the indicator's daily value. In this case, RR50 values are obtained at respective measurement start times over a specific interval of time in the past, and stored in RAM 3 in an area separate from the area where the RR50 value being calculated during measurement is stored. The average value of these RR50 values which have been stored over a specific interval of time in the past is calculated, and defined as the user's daily RR50 value. In this case, the last RR50 value obtained during the current measurement is compared to this average value, and the multiple of increase or decrease (multiplying factor) is viewed to be the user's degree of relaxation. From this perspective, then, it is therefore desirable that measurements be performed on a daily basis.

Figure 13:
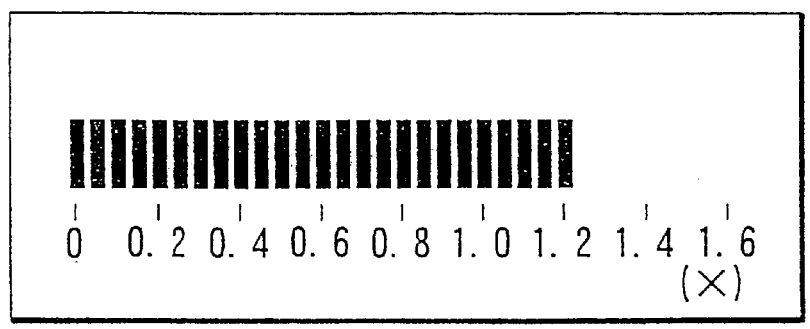
FIG. 13 shows an example of the display in the aforementioned device.
Figures 14, 15:
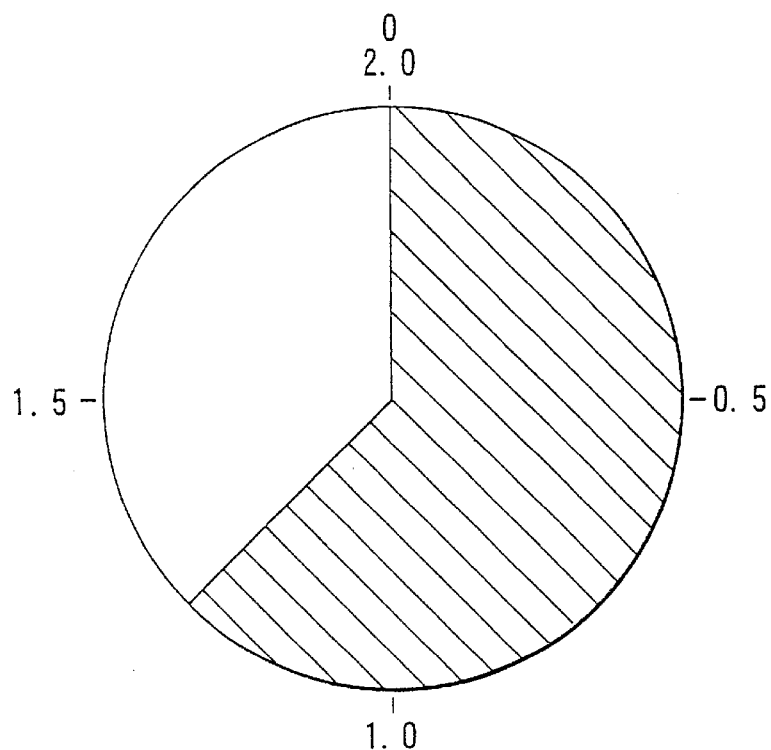
FIG. 14 shows an example of the display in the aforementioned device.
FIG. 15 shows an example of the display in the aforementioned device.

However, it may be difficult for the user to directly grasp the significance of this multiplying factor even when he is informed by means of a bar graph such as shown in FIG. 13 or a pie chart as in FIG. 14. Accordingly, the user may be informed of the multiplying factor for the degree of relaxation after assigning a grade, such as shown in FIG. 15. Namely, if the multiplying factor G is less than 1.0, then a grade of "0" is assigned. If the multiplying factor G is equal to or greater than 1.0 but less than 1.2, then a grade of "1" is assigned. If multiplying factor G is equal to or greater than 1.2 but less than 1.4, then a grade of "2" is assigned. If multiplying factor G is equal to or greater than 1.4 but less than 1.6, then a grade of "3" is assigned. If multiplying factor G is equal to or greater than 1.6, then a grade of "4" is assigned. In other words, the larger the grade, the greater the degree of relaxation. Additionally, if a face chart corresponding to these grades is employed using display device 10, then the user can directly grasp his degree of relaxation.

It is also acceptable to notify the user of details regarding the multiplying factor or the grade value. For example, if the grade value is "0", then the user may be provided with a message such as "no improvement in degree of relaxation", while if the grade value is "1", the user may be provided a message such as "slight improvement in degree of relaxation". Similarly, the user would receive a message such as "improvement in degree of relaxation" in the case of a grade value of "2", and a message such as "significant improvement in state of relaxation" in the case of a grade value of "3". Finally, in the case of a grade value of "4", the user would receive a message such as "very large improvement in degree of relaxation".

Since the user is able to immediately confirm the effects of the current training as a result of this notification, the training takes on significance for the user and contributes to a desire to continue.

Note that the grade assignment in FIG. 15 is offered merely as an example.

The following may be considered as a method for evaluating the effect of training. Namely, evaluation may be based on the degree of change in the indicator just calculated versus a target value set in advance. For this reason, target values are set in RAM 3 by means of the external device (see FIG. 10B), buttons 21,22 or the like. When an external device is used to set the target values, then the setting information for the target values which are input at key board 52 are emitted to the outside as near infrared light via LED 54, and sent to the I/O interface 15 shown in FIG. 2 via photo transistor 60 on wristwatch 20. The information is then stored by CPU 1 in RAM 3. In the case where settings are accomplished using buttons 21,22, then CPU 1 directly stores the values indicated by operator 4 in RAM 3.

Once measurements are completed, CPU 1 compares the obtained rate of change with the preset target values, and notifies the user in response to the results of this comparison. A variety of arrangements may be considered for the results of this comparison. For example, a design is preferable in which the multiplying factor with respect to the target value for the rate of change is assigned a grade such as shown in FIG. 15, and the user is notified in response to this value. A multiplying factor which is less than 1.0 signifies that the current rate of change has not reached the target value. Thus, the user is provided with a message such as "target value not obtained", and prompted to continue further training.

As a result of notification in this way, it is possible to quantitatively evaluate the effect of the current training with respect to the target value. Again, note that the grade assignment shown in FIG. 15 is merely intended as an example.

On the other hand, timer 12 produces an interrupt once the preset shut-off time has elapsed, because achievement of a suitably relaxed state cannot be anticipated at this point, even if the user continues relaxation training. CPU 1 notifies the user that measurements have been shut-off, and releases the settings in timer 12 so that measurements are automatically terminated. After receiving this notice, the user may initiate measurements again after waiting for a short period of time.

As a result of carrying out relaxation training in this way, the user is not only informed if he transitions to a relaxed state, but is also quickly informed when he reaches this state or when achieving such a state is deemed unlikely.

As used here, the rate of change expresses the degree of change in the indicator currently being calculated versus the indicator's daily value or a preset target value. However, it is also acceptable for the rate of change to express the value of the indicator currently being calculated versus the value of the indicator calculated prior to the start of the current measurements. If this latter case is employed, then it is possible to confirm in real time the change in the degree of relaxation during measurement.

In this case, it is acceptable to provide a design which notifies the user only of the degree of relaxation. However, it is more preferable to also include a means of notification to specifically guide the user so that he can improve the degree of relaxation. For example, a design may be considered in which the user is directed to slow deep breathing, and is provided with a specific timing for that purpose, in the case where the degree of relaxation is not improving. In this case, if the number of deep breaths is made to correspond to the multiplying factor or the grade value, then the degree of relaxation during measurement can be readily improved to the desired extent. It is necessary to measure the user's respiration rate in this case. Since the HF component explained above corresponds to respiration, the respiration rate can be determined by specifying the frequency thereof. For example, in the example shown in FIG. 5A, the HF component is 0.25 Hz, so that the respiration rate is 15 times per minute. Accordingly, the user's state of relaxation can be promoted by notifying him to carry out deep respiration at a rate slower than the determined respiration rate.

The above-described notification can be carried out by means of display device 10 or sound source 7 of the device which is incorporated in a wristwatch. However, a design is also acceptable in which the necessary data is sent to the external device shown in FIG. 10 via I/O interface 15, and a determination of the degree of relaxation is made by the external device.

When the degree of relaxation is determined by the external device, the user employs button 22 provided to wristwatch 20 and sets the device in the mode for data transmission. CPU 1 then reads out the values of RR50 which have been stored in RAM 3 in association with the measurement time, and sequentially sends these to I/O interface 15. As a result, the RR50 values which are associated with the measurement times are converted to optical signals, relayed from LED 59 which is attached to communications connector 58, and sent to the personal computer in the external device after traveling through communications window 57 and photo transistor 55. The microprocessor which is housed in the personal computer then stores the measurement results in the internal RAM or hard disk. Accordingly, by operating the personal computer, a physician or other director can objectively ascertain the course of the user's state of relaxation, and obtain guidance with respect to the degree of relaxation. When the degree of relaxation is determined by the external device, the guidance to be provided in response to that degree of relaxation may be determined by the personal computer or by a director, such as a physician, who is operating the external device.

In addition, when the degree of relaxation is determined by the external device, it is acceptable to provide a design which guides the user by sending directions in response to the degree of relaxation determined by the external device to the wristwatch. A design of this type is effective in the case where the device incorporated in the wristwatch is separated at some distance from the external device. This device may have a design wherein directions are directly received from the external device, or wherein control information is received in response to the degree of relaxation and the user is notified of directions in accordance with this control information.

<2: Second Embodiment>

Next, a biofeedback guidance device according to a second embodiment of the present invention will be explained.

The preceding first embodiment focused on notifying the user once he reached a state of relaxation. In contrast, the second embodiment proceeds one step beyond this. Namely, in this embodiment, as the user carries out relaxation training, he is notified of the current indicator value and the degree of relaxation attained based on this indicator. By being aware of the improvement in his physiological state, the user reaches a deeper state of relaxation within a shorter period of time.

In order to realize this embodiment, it is first assumed that the user performs a type of training known as autogenic training. A simple explanation will now be made of the autogenic training upon which the biofeedback guidance device of this embodiment is presupposed.

In general, the human autonomic nervous system is most notably expressed in changes in the pulse wave at the periphery of the body. Therefore, the pulse wave is continuously measured at the periphery, and the user is notified of the degree of relaxation obtained from the pulse wave fluctuation and the current indicator value. In response, the user creates an environment or makes suggestions which will facilitate better relaxation. This has an effect on the autonomic nervous system, and enables the user to improve his state of relaxation even further. This type of physiological loop is the biofeedback touched on above. The efficacy of biofeedback has already been verified as described above, and has been found to be effective as one form of treatment in clinical trials.

FIG. 1B is a block diagram showing the functional structure of the biofeedback guidance device according to the second embodiment of the present invention. The difference between the device shown in this figure and that of the first embodiment shown in FIG. 1A is in the provision of a notifying member 105 for notifying user Y of the indicators extracted by physiological information extractor 101. User Y carries out autogenic training in accordance with the degree of relaxation and the results of the determination as notified by notifying member 104 and in accordance with the current indicator value as notified by notifying member 105.

<2-1: Specific Structure of Second Embodiment>

As may be understood from FIG. 1B, the structure of the biofeedback guidance device according to the present embodiment is achieved essentially by adding notifying member 105 to the device shown in FIG. 1A. Notifying members 104 and 105 can share sound source 7 and display device 10 shown in FIG. 2. For this reason, the structure of the biofeedback guidance device according to this embodiment is approximately the same as the relaxation guidance device according to the first embodiment, and differs only in the processing carried out by CPU 1.

<2-2: Operation of Second Embodiment>

The operation of a biofeedback guidance device of the above design will now be explained. First, when carrying out autogenic training, the value of the upper limit for training time and the training target value (rate of change in RR50, explained in detail below) are set for each training session. In this embodiment, a physician or other director sets these values from an external device. Namely, the director employs key board 52 (see FIG. 10B) to input commands for setting the upper limit values and target values, and the microprocessor housed in the personal computer, which is the external device in this case, sends the setting information to wristwatch 20. This information is then emitted to the outside in the form of near infrared light via LED 54, and sent to the I/O interface 15 shown in FIG. 2 via photo transistor 60 in wristwatch 20. CPU 1 then uptakes and stores the relayed information in RAM 3.

Note that setting of the upper limit value and the target value may be done by operating switches 21,22 on the device main body, without relying on an external device.

Next, when the user depresses button 21, CPU 1 detects this as the start of autogenic training and sets timer 12 to generate an interrupt at specific time intervals. CPU 1 also sets timer 12 to generate a separate interrupt after the elapse of a time period corresponding to the upper limit value for training duration, as described above.

Having depressed button 21, the user focuses on relaxing, and initiates autogenic training, making suggestions for relaxation, etc.

The pulse wave signal detected by pulse wave sensor 5 is output via A/D converter 6 from the point in time when the power source of the device main body is turned on. When an interrupt is reported from timer 12 at fixed time intervals, CPU 1 takes up the pulse wave signal read out from A/D converter 6 and stores it in RAM 3. RR50 is calculated in accordance with the same procedure in embodiment 1, and stored in RAM 3 together with the measured clock time. Next, in order to inform the user of the value of the RR50 obtained, CPU 1 forms a voice message based on the RR50 value and the models for message information read out from ROM 2, and relays this to sound source controller 8. As a result, the user is notified in the form of a voice sounded from sound source 7 of the current RR50 value expressing physiological information.

As a result, the user recognizes that the RR50 value he has just heard has gotten even larger. As a result, biofeedback is achieved. As the effects of biofeedback are expressed, the user's condition improves, with the fluctuation in the pulse wave interval becoming larger, so that the RR50 value gradually increases.

In contrast, when biofeedback does not produce any effect, the user's state of relaxation remains unchanged or may have deteriorated to a state of greater tension. Thus, the RR50 value does not change or else shows a slight decrease. Accordingly, by listening to the increase or decrease in the RR50 value which is output from sound source 7, the user can confirm his own state of relaxation in real time and use this as a target in autogenic training.

On the other hand, at the time of each measurement, CPU 1 uses the RR50 value measured during a specific interval of time in the past, which includes at least the immediately preceding measurement, and the current RR50 value, and calculates the trend of the change between these two values. CPU 1 then determines whether or not the current RR50 value is shifting in the direction of increasing tension, and informs the user of the results of this determination.

Next, CPU 1 repeatedly carries out processing to notify the user of the RR50 value at the specific time intervals which have been set in timer 12. The user continues autogenic training in accordance with this notification. During the repetition of this processing, it is possible that timer 12 may report an interrupt due to the elapse of a period of time corresponding to the value of the upper limit for autogenic training. This occurs because autogenic training is not proceeding well, signifying that little effect is likely to be achieved even if autogenic training is continued beyond this point. Therefore, CPU 1 notifies the user to end autogenic training. In response to this, the user suspends autogenic training.

When autogenic training fails to have an effect as described above, CPU 1 provides specific directions to the user so as to produce an effect from training. As one example of these directions, the user may be directed to carry out the various relaxation training approaches described in detail for the first embodiment. By carrying out relaxation training in the form of single exercises in this way, however, it is not possible for the user to know the effects of his efforts, as is possible in the case of the autogenic training method employing biofeedback in this present embodiment. Thus, after carrying out the directions indicated by CPU 1, the user confirms the efficacy of the directions by again initiating autogenic training using biofeedback in the same sequence as described above.

In the case where there is no notice to suspend autogenic training, but the user depresses button 21 again in order to end training, CPU 1 detects this operation and terminates processing.

Next, CPU 1 begins processing to calculate the rate of change in the RR50 as a result of the autogenic training just carried out. Namely, from among the information stored in RAM 3, CPU 1 reads out the RR50 value obtained immediately after training began, the RR50 value obtained immediately before training ending, and the clock times at which these RR50 values were measured. CPU 1 then calculates the net training time based on the starting and ending clock times for the measurement, and determines the rate of change in the indicator (the RR50 value, here) according to the following equation. The result is then stored in RAM 3.

Rate of change in indicator (RR50)=( indicator value at the end of autogenic training−indicator value at the beginning of autogenic training )÷training time By calculating this rate of change, the biofeedback effects can be quantified. Namely, the rate of change expresses the degree of change in the indicator per unit time (and therefore the state of relaxation). The larger this value, the more quickly the user entered a state of relaxation, and the more quickly biofeedback effects were expressed.

In addition to the processing described above, CPU 1 may also apply a grade to the effect produced by autogenic training by means of the same procedure discussed in the first embodiment, and display this for the user. If the calculated grade is "0", for example, then CPU 1 provides various directions to the user as described above, and notifies the user to again try autogenic training once he enters a state of relaxation.

CPU 1 stores the rate of change in the RR50 in RAM 3 in association with the clock time of the measurement at the end of each training session. At the same time, CPU 1 displays the rate of change in the RR50 over time (trend) in the form of a graph, and displays this on display device 10. As a result, if the RR50 value rises as the user accumulates autogenic training on a daily basis, then the user understands that autogenic training has produced results. Further, when the user views the degree of that increase, he is able to directly understand how quickly his state of relaxation has improved. Conversely, if the rate of change in the RR50 value is flat or falls, then the user is able to know that the effects of autogenic training has been unfavorable.

Further, data about this trend information can be sent to an external device such as a personal computer. In this case, the user uses a button 22 provided to wristwatch 20 to set the device in the mode for data relay. As a result, CPU 1 reads out the trend information stored in RAM 3 and sends it to I/O interface 15. The trend information is converted to an optical signal, sent from LED 59 attached to communications connector 58, and relayed to the personal computer in the external device via communications window 57 and photo transistor 55. The microprocessor inside the personal computer then stores the measurement results in the internal RAM or hard disk. As a result, the physician or other director is able to ascertain the course of the user's autogenic training by operating the personal computer, and can set targets for the training as part of a prescription for the user's daily activities.

When autogenic training is carried out repeatedly on a daily basis, alteration in the rate of change of the RR50 ceases to be seen, even if training is continued. Namely, a saturation state has been reached. This state may be viewed as attainment of the target. Accordingly, in order to detect this state, at the end of each training session, CPU 1 compares the target value set prior to the start of autogenic training and the actual measured value for the rate of change in the RR50 value. If the measured value exceeds the target value, then the desired target value is viewed to have been reached, with the user then provided a notice such as "Sufficient effect from autogenic training. Maintain current state."

When the user's body is moving, then the measured result for the rate of change in the RR50 will include a change component due to this movement, as well as to the biofeedback performed. Therefore, the effect due to the user's movement is conjectured from the change in the pulse rate. To achieve this, an exercise load is applied on the user in advance, and the correlation between the pitch of body movement and the pulse rate is measured.

During autogenic training, the amplitude output from acceleration sensor 13 is checked, and the pitch of body movement is calculated from the time period during which an output amplitude above a specific value is obtained. In addition, the pulse waveform read out from A/D converter 6 is stored in RAM 3. The stored pulse waveform is segregated into beat units, and the pulse rate while body movement is being detected is calculated. Then, from the relationship between the measured pulse rate, body movement pitch, and pulse rate, the component of the change in the pulse rate which is due to autogenic training can be calculated, and the results for notification can be corrected after referring to this value.

While the user is carrying out autogenic training, CPU 1 reads out the output from acceleration sensor 13 via A/D converter 14, and determines whether or not this output is above a specific value (0.1 G, for example). CPU 1 than informs the user of the result of body movement detection by voicing "body motion present"/"body motion absent".

Figure 18A:
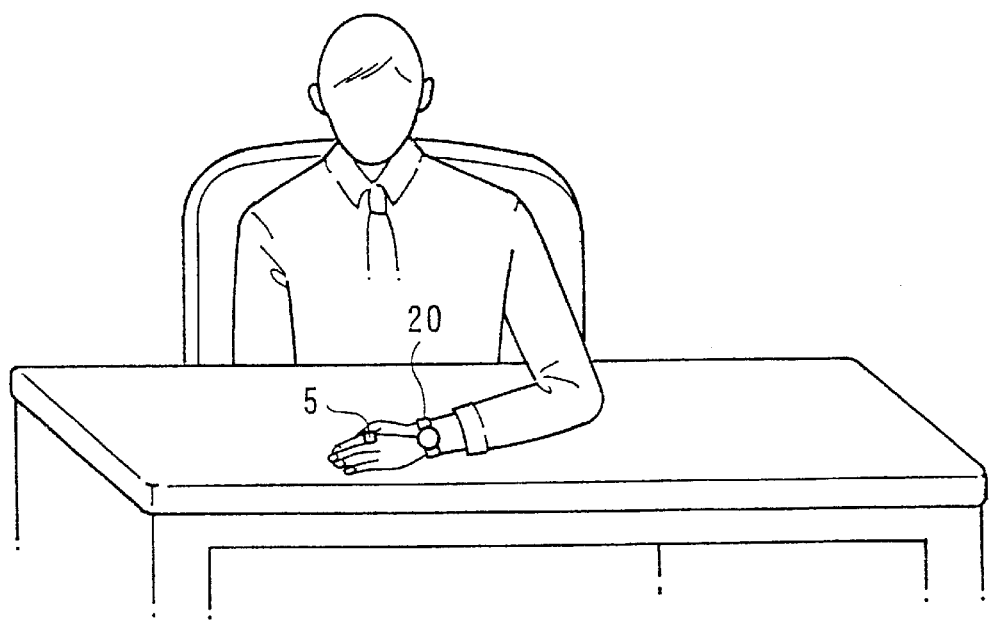
FIGS. 18A and 18B show the preferred arrangement for measuring the pulse wave, in the case where the subject is 18A sitting, or 18B standing.

With respect to the presence or absence of body motion, more specifically, body motion would be deemed present in the case where the arms are moving, for example. Accordingly, the user is of course viewed to be moving during exercise, walking, or moving around a room. The following arrangement is desirable in order to carry out autogenic training in a state so that body motion is not present. For example, if the user is inside, he should move to a room where there is a desk and chair. The user may then sit in the chair as shown in FIG. 18A, and place the arm with the watch on the desk, taking care not to move his hand.

Figure 18B:
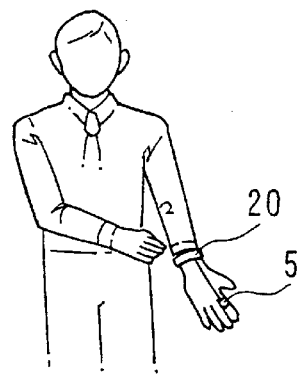

While the preceding arrangement is ideal, it may not always be possible, such as when the user is outside, for example. In this case, if the user is exercising, for example, exercise is suspended and breathing is allowed to return to normal. Similarly, if the user is taking a walk, then this activity is suspended. Next, the user assumes a position such as shown in FIG. 18B, for example, and carries out the necessary operations by using the opposite hand to press the buttons on the wristwatch while trying not to move the arm on which the watch is worn. Autogenic training is carried out as the user performs these operations.

In the case where the device has the form of a necklace or eyeglasses, as will be explained below, to which pulse wave sensor 5 is attached, the user may be either seated in a chair or standing, so long as there is little movement.

In the second embodiment described here, the user carries out autogenic training using biofeedback, based on indicators expressing the degree of physiological relaxation as informed by CPU 1. Further, the degree of change in the indicator generated as a result is evaluated, and the user is informed of this result. Thus, the user can easily understand what effects from autogenic training using biofeedback are being expressed. In addition, even if a specialist such as a physician is not available during autogenic training using biofeedback, the user is able to evaluate these results by himself.

<3: Other Examples of Indicators Expressing Physiological State>

The preceding embodiment employed RR50 as an indicator which expresses the physiological state, with the degree of change in this indicator employed to evaluate the state of relaxation. However, it is also acceptable to employ the HF component for this purpose. Moreover, the LF component and the amplitude ratio LF/HF are equivalent to the RR50 and HF component, with the exception that their values gets smaller as the state of relaxation increases. Accordingly, it is acceptable for the user may focus on making these values smaller during autogenic training.

The indicators obtained from the pulse waveform fluctuation in the preceding embodiments were employed as indicators expressing physiological state. However, the present invention is of course not limited thereto. Namely, the following other examples may be cited of indicators which express the physiological state.

<3-1: Blood Flow at Periphery (Amplitude of Pulse Waveform)>

In general, the state of the autonomic nervous system is well expressed by changes in peripheral blood flow. Body temperature is controlled by the amount of blood traveling through the blood vessels, with body temperature increasing as blood flow volume increases.

Therefore, the user may create an environment conducive to relaxation or make suggestions so that the body temperature at the fingertips or other periphery rises, while continuously measuring changes in peripheral blood flow and observing the results obtained from the measurements. As a result, autonomic activity is linked to an increase in body temperature at the periphery, with the state of blood flow improving.

The following is one example of a method by means of which the state of peripheral blood flow may be understood. Namely, using pulse wave sensor 5 according to the first or second embodiment of the present invention, light is irradiated from the LED (light emitting diode) which forms the sensor onto the red blood cells in the blood. The hemoglobin in the red blood cells absorbs light of a specific wavelength, while the light which is not absorbed is reflected back. If the reflected light is received by a light receiving element which forms the pulse wave sensor, then a correlation is obtained between the quantity of reflected light (i.e., the pulse waveform signal detected by the pulse wave sensor) and the blood flow volume. Accordingly, by observing the change in the amplitude of the pulse waveform obtained, it is possible to detect the relative change in the state of blood flow at the periphery.

For this reason, a structure which employs the amplitude of the pulse waveform as an indicator expressing physiological state may be achieved which is equivalent to that of embodiment 1 shown in FIG. 2. However, since a structure which detects the change in amplitude of the pulse waveform only is sufficient, the processing load which is carried out by CPU 1 is reduced as compared to the case where employing RR50 as the indicator.

Figure 19:
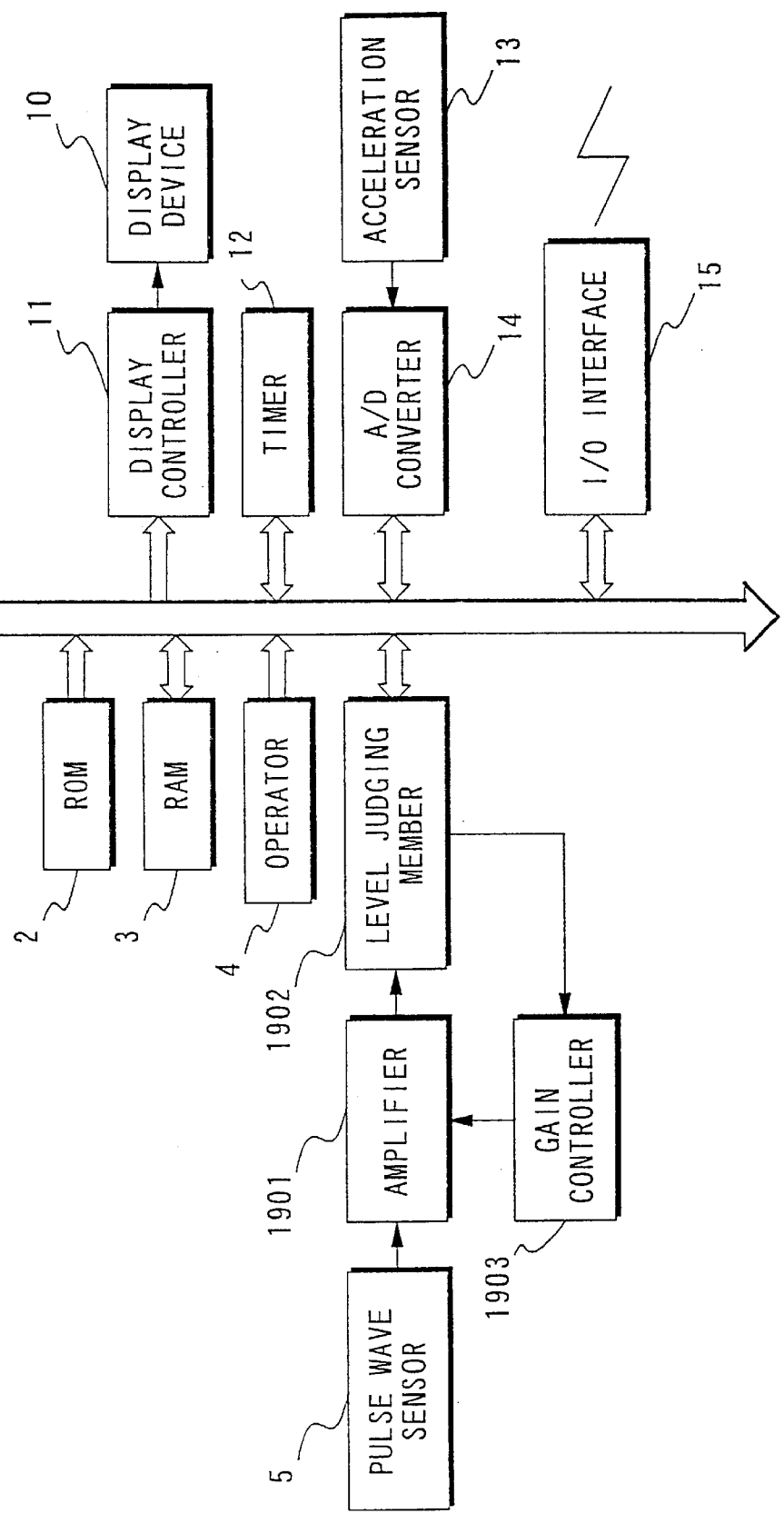
FIG. 19 shows a design wherein the amplitude of the pulse waveform is employed as an indicator expressing physiological information.

A structure such as shown in FIG. 19 is also acceptable, in which the detection of the change in amplitude of the pulse waveform is specified. The structure in this figure differs from that shown in FIG. 2 in that A/D converter 6 positioned behind pulse wave sensor 5 is replaced by amplifier 1901, level judging member 1902, and gain controller 1903. Accordingly, these points of difference will be explained below.

Figures 20, 21:
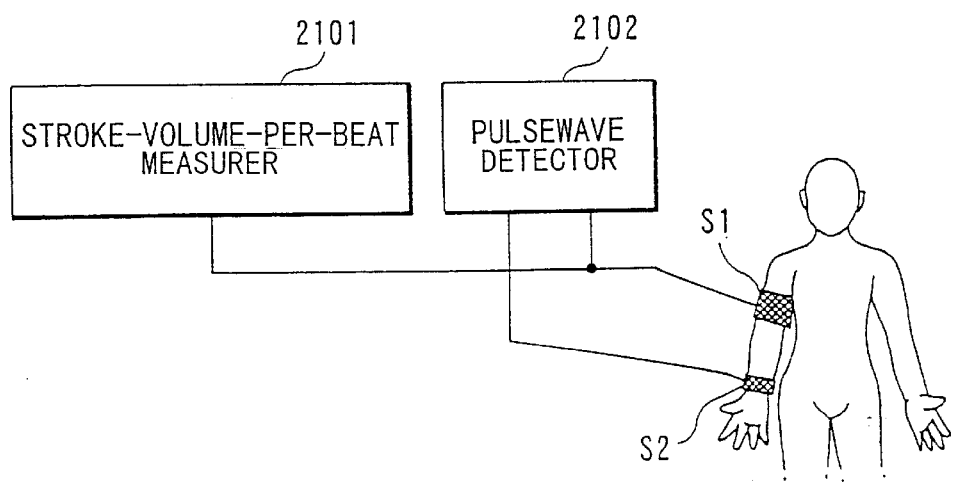
FIG. 20 shows the relationship between the effective bit number associated with the level judging member in this design, the shift indication quantity, and the gain control quantity.
FIG. 21 shows the structure for determining the circulatory state parameters employing a lumped parameter model.

In FIG. 19, level judging member 1902 executes A/D conversion on the signal output from amplifier 1901, as indicated by CPU 1, and stores the converted digital signal (i.e., pulse waveform signal) over a specific period of time. For this reason, level judging member 1902 houses a memory which is not shown in the figures. Level judging member 1903 determines the maximum signal value from among the stored pulse waveform signals, calculates the "pulse wave amplitude" during measurement, and then calculates the "effective bit length" when the pulse wave amplitude value is converted to binary digits. As may therefore be understood, the larger the pulse wave amplitude value, the larger the effective bit length. In the figure, level judging member 1902 quantized the analogue signal taken up at 7 bits. As shown in FIG. 20, the effective bit length may be from 1 to 7 bits, but the present invention is of course not limited thereto.

Level judging member 1902 calculates the "shift indication quantity" and the "gain control quantity" based on the calculated effective bit length. The shift indication quantity is the necessary number of bits so that the effective bit length can be made full-scale (7 bits) by shifting the value of the pulse wave signal to the left, in the case where the pulse wave signal's effective bit length is small. Thus, the shift indication quantity is calculated by subtracting the effective bit length from the fixed value "7". On the other hand, the gain control quantity is the multiplying factor corresponding to this left shift and, as is clear from the figure, may be calculated by taking the shift indication quantity as the power to a base of 2.

Note that the aforementioned pulse waveform amplitude, effective bit length, shift indication quantity, and gain control quantity may all be read out from the bus. Accordingly, CPU 1 can uptake this data from the bus at any time. The true value of the pulse wave amplitude takes into account the amplitude of the pulse wave calculated by level judging member 1902 and the gain control quantity (shift indication quantity), and is obtained by dividing the former by the latter.

Further, level judging member 1902 is designed to carry out the calculation of the shift indication quantity and the gain control quantity only at the initial point in time when the pulse wave signal is taken up. These quantities are then held in the level judging member 1902 until the next uptake, and read into the bus. The value of these quantities immediately after the power source is turned on is set so that the gain control quantity becomes "1". This is equivalent in the case where level judging member 1902 initiates uptake of the pulse wave signal.

Gain controller 1903 controls the amplification factor of amplifier 1901 in accordance with the gain control quantity which is output from level judging member 1902.

In a design of this type, when pulse wave sensor 5 begins uptake of the pulse wave, the obtained pulse wave signal is amplified at amplifier 1901, and input to level judging member 1902. However, as mentioned above, the amplification factor of amplifier 1901 is set to be "1" when the power source is turned on.

Level judging member 1902 converts the analog signal output by amplifier 1901 to a digital value, and sequentially writes this value in the internal memory, Level judging member 1902 stores the pulse waveform by carrying out this write process over a fixed period of time. Next, from among the stored pulse waveforms, level judging member 1902 extracts the pulse waveform which has the maximum signal value, calculates this as the pulse wave amplitude and determines the effective bit length of the pulse wave amplitude. Here, it is assumed that an effective bit length of 2 is calculated, with level judging member 1902 calculating 5 bits as the shift indication quantity and 32 bits as the gain control quantity. As a result, gain controller 1903 changes the amplification factor of amplifier 1901 to 32, and subsequently, values near full-scale are output from amplifier 1901 at the A/D converter in level judging member 1902.

On the other hand, CPU 1 reads out the shift indication quantity and the amplitude of the pulse waveform calculated by level judging member 1902 and stores these values in RAM 3 together with the time read out from timer 12. The bit number "5" of the shift indication quantity is sent to display controller 11, and the value of the shift indication quantity is displayed on display device 10. In other words, the bit number of the shift indication quantity is notified to the user as the change in amplitude of the pulse waveform.

CPU 1 determines the change in the amplitude of the pulse waveform by carrying out processing in the same way as when determining the rate of change in embodiments 1 and 2. As a result, even when the amplitude of the pulse waveform is employed as an indicator which expresses physiological information, it is possible to confirm the degree of relaxation and the effects of autogenic training using biofeedback.

<3-2: Circulatory State Parameters>

As explained above, since there is a close relationship between changes in peripheral blood flow volume and the pulse waveform, if the state of the circulatory system, including the periphery, is understood, then it is possible to estimate to some extent the change in the pulse waveform. In order to know the circulatory state, it becomes necessary to measure such circulatory state parameters as compliance or viscous resistance in the blood vessels. In this case, the pressure waveform and blood flow rate at the proximal portion of the aorta and at the site of insertion of a catheter into an artery need to be measured. For this purpose, a direct method of measurement, in which a catheter is inserted into an artery, or an indirect method employing ultrasound waves, may be applied. However, the former method is a form of invasive measurement, while the latter method requires training. Moreover, both methods necessitate a large device to carry out the measurements.

The present inventors have therefore proposed a method in which the circulatory state parameters are approximately calculated using an electric model which simulates the behavior of the arterial system (see Japanese Patent Application Hei 6-205747: Title: Pulse wave analyzer, or PCT/JP96/03211: Title: Device for measuring physiological state).

Figure 22A:
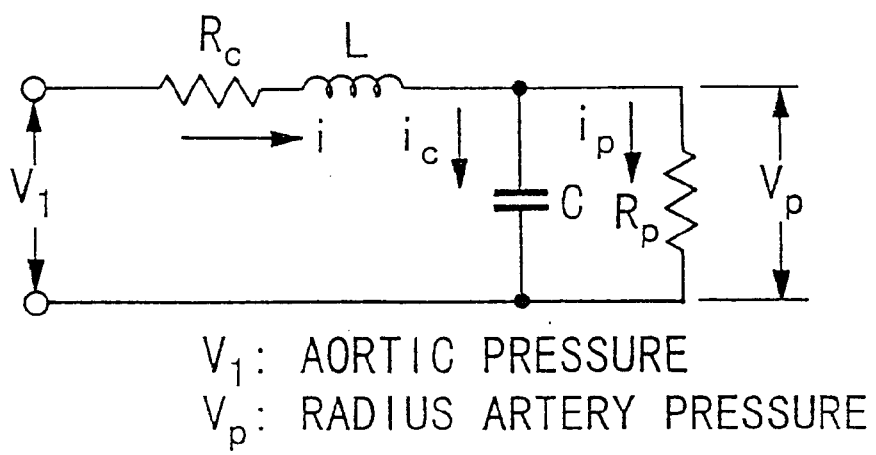
FIG. 22A is a circuit diagram showing the structure of the lumped four parameter model for simulating the arterial system of the human body.
Figure 22B:
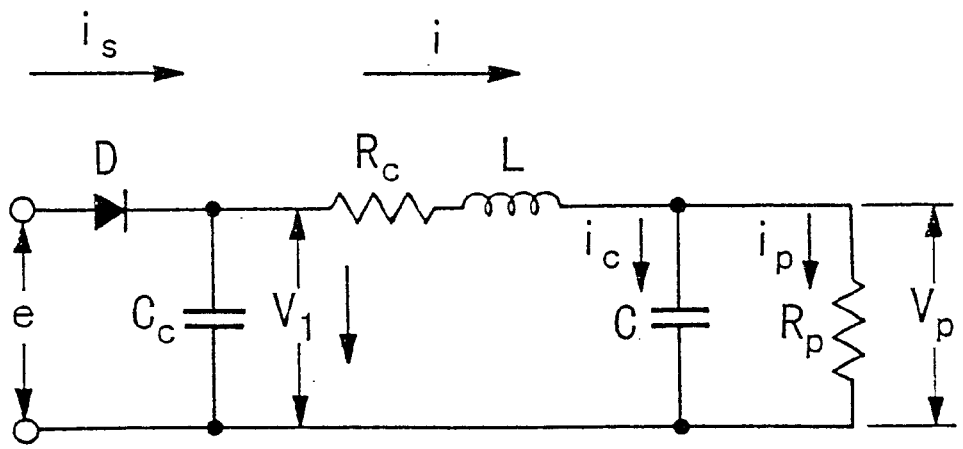
FIG. 22B is a circuit diagram showing the structure of a lumped five parameter model.
Figure 23:
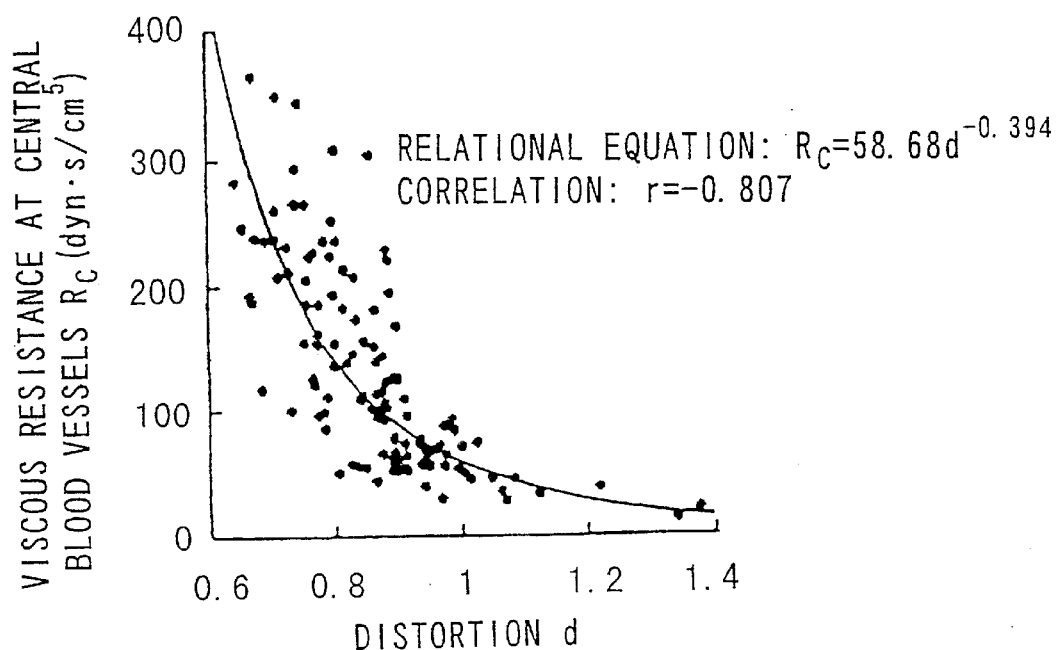
FIG. 23 shows the correlation between distortion d and vascular resistance at the core of the body, Rc.
Figure 24:
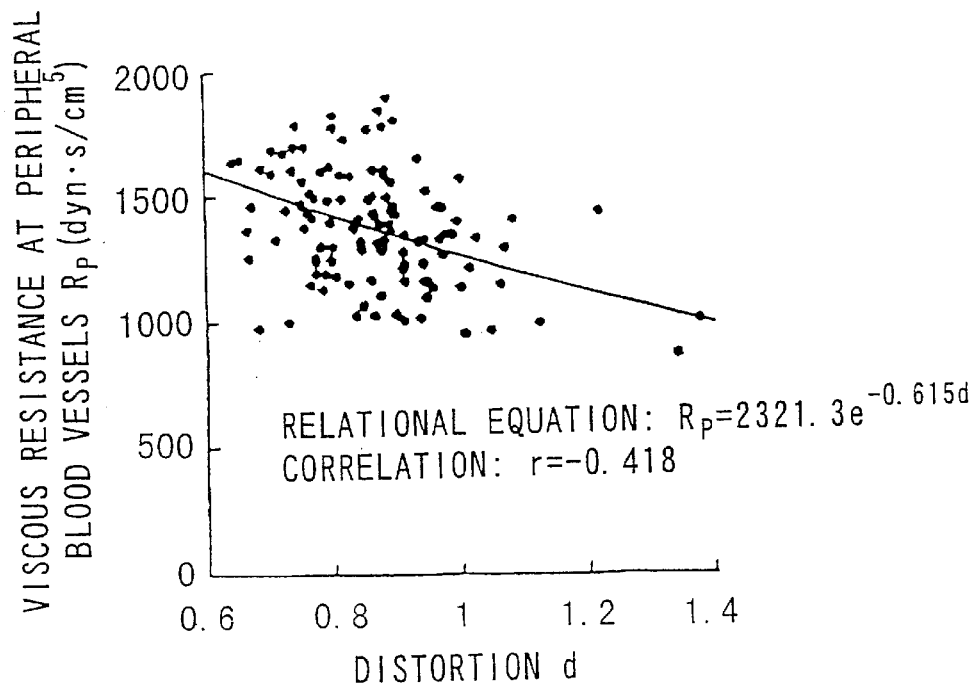
FIG. 24 shows the correlation between distortion d and vascular resistance at the periphery of the body Rp.
Figure 25:
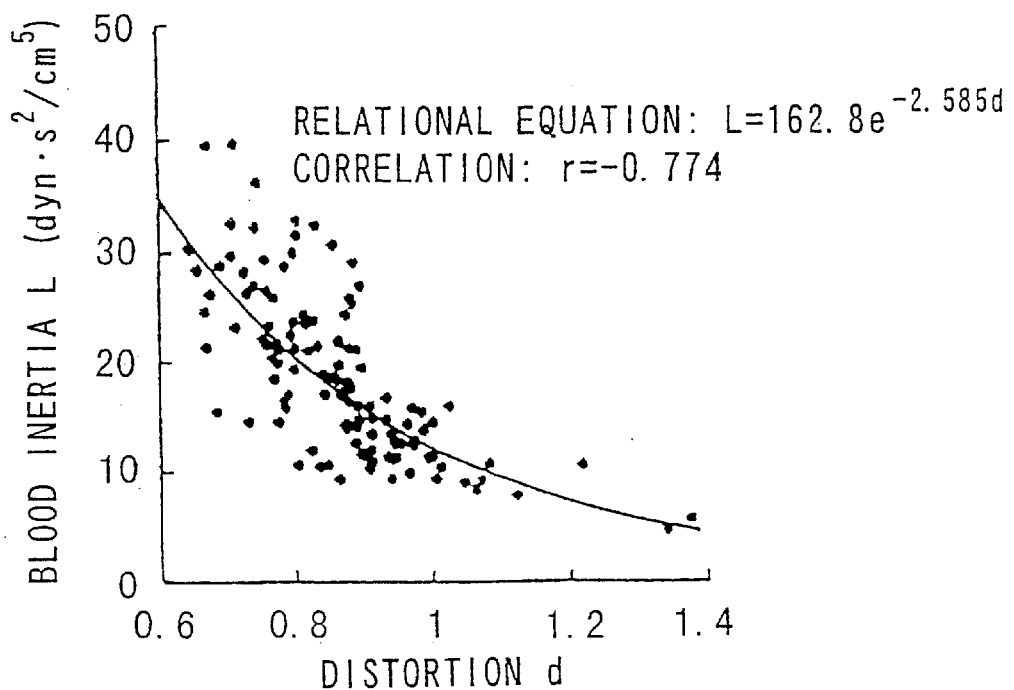
FIG. 25 shows the correlation between distortion d and inductance L from the blood.
Figure 26:
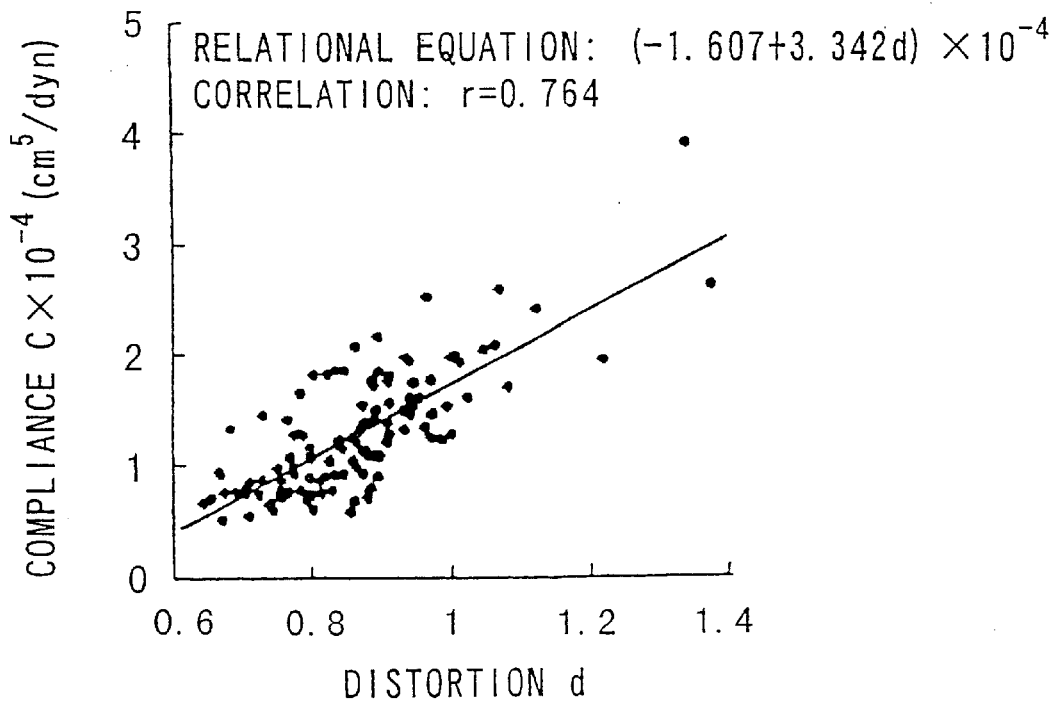
FIG. 26 shows the correlation between distortion d and compliance C.

FIG. 22A shows a lumped four parameter model, while FIG. 22B shows a lumped five parameter model. Specifically, a lumped five parameter model employs an electrical circuit to model the four parameters employed in a lumped four parameter model, namely, inductance due to blood at the center of the arterial system; blood vessel resistance (viscous resistance) due to blood viscosity at the center of the arterial system; compliance (viscosity) of blood vessels at the periphery; and blood vessel resistance (viscous resistance) at the periphery; as well as aortic compliance; these parameters contributing to the determination of the behavior of the circulatory system.

The relationship between the parameters and the elements making up the lumped parameter model is as follows.

Capacitance $C_c$: aortic compliance ($cm^5/dyn$)

Electrical resistance $R_c$: blood vessel resistance due to blood viscosity at the center of the arterial system ($dyn \cdot s/cm^5$)

Inductance L: inertia of blood at center of arterial system ($dyn \cdot s^2/cm^5$)

Capacitance C: compliance of blood vessels at periphery of arterial system ($cm^5/dyn$)

Electrical resistance $R_p$: blood vessel resistance at periphery of arterial system due to blood viscosity ($dyn \cdot s/cm^5$)

Currents i, $i_p$, $i_c$, and $i_s$, which are flowing through each part of the electrical circuit, correspond to blood flow ($cm^3/s$). Current i is the blood flow at the aorta and current $i_s$ is the blood flow pumped out from the left cardiac ventricle. Input voltage e corresponds to the pressure in the left cardiac ventricle ($dyn/cm^2$), while voltage $v_1$ corresponds to the pressure ($dyn/cm^2$) of the proximal portion of the aorta. Terminal voltage $v_p$ of capacitance C corresponds to the pressure ($dyn/cm^2$) at the radius artery. Further, diode D corresponds to the aortic valve. Diode D is on (valve open) during a period corresponding to contraction, and off (valve closed) during a period corresponding to expansion.

A detailed explanation of these techniques is covered in the above-cited references. To state simply, however, an electric signal corresponding to the pressure wave at the proximal part of the aorta in a test subject is provided to the lumped parameter model. Then, the values of each of the elements is determined based on the stroke volume per beat measured by stroke-volume-per-beat measurer 2101 in FIG. 21, so that the response waveform coincides with the radius artery waveform detected by pulse wave detector 2102. Further, if a structure corresponding to stroke-volume-per-beat measurer 2101 is added to the structure shown in FIG. 2, then processing can be carried out by CPU 1.

Blood vessel resistance due to viscosity and blood vessel compliance at the periphery of the arterial system are believed to be closely related to the amount of blood flow at the periphery. Therefore, as a result of CPU 1 determining the change in compliance C and electrical resistance Rp as indicators expressing physiological state, it is possible to confirm the degree of relaxation and the results of autogenic training using biofeedback. A design is also acceptable in which the circulatory state parameters are determined and notified to the user when he is carrying out autogenic training using biofeedback.

<3-2-1: Distortion in Pulse Waveform>

In the design shown in FIG. 21, when calculating the values of each of the circulatory state parameters, it is necessary to detect both the radius artery waveform and the stroke volume per beat for the user. This has been troublesome and, therefore, problematic. Therefore, the circulatory state parameters are derived by focusing on the change in the aortic pressure based on the shape of the radius artery waveform, and representing the shape of the waveform by the distortion.

In this case, CPU 1 determines the average waveform per beat for the radius artery waveform, and then performs Fourier analysis by carrying out a fast Fourier transform (FFT) on the average waveform. Next, the fundamental wave's amplitude $A_1$, the second harmonic wave's amplitude $A_2$, the third harmonic wave's amplitude $A_3$, . . . to the nth harmonic wave's amplitude $A_n$ are obtained from the frequency spectrum obtained as a result of this analysis. Here, the value of n (which is a natural number) is optimally determined after taking into consideration the size of the amplitude of the harmonic waves. Based on these amplitude values, then, distortion d defined by the following equation is calculated by CPU 1.

$$\text{distortion } d = \frac{\sqrt{A_2^2 + A_3^2 + \ldots + A_n^2}}{A_1}$$

Next, the circulatory state parameters are estimated from the obtained distortion d. This estimation is carried out based on the understanding that there is a correlation between the distortion d of the radius artery waveform and each of the values of the circulatory state parameters. Namely, distortion d and circulatory state parameters are measured in advance for a number of test subjects, and a relational equation between distortion and the circulatory state parameters is derived. Examples of correlations obtained as a result of measuring distortion d and the circulatory state parameters $R_c$, $R_p$, L and C are shown in FIGS. 23~26. Aortic compliance $C_c$ is not shown in these figures, however, a relational equation therefor may be obtained in the same manner as for the other four parameters. CPU 1 calculates the circulatory state parameters of $R_c$, $R_p$, L, C and $C_c$ from distortion d using the corresponding relational equations.

As a result of this design, it becomes possible to eliminate the stroke-volume-per-beat measurer 2101 structure shown in FIG. 21.

<3-3: Difference in Pulse Waveforms>

In order to know the state of the circulatory system, including the peripheral portions, the focus may be placed on the pulse waveform itself, as well as the circulatory state parameters described above. Therefore, an examination will be made of confirmation of the user's degree of relaxation and the effects of autogenic training using biofeedback from the values of the waveform parameters which specify the shape of the pulse waveform. When examining the shape of the pulse waveform, two methods may be considered. The first examines the time regions of the pulse waveform, while the second examines the frequency region. An examination of each of these methods follows below.

<3-3-1: Time Region>

Figure 27:
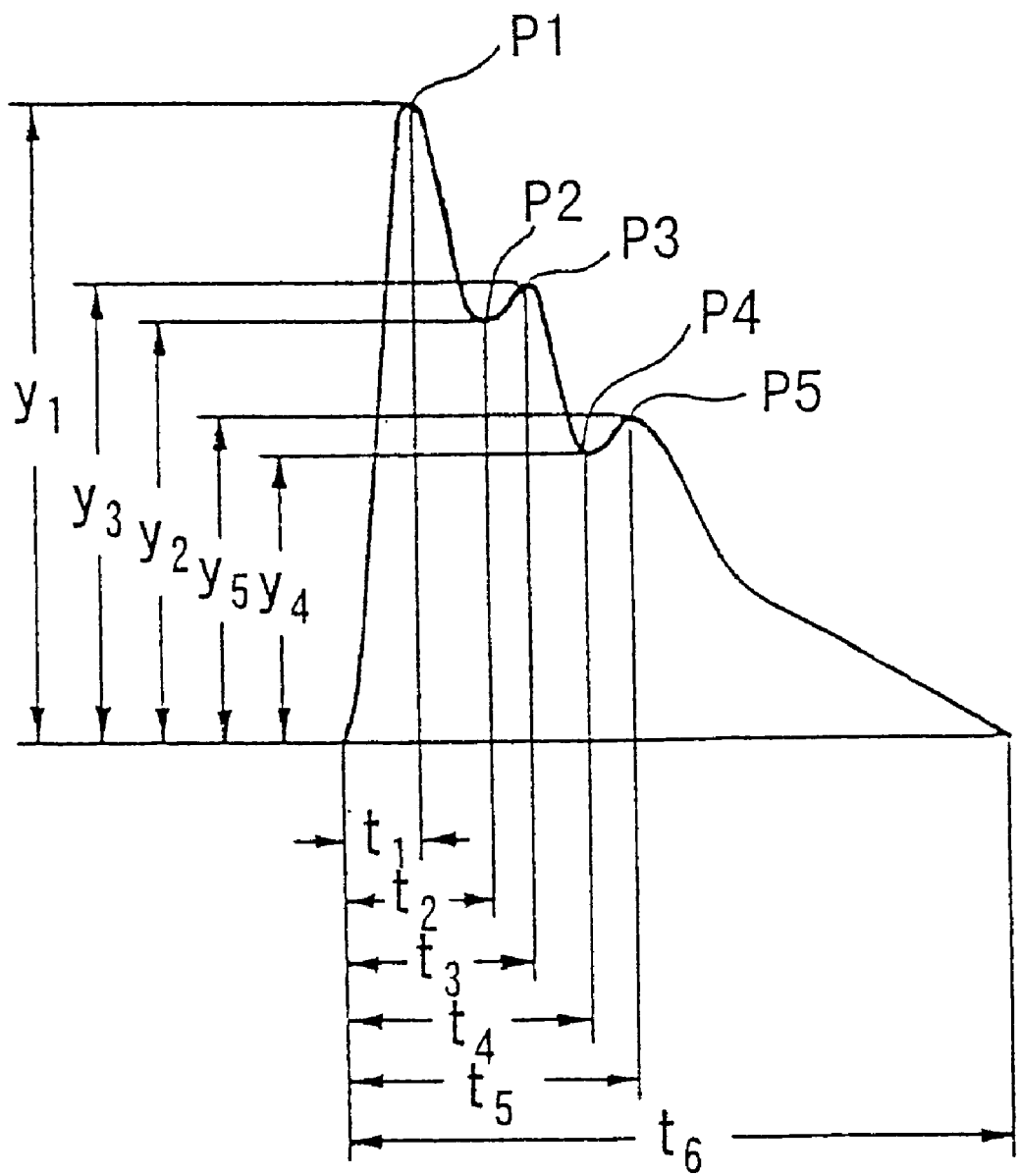
FIG. 27 shows the relationship between the pulse waveform of a single beat and the waveform parameters which characterize that waveform.

First, an examination will be made of confirmation of effects such as the degree of relaxation by using analysis results for the time region of a pulse waveform. In general, the waveform of one beat of a pulse wave has a shape such as shown in FIG. 27. Blood pressure is shown on the vertical axis, while time is measured on the horizontal axis. The waveform parameters for specifying the shape of the waveform of the pulse wave are as described below.

1. time $t_6$, the time period between the initiation of rise in consecutive waveforms associated with consecutive beats (hereinafter, this initiation of the rise in the waveform will be referred to as "time of pulse wave initiation")
2. blood pressure values $y_1 \sim y_5$ for the maximum point P1, minimum point P2, maximum point P3, minimum point P4 and maximum point P5 which appear sequentially in the pulse wave
3. elapsed times $t_1 \sim t_5$, which represent the respective times elapsed from pulse wave initiation until each of points P1 through P5, respectively, appear In order to calculate the waveform parameters, information referred to as "peak information" relating to each of the aforementioned maximum and minimum points is extracted. A waveform extraction memory, which will be described below, extracts the peak information from the pulse waveform taken up. Since the details of peak information are related to the structure and operation of the waveform extraction memory, an explanation thereof will be made when the structure of the circuit is explained.

<3-3-1-1: Structure of the Waveform Extraction Memory>

The structure of the waveform extraction memory will now be explained using FIG. 28. Waveform extraction memory 180 is assumed to be under the control of microcomputer 181. Note that this design may be realized using hardware. However, the equivalent functional structure may also be realized using software, based on the design shown in FIG. 2.

Figure 28:
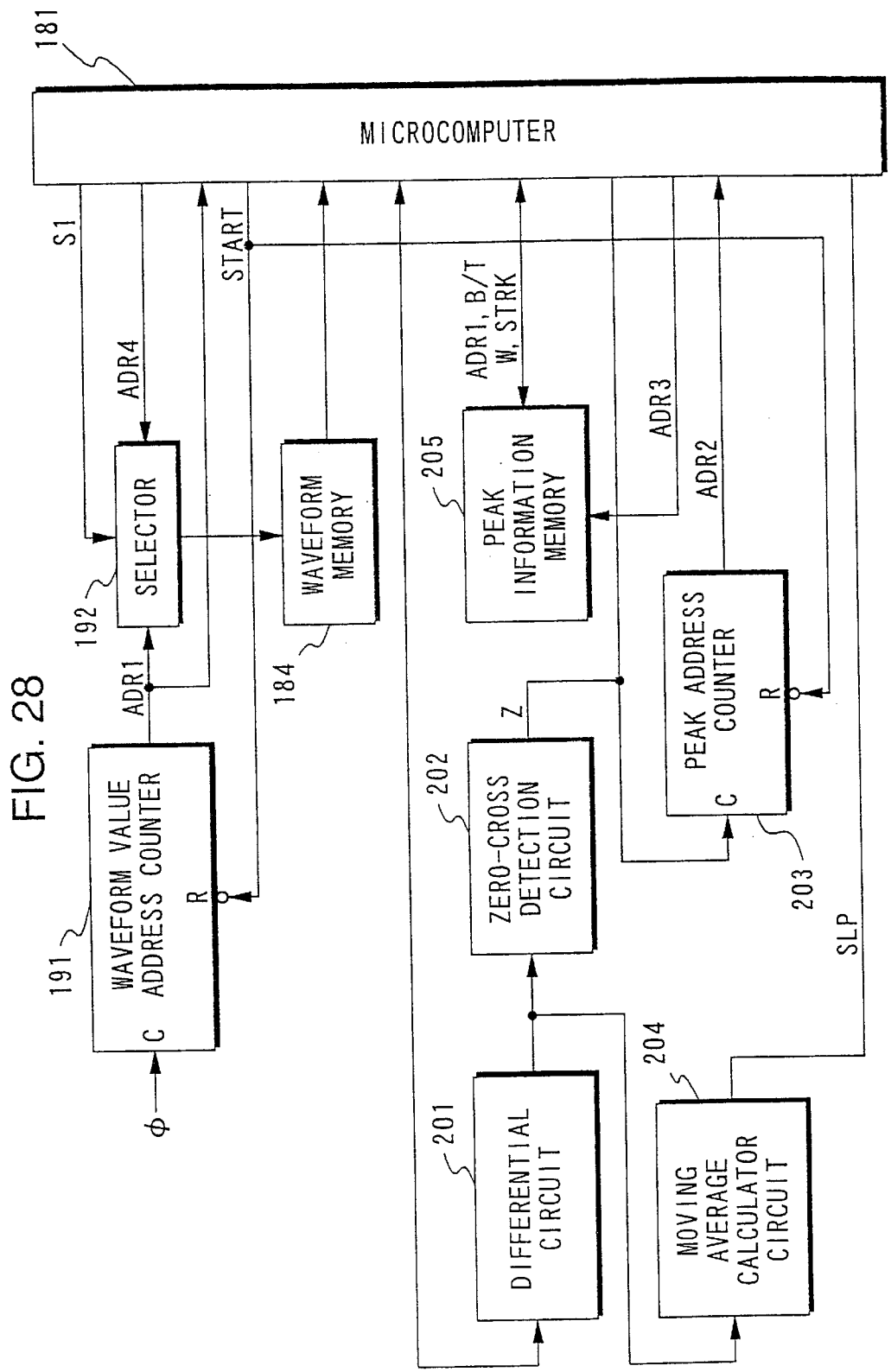
FIG. 28 is a block diagram showing the structure of the parameter extracting member.

In FIG. 28, 182 is an A/D converter which converts the pulse wave signal output from pulse wave sensor 5 to a digital signal in accordance with a fixed cycle sampling clock $\phi$. The numeric symbol 183 indicates a low pass filter which removes from the digital signals sequentially output from A/D converter 182 those components which exceed a specified cut-off frequency, and sequentially outputs this result as waveform value W.

The numeric symbol 184 indicates a waveform memory formed of RAM which sequentially stores the waveform values W supplied via a low pass filter 183. The numeric symbol 191 is a waveform value address counter which starts counting the sampling clock $\phi$ during the time period in which microcomputer 181 outputs a START directive to begin collecting the pulse waves. Waveform value address counter 191 outputs the counter result as the waveform value address ADR1 at which waveform value W is to be written. This waveform value address ADR1 is monitored by microcomputer 181. The numeric symbol 192 indicates a selector. When microcomputer 181 is not outputting a select signal S1, selector 192 selects the waveform value address ADR1 output by waveform value address counter 191, and supplies the selected waveform value address ADR1 to the address input terminal of waveform memory 184. In contrast, when a select signal S1 is being output by microcomputer 181, selector 192 selects the readout address ADR4 which is output by microcomputer 181, and supplies the selected readout address ADR4 to the address input terminal of waveform memory 184.

The numeric symbol 201 in the figure is a differentiation circuit which calculates the time differential of the waveform values W which are sequentially output from low pass filter 183. 202 is a zero cross detection circuit which outputs zero cross detection pulse Z when the time differential of the waveform value W is 0 because the waveform value W assumes a maximum or minimum value. More precisely, zero cross detection circuit 202 is provided to detect peaks P1, P2, ... in the waveform of the pulse wave disclosed in FIG. 29. Zero cross detection pulse Z is output when waveform values W corresponding to these peaks are input.

203 is a peak address counter. Peak address counter 203 counts zero cross detection pulse. Z while microcomputer 181 is outputting a START directive to begin collecting the pulse waves. Peak address counter 203 then outputs the counted result as peak address ADR2.

204 is a moving average calculator circuit which calculates the average value of the time differential of a fixed number of past waveform values W output from differentiation circuit 201 through the present point in time. The calculated result is output as slope information SLP indicating the slope of the pulse wave up through the current point in time.

Figures 29, 30:
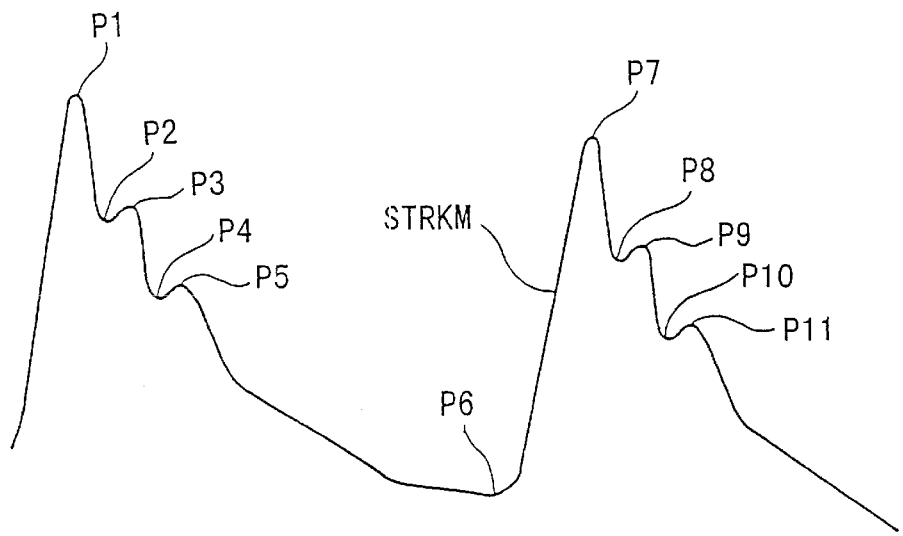
FIG. 29 is a diagram showing an example of the pulse waveform stored in the waveform parameters in this parameter extracting member.
FIG. 30 shows the storage contents of the peak information memory in this parameter extracting member.

205 indicates a peak information memory provided to store the peak information explained below. Peak information will be explained in greater detail below. Namely, the details regarding peak information shown in FIG. 30 are listed as follows.

1. waveform value address ADR1

The waveform value address ADR1 is the write address output from waveform value address counter 191 when the waveform value W output from low pass filter 183 is a maximum or minimum value. In other words, this is the write address in waveform memory 184 for waveform value W corresponding to a maximum or minimum value.

2. peak type B/T

The peak type is information indicating whether waveform value W which is written in waveform value address ADR1 is a maximum value T (Top) or a minimum value B (Bottom).

3. waveform value W

This is the waveform value corresponding to the maximum or minimum values.

4. stroke information STRK

The stroke information STRK is the amount of change in the waveform value from the immediately preceding peak value to the relevant peak value.

5. slope information SLP

This is the average value of the time differential of a fixed number of past waveform values up through the relevant peak value.

<3-3-1-2: Operation of Waveform Extraction Memory>

The operations of waveform extraction memory 180 under the control of microcomputer 181 will now be explained separately.

<3-3-1-2-1: Collection of Waveform and Peak Information>

When microcomputer 181 outputs a START directive to begin collecting waveforms, waveform value address counter 191 and peak address counter 203 cease to be reset.

As a result, the sampling clock φ counter is started by waveform value address counter 191. The counter value is supplied to waveform memory 184 via selector 192 as waveform value address ADR1. The pulse wave signals detected from the human body are input to A/D converter 182, and sequentially converted to digital signals in accordance with the sampling clock φ. These converted digital signals are then sequentially output via low pass filter 183 as waveform values W. The waveform values W output in this way are sequentially supplied to waveform memory 184, and written in the memory area specified by waveform value address ADR1 at that point in time. As a result of the preceding operations, a continuous waveform value W corresponding to the waveform of the radius artery is stored in waveform memory 184. This continuous waveform value W is shown in FIG. 29.

In parallel with the preceding operation, detection of peak information and writing to peak information memory 205 are carried out as explained below.

First, the time differential of the waveform values W output from low pass filter 183 is calculated at differential circuit 201, and then input to zero cross detection circuit 202 and moving average calculator circuit 204. Moving average calculator circuit 204 calculates the average value (i.e., moving average value) of a specified past number of time differentials each time the time differential of a waveform value W is supplied, and outputs the calculated result as slope information SLP. A positive value will be output for slope information SLP when waveform value W is rising or has reached a maximum value. Conversely, a negative value will be output for slope information SLP when waveform value W is falling or has reached a minimum value.

When waveform value W corresponding to maximum point P1 shown in FIG. 29, for example, is output from low pass filter 183, O is output from differential circuit 201 as the time differential, and zero cross detection pulse Z is output from zero cross detection circuit 202.

As a result, microcomputer 181 uptakes at that point in time waveform address ADR1, which is the counter value of waveform value address counter 191; waveform value W; peak address ADR2, which is the counter value of the peak address counter (here, ADR2=0); and slope information SLP. Further, when zero cross detection pulse Z is output, the counter value ADR2 of peak address counter 203 becomes 1.

Microcomputer 181 creates peak type B/T based on the sign of the uptaken slope information SLP. In this case, when the waveform value W of maximum value P1 is output, then positive slope information is output at that point in time. As a result, microcomputer 181 sets the value of peak information B/T to one corresponding to a maximum value. Microcomputer 181 indicates without modification the peak address ADR2 uptaken from peak address counter 203 (here ADR2=0) as write address ADR3, and writes waveform value W, its waveform address ADR1, peak type B/T, and slope information SLP as the first time peak information in peak information memory 205. When writing first time peak information, stroke information STRK is not created or written since there is no immediately preceding peak information.

When waveform value W corresponding to minimum point P2 shown in FIG. 29, for example, is subsequently output from low pass filter 183, zero cross detection pulse Z is output in the same way as above, and write address ADR1, waveform value W, peak address ADR2 (=1), and slope information SLP (<0) are taken up by microcomputer 181.

Next, in the same way as above, microcomputer 181 determines the peak type B/T (B, in this case) based on slope information SLP. Next, the address which is 1 less than peak address ADR2 is read out by microcomputer 181, and supplied to peak information memory 205 as address ADR3. Recorded waveform value W written the first time is then read. Next, microcomputer 181 calculates the difference between waveform value W taken up at the current time from the low pass filter 183 and the waveform value W read out from peak information memory 205 that was taken up the first time, thereby obtaining stroke information STRK. The thus obtained peak type B/T and stroke information STRK are written in the recording area corresponding to peak address ADR3=1 in peak information memory 205 as second time peak information together with other information such as waveform value address ADR1, waveform value W and slope information SLP. The same operation is then carried out when peaks P3, P4, . . . , are detected.

Once a specific period of time has elapsed, microcomputer 181 stops outputting the waveform collection directive START, and the collection of waveform value W and peak information terminates.

<3-3-1-2-2: Pulse Waveform Partitioning Processing>

Microcomputer 181 carries out processing to specify from among the various information stored in peak information memory 205 the information corresponding to the waveform of a single beat at which waveform parameter collection is carried out.

First, slope information SLP and stroke information STRK corresponding to each of the peaks P1, P2, . . . are sequentially read out from peak information memory 205. Next, stroke information corresponding to positive slopes are selected from each stroke information STRK (i.e., the corresponding slope information SLP which is positive). A specified number of the largest values are then selected from among this stroke information. Next, stroke information corresponding to medium values is selected from among the selected stroke information, and the stroke information for the rising portion (for example, the rising portion indicated by symbol STRKM in FIG. 29) of the pulse wave of one beat at which waveform parameter extraction is to be carried out is obtained. Next, the peak address preceding the peak address of this slope information (i.e., the peak address at point P6, the initiation of the pulse wave of one beat at which waveform parameter extraction is to be performed) is obtained.

<3-3-1-2-3: Extraction of Waveform Parameters>

Microcomputer 181 calculates each waveform parameter by referencing each peak information corresponding to the pulse wave of one beat recorded in peak information memory 205. This processing may be obtained as follows.

1. blood pressure values $y_1$~$y_5$

The waveform values corresponding to peaks P7~P11 are defined as $y_1$~$y_5$ respectively 2. time $t_1$ The waveform address corresponding to peak P6 is subtracted from the waveform address corresponding to peak P7. $t_1$ is calculated by multiplying the period of the sampling clock $\phi$ with this result.

3. time $t_2$~$t_6$

As in the case of $t_1$ above, $t_2$~$t_6$ are calculated based on the difference in the waveform addresses between each of the corresponding peaks.

Further, each of the waveform parameters obtained in this way are stored in the buffer memory inside microcomputer 181. Based on these waveform parameters, CPU 1 determines the change therein as indicators of physiological state. As a result, it is possible to confirm the degree of relaxation and the effects of autogenic training using biofeedback. For example, the interval between peaks P1 in adjacent pulse waves is the aforementioned RR interval, therefore, it is possible to obtain this RR50 interval without relying on FFT processing, and to confirm the degree of relaxation.

<3-3-2: Frequency Region>

Next, an examination will be made of confirmation of the degree of relaxation using the results of analysis of the frequency region of the pulse waveform. It believed that the frequency spectrum, or more specifically, the amplitude and phase of the frequency spectrum, obtained from frequency analysis of the pulse waveform is beneficial as characteristic information of the pulse wave.

FFT (Fast Fourier Transform) and the like are available as general methods for carrying out frequency analysis of waveforms, and accordingly would first be considered as methods for carrying out frequency analysis of waveforms. The individual waves which form the waveform of the pulse wave do not have the same shape, and, moreover, change over time. In addition, the wavelengths of each wave is not constant. When employing FFT in this case, a method is employed in which FFT is carried out by viewing pulse waves which demonstrate this kind of chaotic movement as waveforms having an extremely long period.

When FFT is employed, the wave pulse spectrum can be obtained in detail, but the volume of calculations tends to become very large. Therefore, for applications in which the wave pulse spectrum generated over time is obtained quickly, the present inventors developed the frequency analyzer explained below. This frequency analyzer, which carries out frequency analysis of the pulse waveform, is a spectrum detection circuit for extracting the amplitude and phase of the spectrum to be obtained. The frequency analyzer is controlled by microcomputer 181 and is operated in sync with waveform extraction memory 180 to detect the pulse wave spectrum at high speed.

<3-3-2-1: Structure of Frequency Analyzer>

The structure of the frequency analyzer will now be explained with reference to FIG. 31. It is assumed here that waveform extraction memory 180 is under the control of microcomputer 181. Note that this design may be realized using hardware. However, the equivalent functional structure may also be realized using software, based on the design shown in FIG. 2.

Figure 31:
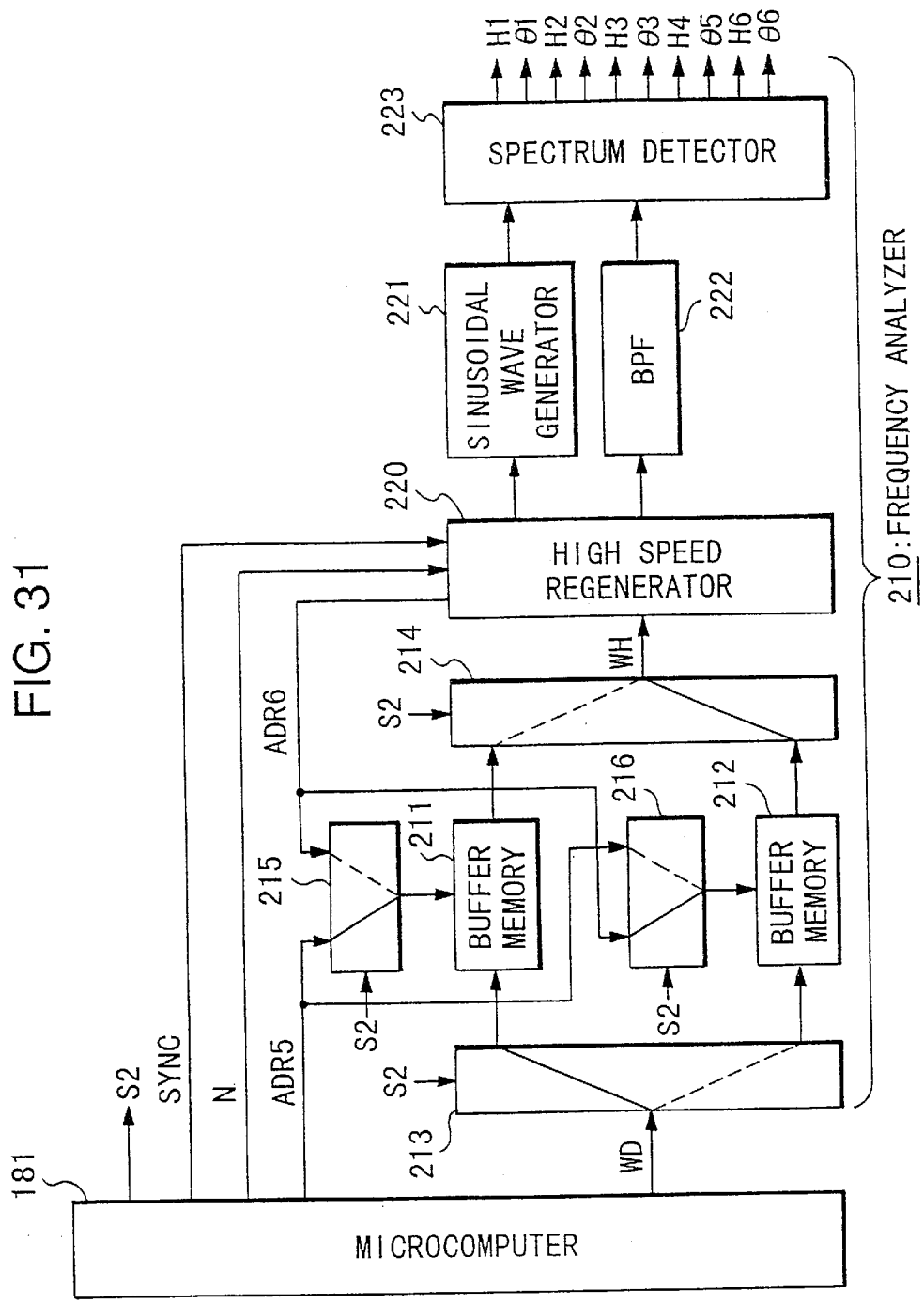
FIG. 31 is a block diagram showing the structure of the frequency analyzer.

FIG. 31 is a block diagram showing frequency analyzer 210 in detail. Frequency analyzer 210 receives waveform values WD of the pulse wave via microcomputer 181 at each beat. This received waveform value WD is repeatedly regenerated at high speed. Frequency analysis is carried out at each beat, to calculate the spectrum forming the pulse wave. Further, frequency analyzer 210 calculates by time segments each spectrum forming the pulse wave, starting with the fundamental spectrum of the waveform, and followed by the second harmonic wave spectrum, and so on.

When microcomputer 181 outputs the initial waveform value WD of the pulse wave of one beat to frequency analyzer 210, a synchronized signal SYNC and the number N of waveforms WD included in that beat are output, and select signal S2 is switched. Further, while microcomputer 181 is outputting the waveform value WD of one beat, write address ADR5, which changes from 0 to N−1 in time with the transmission of each waveform value WD, is sequentially output.

Buffer memories 211 and 212 are provided to store the waveform values WD output from microcomputer 181 in this way.

Distributor 213 outputs waveform value WD of the pulse wave which is supplied via microcomputer 181 to whichever of buffer memories 211 and 212 is indicated by select signal S2.

Selector 214 selects either buffer memory 211 or 212, as indicated by select signal S2, and the waveform value WH read out from the selected memory is output to the high-speed regenerator 220 which will be explained below.

Selectors 215 and 216 select write address ADR5 or read-out address ADR 6 (explained below) generated by high-speed regenerator 220 in accordance with select signal S2, and supply the selected address to each of the buffer memories 211 and 212.

In the above-described switching distributor 213, switching between selectors 214~216 is controlled based on select signal S2. As a result, during the time in which data is being written in buffer memory 211, data is being read out from buffer memory 212 and supplied to high speed regenerator 220. Similarly, during the time in which data is being written in buffer memory 212, data is being read out from buffer memory 211 and supplied to high-speed regenerator 220.

High-speed regenerator 220 reads out waveform values corresponding to each of the beats from buffer memories 211 and 212. High-speed regenerator 220 varies the read-out address ADR6 within the range of 0 to N−1 (where N is the number of waveform values to be read out), and outputs the result. More specifically, high-speed regenerator 220 generates a read-out address ADR6 during the time in which each waveform value WD corresponding to a given beat is being written in one of the buffer memories. All waveform values WD corresponding to the beat preceding the given beat are read out from the other buffer memory a plurality of times. In this case, the generation of read-out address ADR6 is controlled so that all of the waveform values WD corresponding to one beat are read out within a fixed period of time. The time period for reading out all waveforms values corresponding to one beat can be changed in correspondence with the order of the spectrum to be detected. For example, the respective time periods can be switched from T, 2T, 3T . . . , when detecting the fundamental spectrum, the second harmonic wave spectrum, third harmonic wave spectrum . . . , respectively. Further, high-speed regenerator 220 contains an interpolator which interpolates the waveform value WH read out from buffer memory 211 or 212, and outputs the interpolated waveform value WH as a waveform value of a fixed sample frequency m/T (where m is a specific constant).

Sinusoidal wave generator 221 is a frequency convertible waveform generator which sequentially outputs each of the sinusoidal waves for periods T, 2T, 3T, 4T, 5T, and 6T corresponding to the order of the spectrum to be detected. Sinusoidal wave generator 221 is under the control of microcomputer 181.

Band pass filter 222 is a band pass filter in which the central frequency of the pass band is a specific value, 1/T.

Spectrum detector 223 detects amplitudes $H_1$~$H_6$ of each spectrum of the pulse wave based on the output level of band pass filter 222, and detects phases $\theta_1$~$\theta_6$ in each spectrum based on the difference in the phase of the detection signal of band pass filter 222 and the phase of the sinusoidal waves output by sinusoidal wave generator 221.

<3-3-2-2: Operation of Frequency Analyzer>

As explained above, frequency analyzer 210 detects the waveform spectrum at high speed by coupling its operation to waveform extraction memory 180. Accordingly, the operation of microcomputer 181 and waveform extraction memory 180 will be explained next.

<3-3-2-2-1: Waveform Partitioning>

As explained in the paragraph on the operation of waveform extraction memory 180 (section 3-3-1-2), when microcomputer 181 outputs the waveform collection directive START, the collection of waveforms and the peak information therefor is carried out. The collected waveforms are stored in waveform memory 184 and the peak information is stored in peak information memory 205 inside waveform extraction memory 180.

When stroke information corresponding to minimum point P2 is created, if the stroke information STRK in the peak information exceeds a specified value, i.e., the stroke value is large enough to consider that it corresponds to the rise in the waveform (see STRKM in FIG. 29), then microcomputer 181 carries out the following operation. Namely, in this case, microcomputer 181 reads out the waveform address of the minimum value which is the initial point of this stroke (see starting point P6 of STRKM in FIG. 29, for example) from peak information memory 205, and writes this waveform address in a shift register housed inside microcomputer 181. Subsequently, the equivalent operation is carried out as peaks P3, P4, . . . , are detected.

<3-3-2-2-2: Waveform Transmission>

Figure 33:
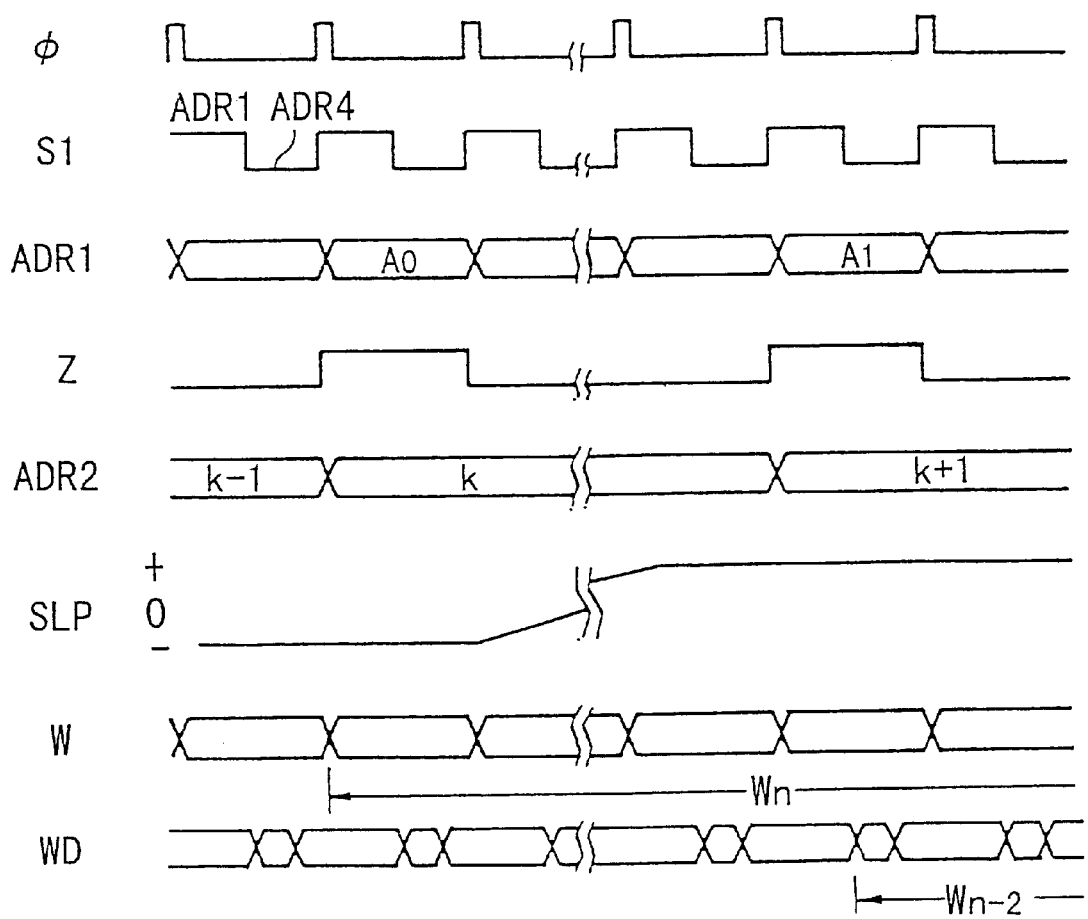
FIG. 33 is a timing chart showing the operation of the parameter extracting member.

In parallel with the preceding operation, microcomputer 181 sequentially reads out the waveform values from waveform memory 184 inside waveform extraction memory 180, and transmits these waveforms to frequency analyzer 210 as waveform data WD. As shown in FIG. 33, select signal S1 is switched in time with clock $\phi$, while waveform memory 184 switches between the write and read modes in synchronization with the switching of select signal S1.

Figure 32:
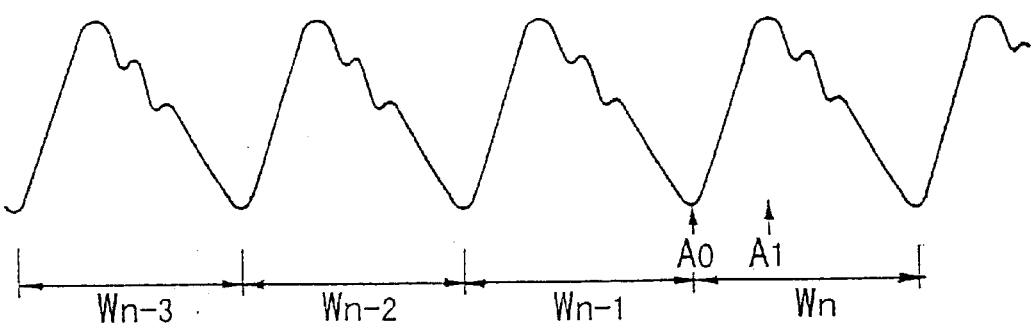
FIG. 32 shows the timing of the waveform transition.

However, in FIG. 32, when the waveform value of pulse wave Wn corresponding to a beat portion of a given beat is input to waveform memory 184, a zero cross detection pulse Z is generated when the initial minimum value of the pulse wave corresponding to this beat is input. The waveform value address ADR1=Ao is written in peak information memory 205 (refer to FIG. 33). Subsequently, when the maximum value (address A1) is input into waveform extraction memory 180, a zero cross detection pulse Z is again generated (see FIG. 33). When the stroke between this maximum value and the immediately preceding minimum value (address Ao) is above a specified value, then minimum value address Ao is written in the shift register inside microcomputer 181. The thus written waveform address is subsequently output from the shift register two beats later and taken up by microcomputer 181 as the initial address of the waveform value WD for the beat portion which is to be transmitted to frequency analyzer 210. In other words, in FIG. 32, when address Wn of a maximum value of waveform Wn corresponding to a given beat is written in the shift address, the initial address (i.e., initial minimum value address) of pulse wave Wn−2 from two beats prior to the current beat which was previously written in the shift register is output from the shift register, and detected by microcomputer 181.

At this point, microcomputer 181 references the contents of the shift register, and obtains the difference between the waveform address of the initial minimum value of pulse wave Wn−2 and waveform address of the initial minimum value of the next pulse wave Wn−1. In other words, microcomputer 181 obtains the number N of waveform values included in pulse wave Wn−1 of one beat portion. This result is output along with synchronization signal SYNC to frequency analyzer 210. Select signal S2 is switched in time with synchronization signal SYNC, with the internal connections between distributor 213 and selectors 214~216 becoming as shown by the solid line in FIG. 31, for example.

Microcomputer 181 sequentially increases read-out address ADR4 from the initial minimum value waveform address of pulse wave Wn−2, and supplies the result to waveform memory 184 via selector 192. Read-out address ADR4 changes at a faster speed (for example, twice as fast) than write address ADR1. This is so that all of the waveform values corresponding to pulse wave Wn−2, the pulse wave preceding pulse wave Wn−1, can be read out prior to the input of the maximum value of pulse wave Wn+1, which is associated with the beat proceeding pulse wave Wn, to waveform extraction memory 180. In parallel with the storage of pulse wave Wn in waveform memory 184, the waveform value WD of pulse wave Wn−2 from two beats previous is read out from waveform memory 184 by microcomputer 181, transmitted to frequency analyzer 210, and sequentially supplied to buffer memory 211 via distributor 213. Write address ADR5 is sequentially increased from 0 to N−1 in synchronization with the sequential supply of waveform values WD to buffer memory 211, and is then supplied to buffer memory 211 via selector 215. As a result, each of the waveform values WD corresponding to pulse wave Wn−2 is stored in each of the recording areas of addresses 0~N−1 of buffer memory 211.

<3-3-2-2-3: High-speed Regeneration>

In parallel with the above operation, high-speed regenerator 220 outputs read-out address ADR6, and supplies it to buffer memory 212 via selector 216. As a result, each waveform value WD corresponding to pulse wave Wn−3, the beat prior to pulse wave Wn−2, is read out from buffer memory 212, and taken up by high-speed regenerator 220 via selector 214.

Figure 34:
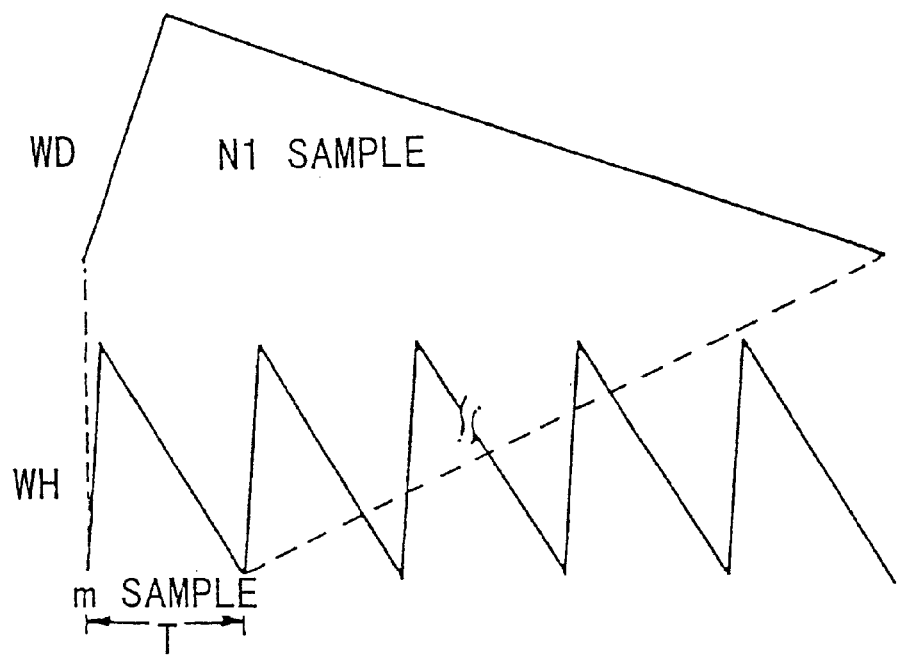
FIG. 34 is a diagram provided for explaining the operation of the high-speed regenerator in the frequency analyzer.
Figure 35:
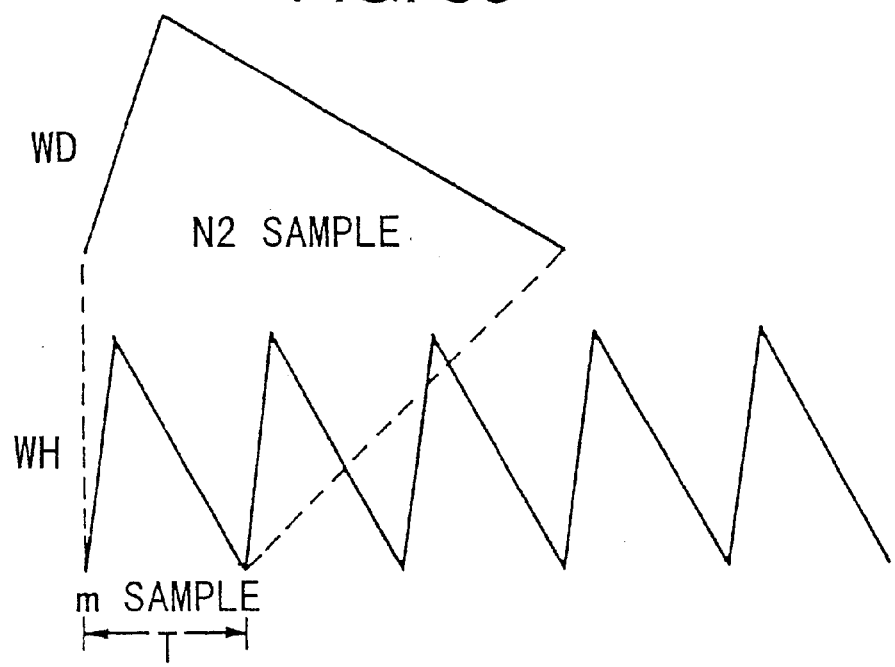
FIG. 35 is a diagram for explaining the operation of the high-speed regenerator.

Each waveform value WD corresponding to pulse wave Wn−3 in buffer memory 212 is repeatedly read out a plurality of times, at a speed which is faster than the storing of each of the waveform values corresponding to pulse wave Wn−2 in buffer memory 211. In this case, the speed at which read-out address ADR6 is increased is controlled so that all of the waveform values WD corresponding to pulse wave Wn−3 can be read out within a fixed time period T. In other words, high-speed regenerator 220 increases read-out address ADR6 at a high speed when the number of waveform values WD to be read out from buffer memory 212 is a large value N1, as shown in FIG. 34. Conversely, high-speed regenerator 220 increases read-out address ADR6 at a low speed when the number of waveform values WD to be read out from buffer memory 212 is a small value N2, as shown in FIG. 35. Accordingly, read-out address ADR6 varies from 0~N1−1or 0~N2−1 within a fixed period of time T. Waveform values WD sequentially read out in this way undergo interpolation calculations in high-speed regenerator 220, to become waveform values of a fixed sampling frequency m/T, which are then supplied to band pass filter 222.

<3-3-2-2-4: Spectrum Detection>

Band pass filter 222 selects a signal in which the frequency is 1/T from among the time series data of the received waveform values, and passes the signal through to spectrum detector 223.

Figure 36:
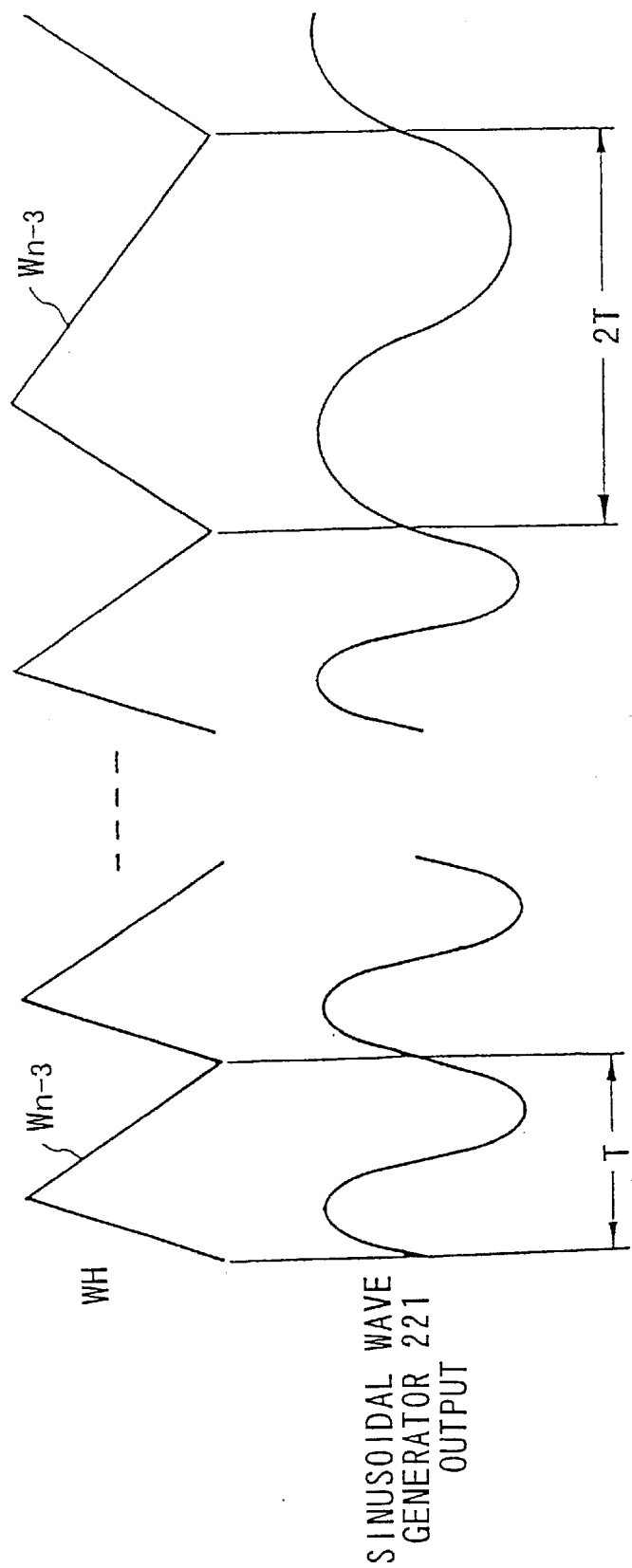
FIG. 36 is a diagram for explaining the operation of the high-speed regenerator and the sinusoidal wave generator.

As shown in FIG. 36, sinusoidal wave generator 221 generates a sinusoidal wave in which the frequency is T, and supplies the wave to the spectrum detector 223. Spectrum detector 223 detects the output signal level of band pass filter 222 over several waves, and outputs the representative value as the amplitude H1 of the fundamental wave spectrum of pulse wave Wn−3. Spectrum detector 223 also detects over several waves the difference in the phase of the output signal of band pass filter 222 and the phase of the sinusoidal wave output from sinusoidal wave generator 221, and outputs the representative value as the phase $\theta_1$ of the fundamental wave spectrum of pulse wave Wn−3. For each representative value, the moving average value of the phase difference and the output signal level corresponding to each wave prior to the output of the fundamental spectrum, for example, is calculated.

High-speed regenerator 220 sets the speed of the increase in read-out address ADR6 to ½ when detecting the fundamental spectrum, for example, so that all of the waveform values of the pulse wave Wn−3 can be read out within a fixed period of time 2T, repeatedly reads outs waveform value WH corresponding to pulse wave Wn−3, and supplies the waveform values to band pass fiber 222 (see FIG. 36). From among the time series data comprising waveform values WH, those signals in which the frequency is 1/T, i.e., those signal corresponding to the second harmonic wave of pulse wave Wn−3, pass through band pass filter 222 and are supplied to spectrum detector 223. As a result, the amplitude $H_2$ of the second harmonic wave spectrum of pulse wave Wn−3 is detected and output by spectrum detector 223. Sinusoidal waveform generator 221 generates sinusoidal waves in which the period is 2T and supplies them to spectrum detector 223 (see FIG. 36). As a result, phase $\theta_2$ of the fundamental spectrum of pulse wave Wn−3 is output by spectrum detector 223.

Thereafter, the speed of increase of read-out address ADR6 is sequentially switched from ⅓, ¼, ⅕ and ⅙ in the case where detecting the fundamental spectrum, while, in concert with this, the period of the sinusoidal wave generated by sinusoidal wave generator 221 is sequentially switched from 3T, 4T, 5T and 6T. The amplitudes $H_3$~$H_6$ and the phases $\theta_3$~$\theta_6$ of the third through sixth order high harmonic wave spectrum are output from spectrum detector 223 by means of the same operation as above. Each of the spectrums of the thus obtained pulse wave Wn−3 is taken up by microcomputer 181. Microcomputer 181 calculates the frequency f=1/(Nτ) of the fundamental wave using the period τ of the clock φ and the number N of waveform values WD corresponding to pulse wave Wn−3, and outputs this result together with the aforementioned spectrum.

Next, when pulse wave Wn+1, which is one beat after pulse Wn, starts to rise and the initial maximum value is input into waveform extraction memory 180, a synchronized signal SYNC is generated by microcomputer 181 and the number N of the waveform values WD included in pulse wave Wn−2 is output. Further, select signal S2 is inverted, with the internal connections between distributor 213 and selectors 214~216 becoming as indicated by the broken line in FIG. 31. In parallel with the storage of pulse wave Wn+1 in waveform memory 184, microcomputer 181 reads out from waveform memory 184 the waveform value WD of pulse wave Wn−1 from two beats before, and transmits it to frequency analyzer 210. From there, the waveform value WD is sequentially supplied to buffer memory 212 via distributor 213.

In parallel with this operation, each of the waveform values WD corresponding to pulse wave Wn−2 from one beat prior to pulse wave Wn−1 is read out from buffer memory 211 by high-speed regenerator 220, interpolated by high-speed regenerator 220, and output as waveform value WH. The same processing as carried out on pulse wave Wn−3 is applied to the waveform value WH for pulse wave Wn−2, to obtain the spectrum therefor.

Subsequently, the equivalent processing as described above is carried out on each of the sequentially arriving pulse waves, thereby obtaining a continuous spectrum for each of the pulse waves. In other words, amplitudes $H_1$~$H_6$ and phases $\theta_1$~$\theta_6$, which are the parameters corresponding to each of these beats, are obtained. Of these, it is known that changes in physiological condition are well expressed in $\theta_4$. Therefore, CPU 1 can determine this change as an indicator expressing physiological information, and confirm the degree of relaxation and the effect of autogenic training using biofeedback.

<3-4: Wavelet Transformation>

The preceding embodiments determined the change in the pulse waveform by carrying out FFT conversion of the pulse waveform from pulse wave sensor 5. The present invention is not limited to the use of FFT, however. For example, it is also possible to use the results of analysis of the pulse wave in each frequency region after carrying out wavelet transformation, to obtain the change in the pulse waveform.

An explanation will now be made of the structure for carrying out wavelet transformation of the pulse waveform from pulse waveform sensor 5. This structure may be realized by substituting physiological information extractor 101 shown in FIG. 1 with the structure shown in FIG. 37.

Figure 37:
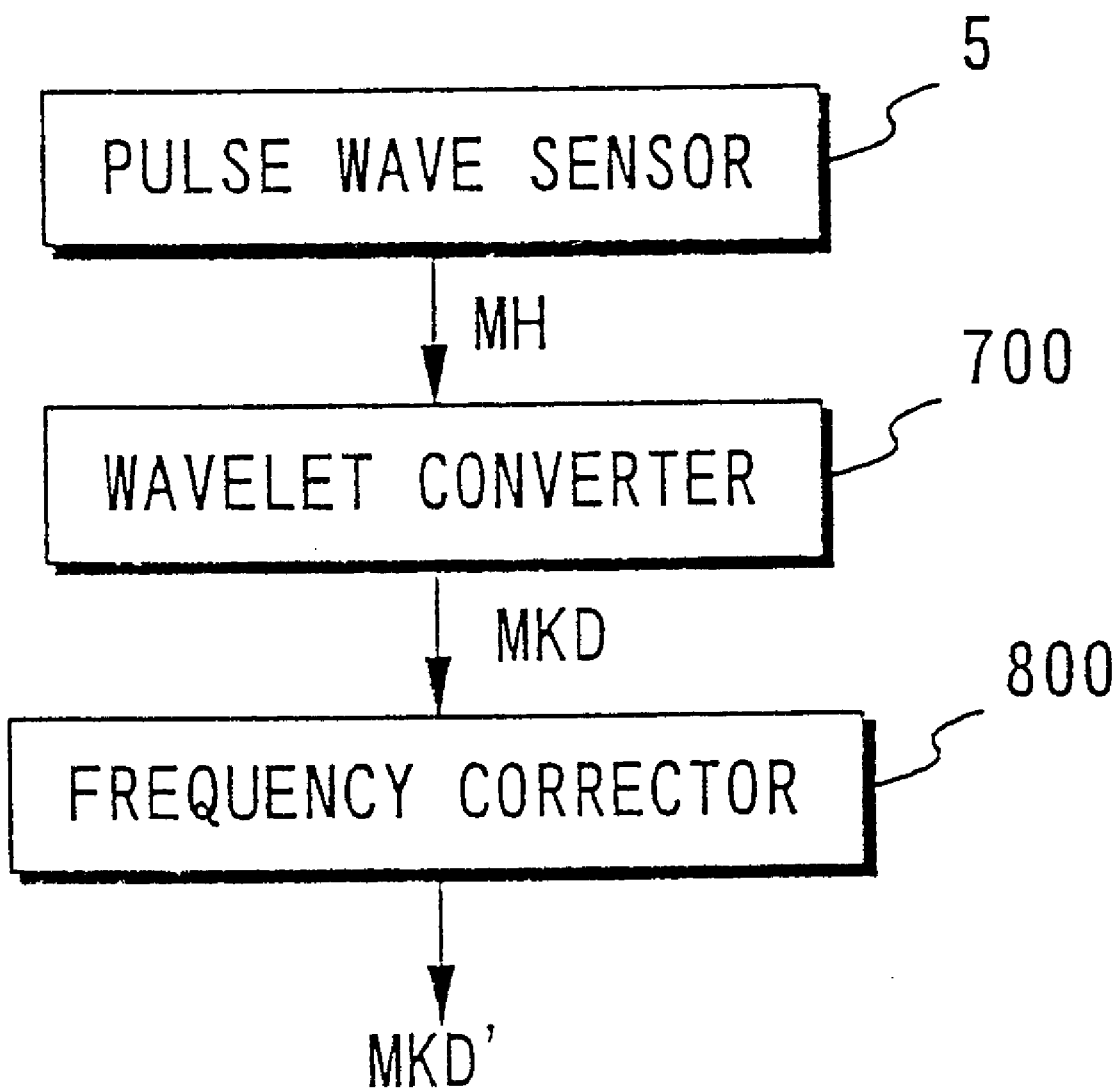
FIG. 37 is a block diagram showing the structure for carrying out wavelet conversion of the pulse waveform.

In FIG. 37, wavelet converter 700 carries out conventional wavelet transformation with respect to the pulse wave signal MH which is output from pulse wave sensor 5, and generates pulse wave analysis data MKD.

In general, in time frequency analysis in which the signal is simultaneously analyzed in both the time and frequency domains, the wavelet is the unit by which the signal part is extracted. Wavelet transformation shows the size of each part of the signal extracted in these units. As the base function for defining wavelet transformation, a function $\psi(x)$ which has been localized with respect to both time and frequency is introduced as the mother wavelet. Here, wavelet transformation employing the mother wavelet $\psi(x)$ of a function f(x) is defined as follows.

$$(W_\psi f)(b, a) = \int_{-\infty}^{\infty} \frac{1}{\sqrt{a}} \psi\left(\frac{x-b}{a}\right) f(x) dx \qquad (1)$$

In equation (1), b is the parameter employed when translating the mother wavelet $\psi(x)$, while a is the parameter used when scaling. Accordingly, wavelet ψ((x−b)/a) in equation (1) is the wavelet obtained when transitioning mother wavelet ψ(x) by b only, and scaling it by a only. Since the width of the mother wavelet ψ(x) is extended in correspondence to the scale parameter a, 1/a corresponds to the frequency. The structure of wavelet converter 700 will be explained in greater detail below.

Frequency corrector 800 carries out frequency correction on pulse wave analysis data MKD. When comparing data from different frequency regions, it is necessary to correct for the effect of the term $[1/a^{1/2}]$ corresponding to frequency in the preceding equation (1). Frequency corrector 800 is provided for this purpose. Namely, frequency corrector 800 generates corrected pulse wave data MKD' by multiplying wavelet data WD by a coefficient $a^{1/2}$. As a result, it is possible to carry out correction based on each of the corresponding frequencies, so that the power density per frequency becomes constant.

<3-4-1: Wavelet Converter>

Figure 38:
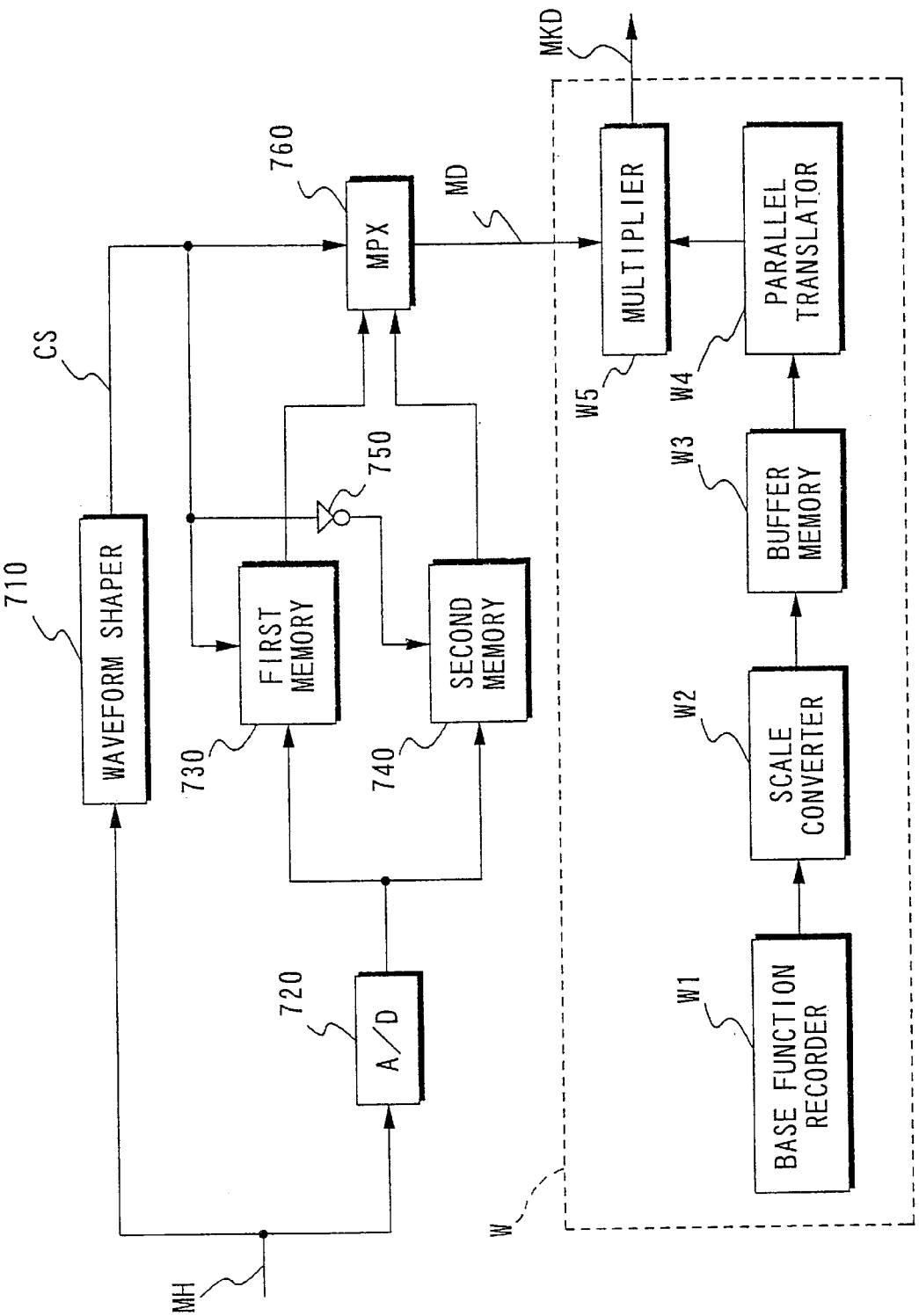
FIG. 38 is a block diagram showing the structure of the wavelet converter.

Next, the detailed structure of wavelet converter 700 will be explained with reference to FIG. 38.

Pulse waveform MH from pulse wave sensor 5 is supplied to waveform shaper 710 and A/D converter 720. Waveform shaper 710 generates a clock CK and control signal CS in synchronization with pulse waveform MH. A block diagram of waveform shaper 710 is shown in FIG. 39. In this figure, ringing filter 711 has a high Q value having a middle frequency of 2.2 Hz and a pass band of 0.8~3.5 Hz. The fundamental wave component of the pulse waveform is typically in the range of 0.8~3.5 Hz. Therefore, the fundamental waveform component is extracted when pulse waveform MH passes through ringing filter 711. For example, when the pulse waveform MH shown in FIG. 40A passes through ringing filter 711, the sinusoidal wave shown in FIG. 40B is obtained.

Next, zero cross detection circuit 712 is formed of a comparing member or the like, and generates a rectangular wave by comparing the grand level and the output signal of ringing filter 101. This rectangular wave is synchronized with the heartbeat. For example, if the output signal of ringing filter 712 is as shown in FIG. 40B, then the output signal from zero cross detection circuit 712 is as shown in FIG. 40C.

Comparing member 713, loop filter 714, voltage control oscillating circuit 715, and frequency dividing circuit 716 form one type of PLL(phase locked loop). When the output signal from zero cross detection circuit 712 is supplied to as one input to comparing member 713 and the output signal from frequency dividing circuit 716 is supplied as the other input to comparing member 713, comparing member 713 outputs an error signal in response to the phase difference between these two inputs. When the error signal is supplied to voltage control oscillation circuit 715 via loop filter 714, voltage control oscillation circuit 715 outputs a clock CK. Clock CK is divided into 1/8s at frequency dividing circuit 716, and fed back as the other input to comparing member 713. In this case, the frequency of clock CK is 8-fold greater as compared to the frequency of the signal output from zero-cross detection circuit 712, as shown in FIG. 40D. Thereafter, clock CK is divided in half at frequency dividing circuit 717, and output as the control signal CS shown in FIG. 40E.

The explanation will now return again to FIG. 38. Pulse waveform MH is converted to a digital signal by A/D converter 720, and stored in first memory 730 and second memory 740. Control signal CS is directly supplied to the write enable terminal of first memory 730, and control signal CS which has been inverted by inverter 750 is supplied to the write enable terminal of second memory 740. As a result, first and second memories 730,740 alternately store pulse waveform MH in clock period units.

Multiprocessor 760 selects pulse wave data MD alternately read out from first and second memory 730 and 740, and outputs this data to base function developer W. Pulse wave data MD is read out from second memory 740 during the write interval for first memory 730, and then written into second memory 740 during the read out time for first memory 730.

Next, base function developer W is designed to carry out processing to calculate the above equation (1). Base function developer W carries out this processing at the clock period supplied by clock CK. Base function developer W consists of a base function recorder W1 which records the mother wavelet ψ(x); a scale converter W2 which converts scale parameter a; buffer memory W3; parallel translator W4 which carries out translation; and multiplier W5. Please note that various types of wavelets may be suitably employed for mother wavelet ψ(x) which is stored in base function recorder W1, including Gabor wavelet, Mexican hat wavelet, Harr wavelet, Meyer wavelet, Shannon wavelet and the like.

When a mother wavelet ψ(x) is read out from base function recorder W1, conversion of scale parameter a is carried out by scale converter W2. Scale parameter a corresponds to period, thus, the bigger a is, the more the mother wavelet extends above the time axis. In this case, the quantity of data for mother wavelet ψ(x) recorded in base function recorder W1 is fixed, so that when a gets larger, the amount of data per unit time decreases. Scale converter W2 carries out interpolation to correct this, and generates a function ψ(x/a) by performing weeding out processing when a gets smaller. This data is stored once in buffer memory W3.

Next, parallel translator W4 reads out function ψ(x/a) from buffer memory W3 at a timing in response to translation parameter b, carrying out the parallel transition of function ψ(x/a), to generate a function ψ(x−b/a).

Figure 41:
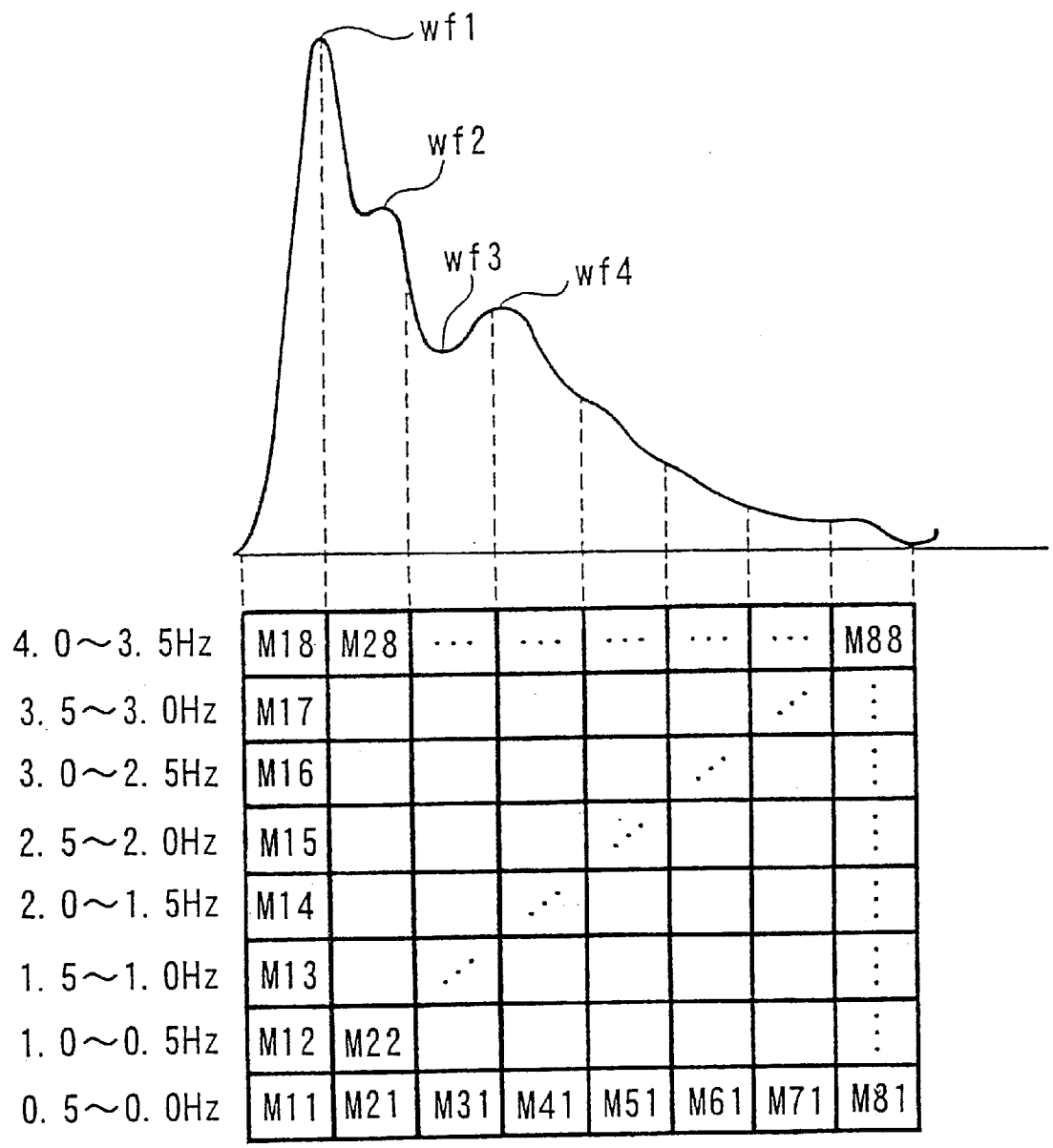
FIG. 41 shows pulse wave analysis data obtained from the pulse wave of a single beat.

Next, multiplier W4 carries out wavelet transformation by multiplying variable $1/a^{1/2}$, function ψ(x−b/a) and the pulse wave data MD, to generate pulse wave analysis data MKD. In this example, the pulse wave analysis data MDK is segregated into the eight frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output. Base function developer W carries out calculation processing at the clock periods, as described above. Since the clock frequency is set to be 8-fold greater than the frequency of the fundamental wave of pulse waveform MH, pulse wave analysis data MKD which is generated per heart beat, becomes data M11~M88, as shown in FIG. 41.

Correction of this pulse wave analysis data MKD is carried out by frequency corrector 800, and supplied to storage member 102 and judging member 103 shown in FIG. 1 as corrected pulse wave data MKD', i.e., as an indicator expressing physiological state.

Note that the structures shown in FIGS. 38 through 41 for the wavelet transformer are merely examples. Rather, the structure of this element may be determined based on which indicator of physiological state is to be employed. For example, if the indicator is the amplitude value of the pulse waveform, then the structure shown in the figures is acceptable. If, however, a time axis is involved, such as for the RR50 value, then a structure may be employed which carries out wavelet transformation at fixed intervals without determining the beat timing at waveform shaper 710, and determines the interval in which data M18 appears. The reason that data M18 was designated in this case is because it is easy to specify due to a sharp peak at each beat in the pulse waveform where the data expressing the high frequency component becomes large in this area of rise.

<4: Other Examples of Embodiments>

Other examples of embodiments of the present invention will now be explained.

<4-1: Necklace Model>

Figure 42:
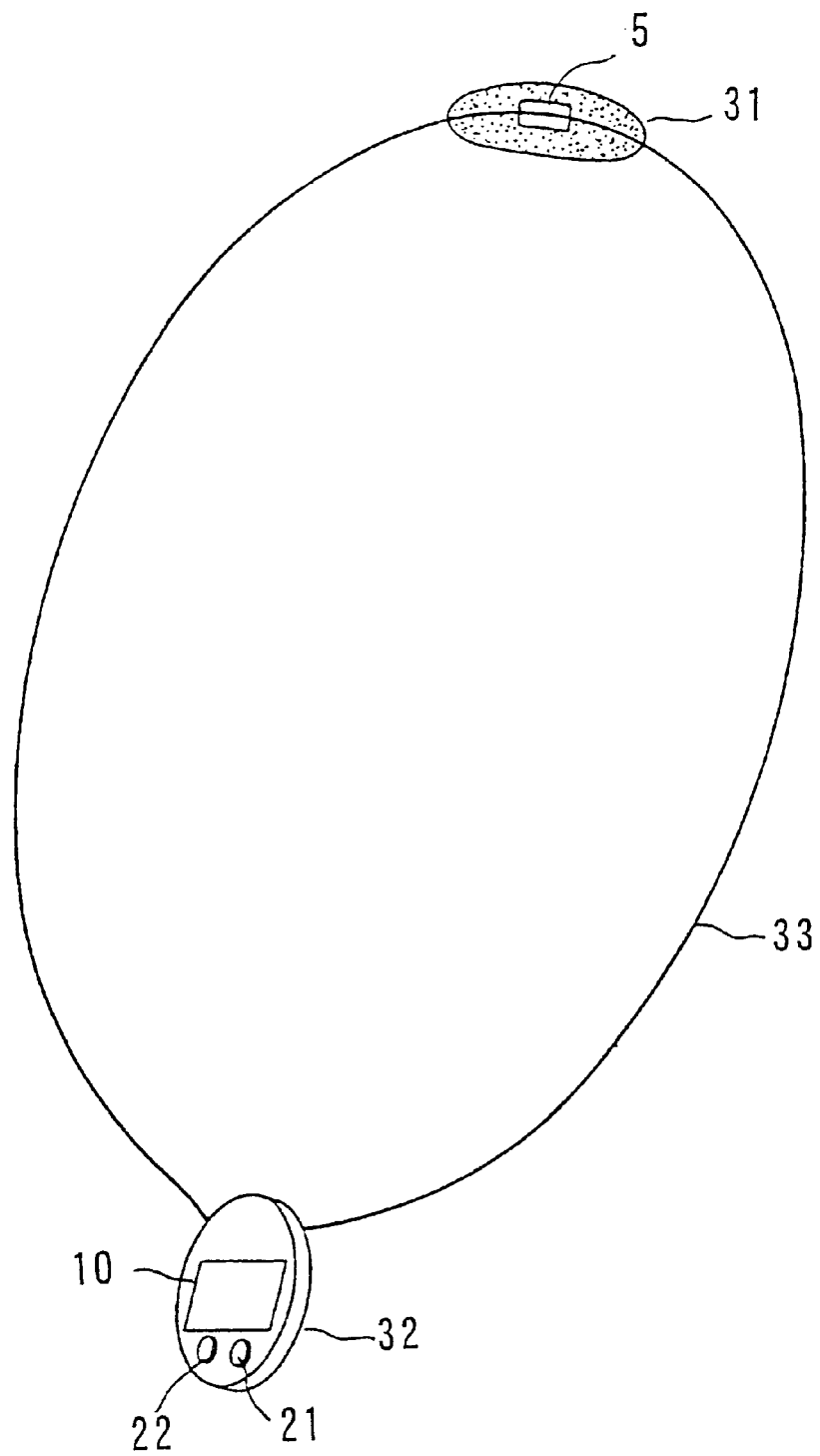
FIG. 42 shows the outer structure in the case where the device is rendered into the form of a necklace.

In addition to the wrist watch described above, a variety of other portable devices may be considered. For example, the device of the present invention may be combined with an accessory, such as the necklace shown in FIG. 42. In this figure, 31 is a sensor pad formed of a shock-resistant material in the shape of a sponge. Pulse wave sensor 5 is attached to the center of sensor pad 31 so as to come in contact with the surface of the skin. When the user puts on the necklace, sensor 5 comes in contact with the skin on the back surface of the neck, to measure the pulse wave. In FIG. 42, essential components of the device may be incorporated into a case 32 which is in the form of a broach which is hollow inside. The pulse wave sensor 5 and case 32 are each attached to chain 33, and are connected electrically via a lead wire (not shown) which is embedded in chain 33.

<4-2: Eyeglasses>

Figure 43:
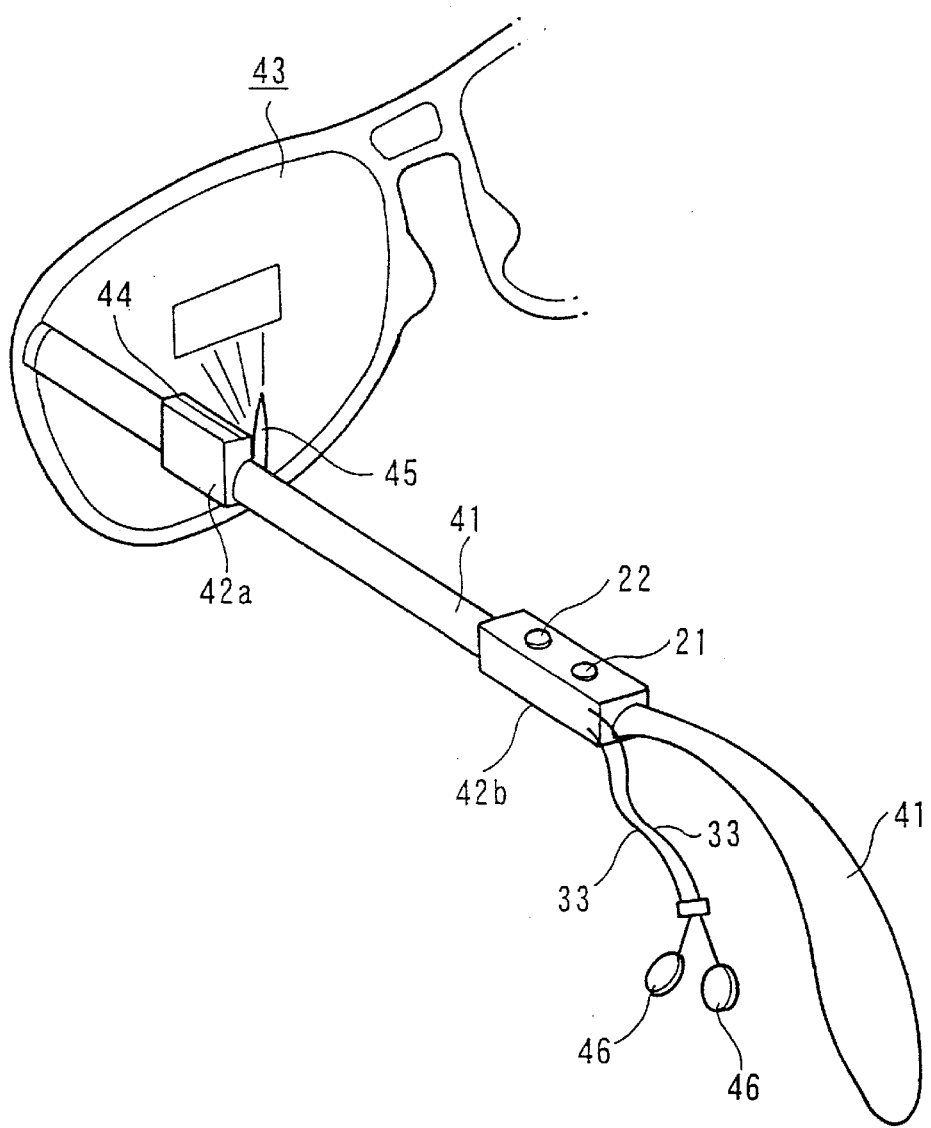
FIG. 43 shows the outer structure in the case where the device is rendered into the form of a pair of eyeglasses.

As another example of a portable device, the device of the present invention may be combined with a pair of eyeglasses, such as shown in FIG. 43. In this arrangement, the main body of the device in this embodiment is attached to the stems 41 of the eyeglass frame. The main body of the device is divided into a case 42a and case 42b, which are connected electrically via a lead wire embedded in stems 41. The lead wires may also be extended along the outside of stems 41.

A liquid crystal panel 44 is attached over the entire surface of the lens 43 side of case 42a. A mirror 45 is fixed to the edge of this lateral surface at a specific angle. A drive circuit for liquid crystal panel 44 which includes a light source (not shown) is incorporated in case 42a. The light emitted from this light source passes via liquid crystal panel 44, and is reflected at mirror 45 to incident on lens 43 of the eyeglasses. Accordingly, lens 43 in this arrangement corresponds to display device 10 in FIG. 2.

The principal elements of the device are incorporated in case 42b. Pulse wave sensor 5 is housed in pads 46. By clipping the earlobe between pads 46, the pulse wave sensor can be fixed in place.

<4-3: Card Model>

Figure 44:
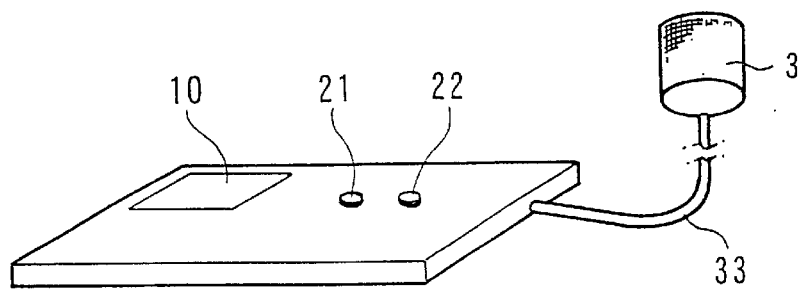
FIG. 44 shows the outer structure in the case where the device is rendered into the form of a pocket card.

As another example of an embodiment, the device of the present invention may be rendered in the form of a card such as shown in FIG. 44. The device in this form is stored in the left breast pocket of the subject's shirt, for example. Pulse wave sensor 5 is attached between the base and second joint of the index finger on the user's left hand, in the same manner as in the case of the wrist watch shown in FIG. 6, for example. Pulse wave sensor 5 is electrically attached via cable 31 to A/D converter 6 housed in a case.

<4-4: Pedometer>

Figure 45A:
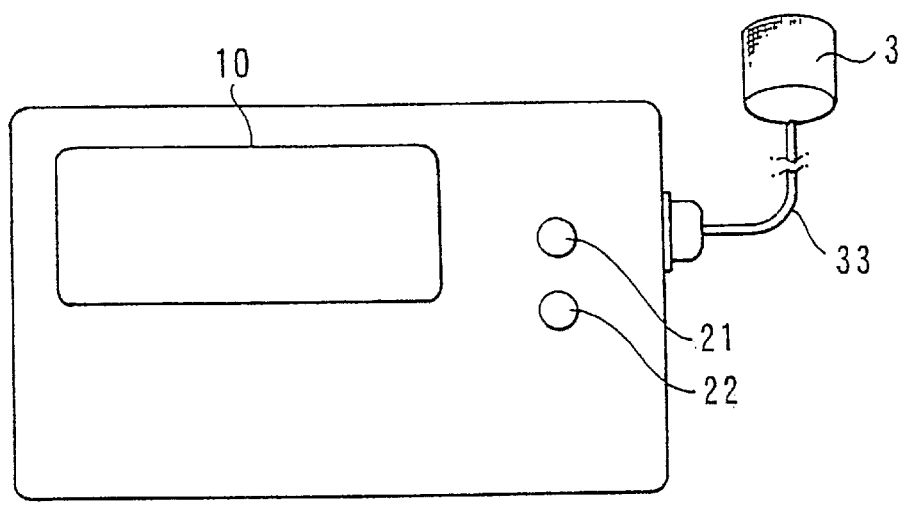
FIG. 45A shows the outer structure in the case where the device is rendered into the form of a pedometer.
Figure 45B:
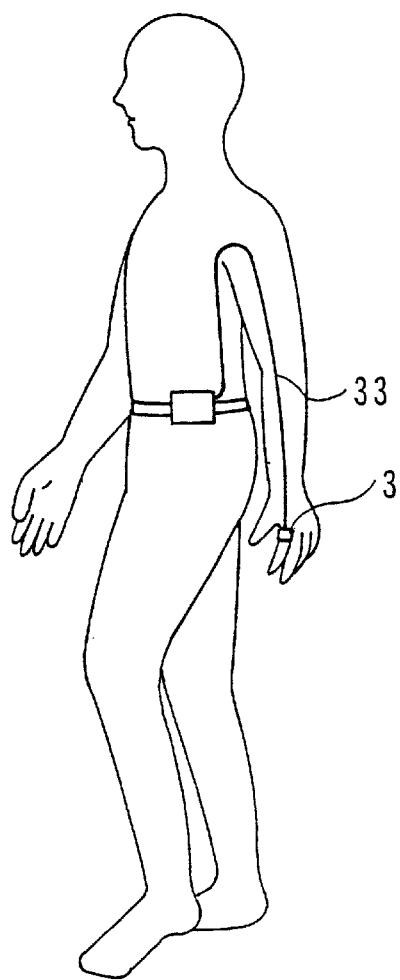
FIG. 45B shows the arrangement for attachment of this device.

As another embodiment of the present invention, the pedometer shown in FIG. 45A may be considered, for example. The main body of this pedometer device is attached to the subject's waist belt as shown in FIG. 45B. As shown in FIG. 45B the main body of the pedometer device is attached to the subject's waist belt. As in the case of the card, pulse wave sensor 5 in this embodiment is attached between the base and second joint of the index finger on the left hand. In this case, cable 33 for joining the main body of the device and the pulse wave sensor is preferably sown into the clothing, so as not to hinder the user's exercise.

<5: Other Arrangements for Notification>

The preceding embodiments 1 and 2 used a sound source 7 which relied on the user's sense of hearing to inform the user of indicators expressing the physiological state. However, a variety of other methods for notification may be considered.

Since the user has his eyes closed, the means of notification must rely on a sense other than sight.

Therefore, a method is available using sound source 7 to notify the user by converting various notices into a synthesized voice. For example, a number value such as the indicator RR50 or a grade may be read out to the user without modification. Similarly, a synthesized voice may be used to notify the user in the case where movement exceeds a specific value. It is also acceptable to provide a mechanism which plays a musical tune which has been preset to correspond to the notification contents.

A method employing the user's olfactory sense may also be considered, in which a mechanism for emitting a fragrance or the like is provided to the device. The type of fragrance emitted is varied according to the notice to be conveyed.

Finally, a vibration alarm which communicates a vibration to the user by rotating an eccentric load may be employed as a method relying on the user's tactile sense. In this case, the strength of frequency of the vibration is varied according to the notice to be conveyed.

Notification that a) indicators are rising, b) a sufficiently relaxed state has been entered, and c) measurements are being shut-off, all take place during the user's autogenic training. Therefore, it is also acceptable to employ notification using the sense of hearing in the case of a), notification using the olfactory sense in the case of b), etc. Alternatively, a tune, chime and beep may be used for notifying a) through c), respectively.

<6: Modifications>

In addition to the above-described first and second embodiments, the various indictors expressing physiological state, and device arrangements, the following modifications are also possible.

<6-1: Pulse Wave Sensor, Acceleration Sensor>

Pulse wave sensor 5 may be in the form of an optical, pressure, or push-type sensor, provided that it is combined with a portable device or accessory. Further, the site of attachment of pulse wave sensor 5 is not particularly limited. Rather, any arrangement is acceptable, provided it is combined with a portable device.

Similarly, acceleration sensor 13 may be attached to any site on the human body.

<6-2: Setting of Target Values>

In the preceding first and second embodiments, the upper limit and target values for autogenic training were set from the external device. However, the present invention is not limited thereto. For example, the user may perform the settings himself using operator 4, under the guidance of a physician or other director.

<6-3: Analogue Display Device>

After the user opens his eyes following autogenic training, the display of the measured and target values may be carried out using the analog hands on a watch, to express the change in physiological state.

Figure 16:
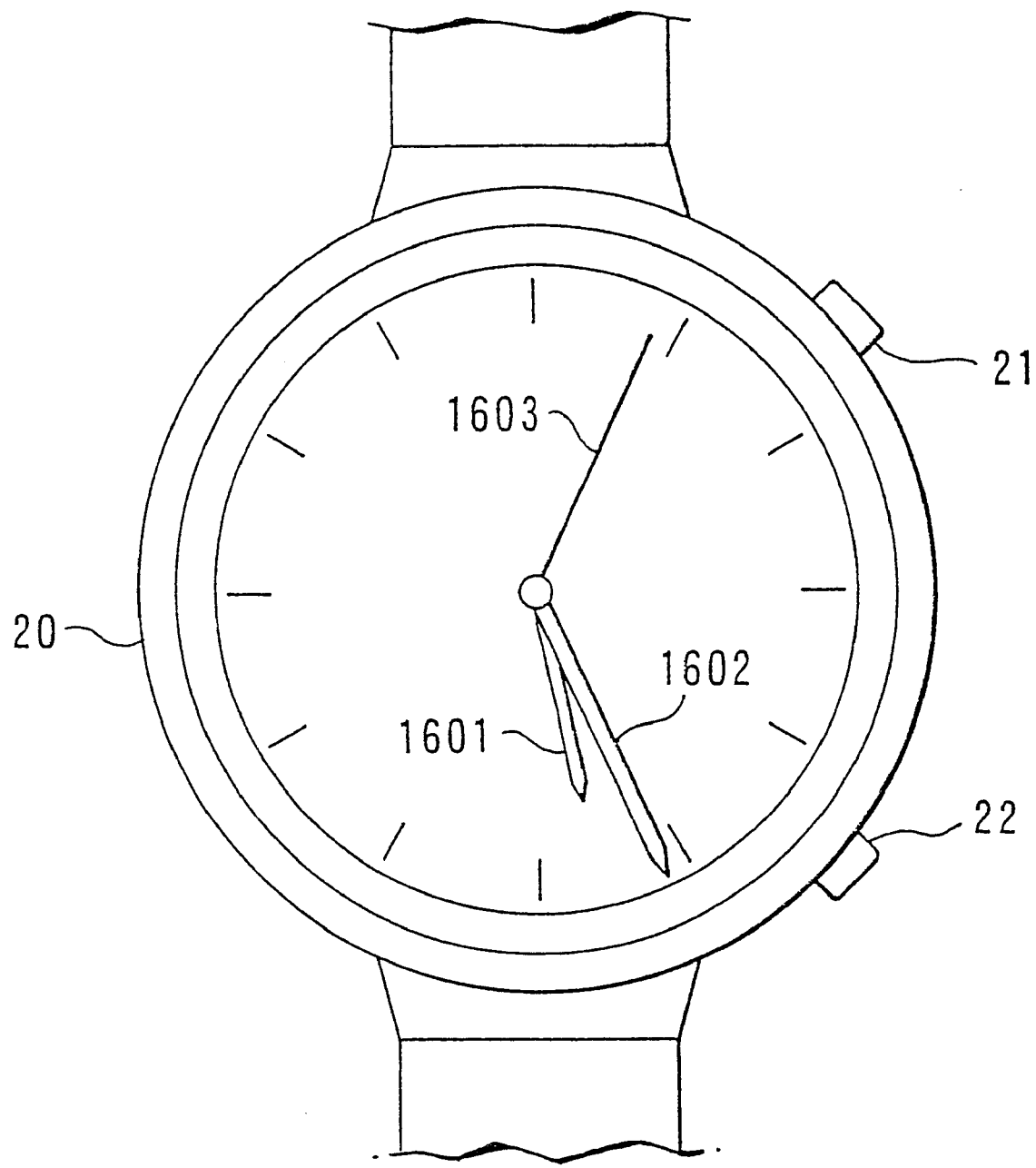
FIG. 16 shows an example in which the target value and the measured value for the rate of change in the indicators are displayed on an analog watch.

Namely, as shown in FIG. 16, an hour hand 1601, minute hand 1602, and second hand 1603 are employed, with the target value and the measured value for the change in the indicator expressing physiological state assigned to hour hand 1601 and minute hand 102, respectively. In the case shown in FIG. 16, when the hand is driven in the clockwise direction as the change in the indicators becomes larger. In the example in this figure, hour hand 1602 is closer to the 6 o'clock position than the minute hand 1602, indicating that the measured value has not yet reached the target value. A design is also acceptable in which hands other than hour hand 1601, minute hand 1602, and second hand 1603 are provided.

Figure 17:
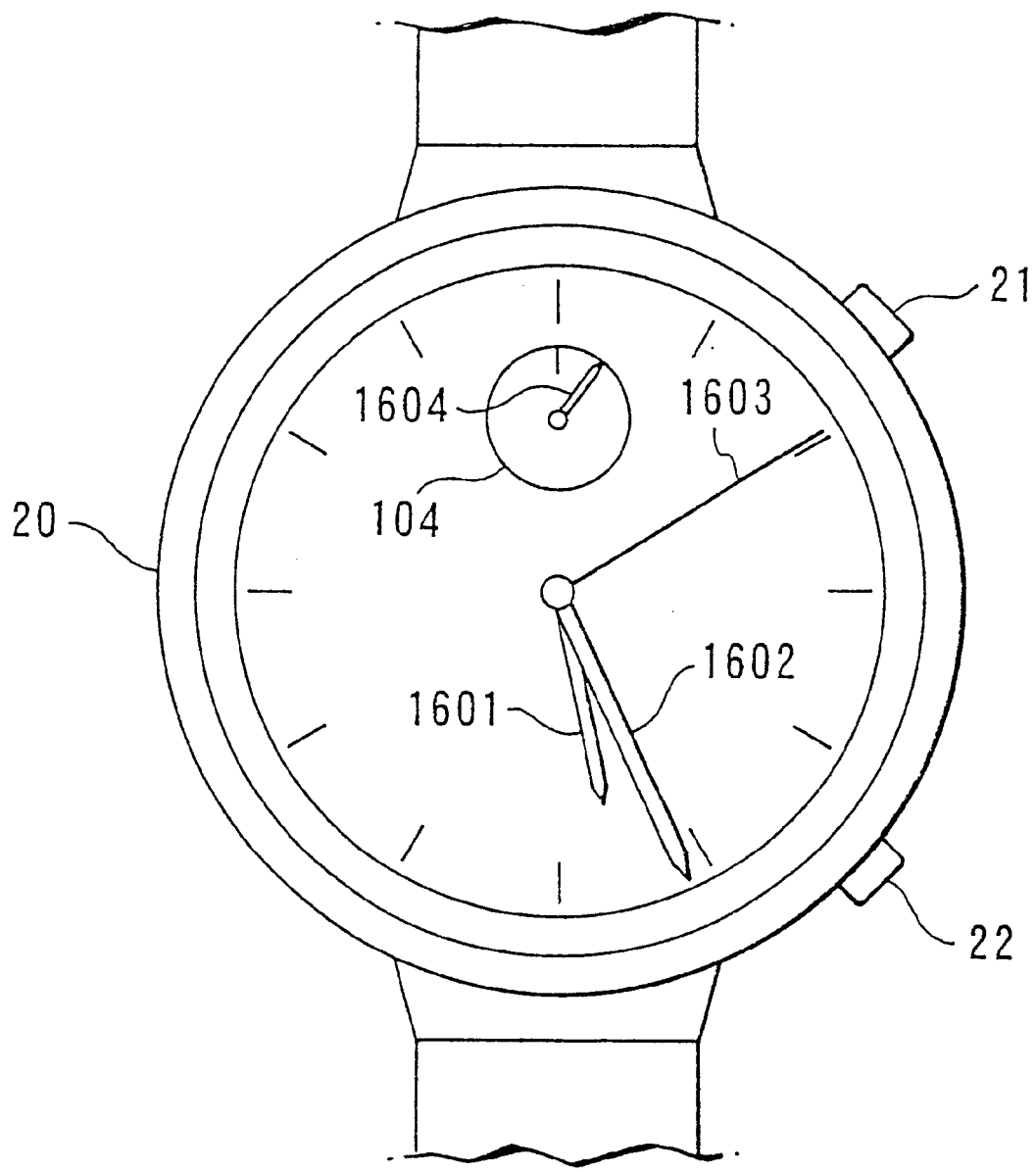
FIG. 17 shows an example in which the target value and the measured value for the rate of change in the indicator are displayed on an analog watch.

For example, a single hand may be used to express the relationship between the target value and the measured value, provided that the relationship between these values is clear. An example of such a design is shown in FIG. 17. As shown in this figure, a small hand 1605 expressing the difference between the measured and target values of the indicator is provided to display surface 1604. The 12 o'clock position on this display corresponds to the target value, while small hand 1605 indicates the measured value. Namely, the measured value is displayed when the target value is defined as the standard using the position of small hand 1605. Accordingly, if the measured value and the target value coincide, then small hand 1605 is positioned at 12 o'clock. If the measured value exceeds the target value, then small hand 1605 is positioned at 1 o'clock, for example. If the measured value is less than the target value, then small hand 1605 is positioned at 11 o'clock, for example.

The movement of small hand 1605 may be reversed from that described above. In this example, hour hand 1601, minute hand 1602, and second hand 1603 are all employed simply to express the time.

What is claimed is:

1. A biofeedback guidance device comprising:
    a pulse wave detecting means for detecting a pulse waveform of a living body, said pulse waveform having sets of adjacent pulse waves;
    an analysis means for carrying out spectral analysis of changes in time intervals of each set of adjacent pulse waves obtained from said pulse waveform detected by said pulse waveform detecting means;
    a calculating means for calculating an indicator, wherein said indicator is calculated as an amplitude value, or a ratio of two amplitude values, of a spectral component obtained by said analyzing means;
    an indicator providing means for providing in real-time said indicator calculated by said calculating means or providing in real-time a second indicator determined from said indicator calculated by said calculating means;
    an evaluating means for evaluating changes of a state of said living body on the basis of said indicator calculated by said calculating means at not less than two different points in time; and
    a guidance providing means for providing guidance, for use by said living body to control said state of said living body, on the basis of a result of the evaluation carried out by said evaluating means.

2. The biofeedback guidance device of claim 1, further comprising:
    a body motion detecting means for detecting a body motion of said living body; and
    a body motion notifying means for providing notification of said body motion detected by said body motion detecting means.

3. A biofeedback guidance device comprising:
    a pulse waveform detecting means for detecting a pulse waveform of a living body;
    a calculating means for calculating an indicator, wherein said indicator is calculated as a number of times that a time difference between adjacent pulse waves obtained from said pulse waveform detected by said pulse waveform detecting means exceeds a certain value;
    an indicator providing means for providing in real-time said indicator calculated by said calculating means or providing in real-time a second indicator determined from said indicator calculated by said calculating means;
    an evaluating means for evaluating changes of a state of said living body on the basis of said indicator calculated by said calculating means at not less than two different points in time; and
    a guidance providing means for providing guidance, for use by said living body to control said state of said living body, on the basis of a result of the evaluation carried out by said evaluating means.

4. The biofeedback guidance device of claim 3, further comprising:
    a body motion detecting means for detecting a body motion of said living body; and
    a body motion notifying means for providing notification of said body motion detected by said body motion detecting means.

* * * * *